US012558351B2

(12) United States Patent
Li et al.

(10) Patent No.: US 12,558,351 B2
(45) Date of Patent: Feb. 24, 2026

(54) COMPOSITIONS AND METHODS FOR ENHANCING CANCER IMMUNE CHECKPOINT THERAPY

(71) Applicant: DUKE UNIVERSITY, Durham, NC (US)

(72) Inventors: Chuan-Yuan Li, Durham, NC (US); Mengjie Hu, Durham, NC (US); Min Zhou, Durham, NC (US); Fang Li, Durham, NC (US)

(73) Assignee: Duke University, Durham, NC (US)

( * ) Notice: Subject to any disclaimer, the term of this patent is extended or adjusted under 35 U.S.C. 154(b) by 936 days.

(21) Appl. No.: 17/439,903

(22) PCT Filed: Mar. 20, 2020

(86) PCT No.: PCT/US2020/024032
§ 371 (c)(1),
(2) Date: Sep. 16, 2021

(87) PCT Pub. No.: WO2020/198066
PCT Pub. Date: Oct. 1, 2020

(65) Prior Publication Data

US 2022/0175763 A1 Jun. 9, 2022

Related U.S. Application Data

(60) Provisional application No. 62/822,173, filed on Mar. 22, 2019.

(51) Int. Cl.

| | |
|---|---|
| ***A61K 31/4745*** | (2006.01) |
| ***A61K 31/4704*** | (2006.01) |
| ***A61K 45/06*** | (2006.01) |
| ***A61P 35/00*** | (2006.01) |
| ***C07K 16/28*** | (2006.01) |

(52) U.S. Cl.
CPC .......... *A61K 31/4745* (2013.01); *A61K 45/06* (2013.01); *A61P 35/00* (2018.01); *C07K 16/2818* (2013.01)

(58) Field of Classification Search
CPC ............ A61K 31/4745; A61K 31/4704; A61K 45/06; A61K 39/3955; A61K 2300/00; A61P 35/00; C07K 16/2818
See application file for complete search history.

(56) References Cited

U.S. PATENT DOCUMENTS

| | | | |
|---|---|---|---|
| 5,811,097 | A | 9/1998 | Allison et al. |
| 5,855,887 | A | 1/1999 | Allison et al. |
| 5,977,318 | A | 11/1999 | Linsley et al. |
| 6,051,227 | A | 4/2000 | Allison et al. |
| 6,207,156 | B1 | 3/2001 | Kuchroo et al. |
| 6,682,736 | B1 | 1/2004 | Hanson et al. |
| 6,984,720 | B1 | 1/2006 | Korman et al. |
| 7,109,003 | B2 | 9/2006 | Hanson et al. |
| 7,132,281 | B2 | 11/2006 | Hanson et al. |
| 2002/0039581 | A1 | 4/2002 | Carreno et al. |
| 2002/0086014 | A1 | 7/2002 | Korman et al. |
| 2005/0201994 | A1 | 9/2005 | Korman et al. |

FOREIGN PATENT DOCUMENTS

| | | |
|---|---|---|
| EP | 1212422 | 6/2000 |
| WO | 1998/042752 | 1/1998 |
| WO | 2000/037504 | 6/2000 |
| WO | 2001/014424 | 3/2001 |
| WO | 2004/035607 | 4/2004 |
| WO | 2017013436 A1 | 1/2017 |
| WO | 2019025440 A1 | 2/2019 |

OTHER PUBLICATIONS

International Search Report mailed Aug. 17, 2020 for corresponding International Patent Application No. PCT/US2020/024032.
Sato et al., DNA double-strand break repair pathway regulates PD-L1 expression in cancer cells, Nature Communications, Nov. 24, 2017, vol. 8, p. 1751.
Alam TI, et al. (2003 Human mitochondrial DNA is packaged with TFAM. Nucleic Acids Res. 31(6):1640-1645.
Barlaam B, et al. (2018) Discovery of a Series of 3-Cinnoline Carboxamides as Orally Bioavailable, Highly Potent, and Selective ATM Inhibitors. ACS Med Chem Lett. 9(8):809-814.
Bonneville R, et al. (2017) Landscape of Microsatellite Instability Across 39 Cancer Types. JCO Precis Oncol. 2017:2017:PO.17.00073.
Camacho LH, et al. (2004) Phase 1 clinical trial of anti-CTLA4 human monoclonal antibody CP-675,206 in patients (pts) with advanced solid malignancies. JCO. 22:2505-2505.
Chen Q, et al. (2016) Regulation and function of the cGAS-STING pathway of cytosolic DNA sensing. Nat Immunol. (10):1142-1149.
Dietel M, et al. (2019) Real-world prevalence of programmed death ligand 1 expression in locally advanced or metastatic non-small-cell lung cancer: The global, multicenter EXPRESS study. Lung Cancer. 134:174-179.
Dobin A, et al. (2013) STAR: ultrafast universal RNA-seq aligner. Bioinformatics. 29(1):15-21.
Durant ST, et al. (2018) The brain-penetrant clinical ATM inhibitor AZD1390 radiosensitizes and improves survival of preclinical brain tumor models. Sci Adv. 4(6):1719.
Ekstrand MI, et al. (2004) Mitochondrial transcription factor A regulates mtDNA copy number in mammals. Hum Mol Genet. 13(9):935-944.
Frankish A, et al. (2019) GENCODE reference annotation for the human and mouse genomes. Nucleic Acids Res. 47 (D1):D766-D773.

(Continued)

*Primary Examiner* — Sun Jae Yoo
(74) *Attorney, Agent, or Firm* — POLSINELLI PC

(57) ABSTRACT

The present disclosure provides, in part, compositions and methods for enhancing the efficacy of immune checkpoint blockade therapy in a subject. Methods for identifying subjects that are appropriate for immune checkpoint blockade therapy are also provided.

26 Claims, 71 Drawing Sheets

Specification includes a Sequence Listing.

(56) References Cited

OTHER PUBLICATIONS

Hartlova A, et al. (2015) DNA damage primes the type I interferon system via the cytosolic DNA sensor STING to promote anti-microbial innate immunity. Immunity. 42(2):332-343.
Hurwitz AA, et al. (1998) CTLA-4 blockade synergizes with tumor-derived granulocyte-macrophage colony-stimulating factor for treatment of an experimental mammary carcinoma. Proc Natl Acad Sci USA. 95(17):10067-10071.
Kawai T, et al. (2005) IPS-1, an adaptor triggering RIG-I-and Mda5-mediated type I interferon induction. Nat Immunol. 6(10):981-988.
Li H, et al. (2009) 1000 Genome Project Data Processing Subgroup. The Sequence Alignment/Map format and SAMtools. Bioinformatics. 25(16):2078-2079.
Love MI, et al. (2014) Moderated estimation of fold change and dispersion for RNA-seq data with DESeq2. Genome Biol. 15(12):550.
Martin M. (2011) Cutadapt removes adapter sequences from high-throughput sequencing reads. EMBnet.journal, [S.I.], 17(1):10-12.
Mokyr MB, et al. (1998) Realization of the therapeutic potential of CTLA-4 blockade in low-dose chemotherapy-treated tumor-bearing mice. Cancer Res. 58(23):5301-5304.
Mootha VK, et al. (2003) PGC-1alpha-responsive genes involved in oxidative phosphorylation are coordinately downregulated in human diabetes. Nat Genet. 34(3):267-273.
Petersen AJ, et al. (2012) ATM kinase inhibition in glial cells activates the innate immune response and causes neurodegeneration in Drosophila. Proc Natl Acad Sci U S A. 109(11):E656-664.
Samstein RM, et al. (2019) Tumor mutational load predicts survival after immunotherapy across multiple cancer types. Nat Genet. 51(2):202-206.
Sun L, et al. (2013) Cyclic GMP-AMP synthase is a cytosolic DNA sensor that activates the type I interferon pathway. Science. 339(6121):786-791.
Taube JM, et al. (2014) Association of PD-1, PD-1 ligands, and other features of the tumor immune microenvironment with response to anti-PD-1 therapy. Clin Cancer Res. 20(19):5064-5074.
Topalian SL, et al. (2015) Immune checkpoint blockade: a common denominator approach to cancer therapy. Cancer Cell. 27(4):450-461.
Valentin-Vega YA, et al. (2012) Mitochondrial dysfunction in ataxia-telangiectasia. Blood. 119(6):1490-1500.
Wang H, et al. (2017) cGAS is essential for the antitumor effect of immune checkpoint blockade. Proc Natl Acad Sci USA. 114(7):1637-1642.
White MJ, et al. (2014) Apoptotic caspases suppress mtDNA-induced STING-mediated type I IFN production. Cell. 159(7):1549-1562.
Wu J, et al. (2013) Cyclic GMP-AMP is an endogenous second messenger in innate immune signaling by cytosolic DNA. Science. 339(6121):826-830.
Zehir A, et al. (2017) Mutational landscape of metastatic cancer revealed from prospective clinical sequencing of 10,000 patients. Nat Med. 23(6):703-713.

| Number at risk | | | | | | Median |
|---|---|---|---|---|---|---|
| | 105 | 34 | 9 | 3 | 2 | 40 |
| WT | 1556 | 395 | 75 | 13 | 0 | 17 |

| Number at risk | | | | | | Median |
|---|---|---|---|---|---|---|
| | 23 | 14 | 8 | 5 | 1 | NA |
| WT | 192 | 79 | 31 | 12 | 5 | 15 |

SEQUENCE LISTING

<160> NUMBER OF SEQ ID NOS: 38

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ttgtttcagg atctcgaatc 20

<210> SEQ ID NO 2
<211> LENGTH: 20
<212> TYPE: DNA
<213> ORGANISM: Artificial Sequence -continued
<220> FEATURE:
<223> OTHER INFORMATION: Synthetic oligonucleotide

<400> SEQUENCE: 2
gatgcaggaa atcagtagtt 20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
ctctgtcatg ctctaactgc 20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ctgtttcagg atcctgaatc 20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
acgggggtcg agatgtgcgc 20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
taccagcgtg ggaactccgg 20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
cagaatgcag aaacgggagt 20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
tgccgtttag acccttcgag 20

-continued

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
cttctcgcta caacacatga 20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
ggcagggatt caggcaccat 20

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
gaaatcgtgc gtgacatcaa a 21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
tgtagtttca tggatgccac a 21

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
ctggcttcca tcatgaacaa 20

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 14
agagggctgt ggtggagaa 19

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
ggatgtgacc ttcctcagac tc 22

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
accttctcct gcgggaatcc aa 22

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
caagtgctcc aatcttgcag tc 22

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ttctctgggt tggcacacac 20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
caaggcaggt ttctgaggag 20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gacctggtca ccatcagcat 20

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
ctagagctag agcctgcag 19

<210> SEQ ID NO 22

<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 22
agttagtcac ggacaccag 19

<210> SEQ ID NO 23
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 23
aatctaccat cctccgtgaa acc 23

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
tcagtttagc tacccccaag tttaa 25

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 25
cccttcccca tttggtct 18

<210> SEQ ID NO 26
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 26
tggtttcacg gaggatgg 18

<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 27
tcctccgtga aaccaacaa 19

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 28
agcgagaaga ggggcatt 18

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
gctttccact tcatcttacc attta 25

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
tgttgggttg tttgatcctg 20

<210> SEQ ID NO 31
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 31
cactgcctgc ccagtga 17

<210> SEQ ID NO 32
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 32
ataccgcggc cgttaaa 17

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 33
aacggatcca cagccgta 18

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 34
agtcctcggg ccatgatt 18

<210> SEQ ID NO 35
<211> LENGTH: 20
<212> TYPE: DNA

-continued

```
<213> ORGANISM: Artificial Sequence
<220> FEATURE:
<223> OTHER INFORMATION: Synthetic oligonucleotide

<400> SEQUENCE: 35

gccccagata tagcattccc                                              20


<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36

gttcatcctg ttcctgctcc                                              20


<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 37

ctagctcatg tgtcaagacc ctctt                                        25


<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38

gccagcacgt ttctctcgtt                                              20
```

COMPOSITIONS AND METHODS FOR ENHANCING CANCER IMMUNE CHECKPOINT THERAPY

CROSS-REFERENCE TO RELATED APPLICATIONS

This application is U.S. national phase application under 35 U.S.C. § 371 of International Application No. PCT/US2020/024032, filed on Mar. 20, 2020, which claims benefit under 35 U.S.C. 119 of the U.S. Provisional Patent Application No. 62/822,173, filed Mar. 22, 2019, each of which applications are incorporated by reference in their entirety.

STATEMENT REGARDING FEDERALLY SPONSORED RESEARCH OR DEVELOPMENT

This invention was made with Government support under Federal Grant no. CA208852 awarded by the National Cancer Institute (NCI). The Federal Government has certain rights to this invention.

FIELD OF THE INVENTION

The present invention relates to methods and compositions for enhanced cancer immunotherapy.

INCORPORATION BY REFERENCE OF SEQUENCE LISTING PROVIDED ELECTRONICALLY

This application contains a Sequence Listing submitted on 16 Sep. 2021 as an electronic .txt file named "20-419-WO_Sequence_Listing_ST25", having a size of 7433 bytes and created on 16 Sep. 2021. The information contained in this electronic.txt file is incorporated herein by reference in its entirety.

BACKGROUND OF THE INVENTION

The great enthusiasm for immune checkpoint blockade therapy (ICB; immune checkpoint inhibitor therapy) is justified by the spectacular, durable successes it has had in some previously difficult to treat cancers such as melanoma and lung cancer. However, despite the successes, ICB therapy still only benefits a minority of cancer patients, and many patients suffer from undesirable side effects despite not being able to benefit from ICB treatment. Therefore, novel approaches are needed to identify those patients who can benefit from ICB treatment. Further, there is a need for new compositions and methods for enhancing the effectiveness of ICB therapy to be more effective on a wider range of cancers and/or subjects.

SUMMARY OF THE INVENTION

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is based, in part, on the findings by the inventors that cancer immune checkpoint therapy can be enhanced by activating the cGAS/STING pathway of cellular innate immunity. In some embodiments, activation of the cGAS/STING pathway comprises inhibiting the kinase activity of Ataxia Telangiectasia Mutated (ATM) protein.

Accordingly, one aspect of the present disclosure provides a method of enhancing immune checkpoint inhibitor therapy (or immune checkpoint blockade (ICB) therapy; used interchangeably herein) in a subject suffering from a cancer, the method comprising, consisting of, or consisting essentially of administering to the subject a therapeutically effective amount of at least one ATM inhibitor and at least one immune checkpoint inhibitor such that the activity of the cancer immune checkpoint inhibitor is enhanced.

Another aspect of the present disclosure provides a method of treating cancer in a subject, the method comprising, consisting of, or consisting essentially of administering to the subject a therapeutically effective amount of at least one ATM inhibitor and at least one immune checkpoint inhibitor such that the cancer is treated in the subject.

In some embodiments, the at least one ATM inhibitor activates the cGAS/STING pathway of innate cellular immunity. In some embodiments, the at least one ATM inhibitor increases lymphocyte infiltration into the tumor microenvironment. In some embodiments, the at least one ATM inhibitor stimulates CD8+ T cell infiltration into the tumor microenvironment. In some embodiments, the at least one ATM inhibitor stimulates CD4+ T cell infiltration into the tumor microenvironment. In some embodiments, the at least one ATM inhibitor inhibits cancer cell growth. In some embodiments, the at least one ATM inhibitor stimulates mitochondrial DNA release in a subject. In some embodiments, the at least one ATM inhibitor stimulates natural killer (NK) cell infiltration into a tumor microenvironment in a subject. In some embodiments, the at least one ATM inhibitor inhibits mitochondrial transcription factor A (TFAM) in a subject. In some embodiments, the at least one ATM inhibitor activates an innate interferon response in a subject.

In some embodiments, the at least one ATM inhibitor comprises a small molecule. In one embodiment, the ATM inhibitor is selected from the group consisting of KU-55933, KU-60019, KU-559403, NVP-BEZ235, AZD1390, AZD156, AZ31, AZ32, M3541 (also referred to as Merck KGA), Compound 12 and any salts, esters, and derivatives thereof, Compound 21 and any salts, esters, and derivatives thereof, N,N-Dimethyl-3-[[5-(3-Methyl-2-Oxo-1-Tetrahydropyran-4-YL-Imidazo[4,5-C]Quinolin-8-YL)-2-Pyridyl]Oxy]Propan-1-amine Oxide, CP-466722, CGK733, siRNAs against the human ATM gene, shRNAs against the human ATM gene, sgRNAs against the human ATM gene, and combinations thereof.

In some embodiments, the at least one immune checkpoint inhibitor is a therapy selected from the group consisting of an anti-PD1 therapy, an anti-PD-L1 therapy, an anti-CTLA-4 therapy and combinations thereof.

In one embodiment, the anti-CTLA4 therapy is selected from the group consisting of ipilimumab, tremelimumab, an anti-CTLA-4 antibody, and combinations thereof.

In another embodiment, the anti-PD1 therapy is selected from the group consisting of nivolumab, pembrolizumab, pidilizumab, MEDI0680, Libtayo (cemiplimab), M7824 (MSB0011395C) (PDL1 and TGF-beta dual inhibiting antibody), Infinzi (durvaluma), Bavencio (avelumab), Toripalimab, Tyvyt, camrelizumab, Tislelizumab and anti-PD1 antibody, and combinations thereof.

In yet another embodiment, the anti-PD-L1 therapy is selected from the group consisting of atezolizumab, BMS-936559, MEDI4736, MSB0010718C, an anti-PD-L1 antibody, and combinations thereof.

In one embodiment, the at least one ATM inhibitor is administered prior to the administration of the at least one immune checkpoint inhibitor. In another embodiment, the at least one ATM inhibitor and the at least one immune checkpoint inhibitors are administered concurrently. In yet another embodiment, the at least one ATM inhibitor is administered after the at least one immune checkpoint inhibitor.

In another embodiment, the cancer comprises a solid tumor. In other embodiments, the cancer comprises a non-solid tumor. In some embodiments, the cancer is selected from the group consisting of bladder cancer, colorectal cancer, melanoma, non-small cell lung cancer, esophageal/gastric cancer, breast cancer, glioma, renal cell carcinoma, head and neck cancer, small bowel cancer, non-melanoma skin cancer, endometrial cancer, hepatobiliary cancer, mature B-cell neoplasms, appendiceal cancer, small cell lung cancer, prostate cancer, histiocytosis, salivary gland cancer, thyroid cancer, adrenocortical carcinoma, mature T and NK neoplasms, pancreatic cancer, soft tissue carcinoma, peripheral nervous system cancer, germ cell tumor, ovarian cancer, uterine sarcoma, mesothelioma, bone cancer, gastrointestinal stromal tumor. brain tumors, neuroblastoma, cervical cancer, colon cancer, stomach cancer, intestine cancer, liver cancer, biliary cancer, AML, Hodgkin's lymphoma, Non-Hodgkin's lymphoma, sarcoma, and combinations thereof.

In some embodiments, the at least one ATM inhibitor and the at least one immune checkpoint inhibitor (the "treatment") is administered intravenously. In some embodiments, the at least one ATM inhibitor and the at least one immune checkpoint inhibitor treatment are administered orally. In some embodiments, either the at least one ATM inhibitor or the at least one immune checkpoint inhibitor treatment is administered intravenously and other is administered orally.

In some embodiments, the methods further comprise administering to the subject one or more additional agents to the subject. In some embodiments, the one or more additional agent comprises a chemotherapeutic agent. In some embodiments, the chemotherapeutic agent is selected from the group consisting of taxol, doxorubicin, irinotecan temozolomide, and combinations thereof. In another embodiment, the one or more additional agent comprises radiation/radiotherapy. In some embodiments, the one or more additional agents comprises both a chemotherapeutic agent and radiation/radiotherapy. In some embodiments wherein the one or more additional agents comprises both a chemotherapeutic agent and radiation/radiotherapy, the chemotherapeutic agent is selected from the group consisting of taxol, doxorubicin, irinotecan temozolomide, and combinations thereof.

Another aspect of the present disclosure provides a method for identifying a subject with a cancer that is suitable for immune checkpoint inhibitor therapy, the method comprising obtaining a sample from the subject with cancer, assaying for a mutation in ATM, wherein when a mutation is detected, the subject is suitable for immune checkpoint inhibitor therapy. In some embodiments, the ATM mutation is a nonsense mutation.

Another aspect of the present disclosure provides a pharmaceutical composition comprising, consisting of, or consisting essentially of a therapeutically effective amount of at least one ATM inhibitor, a therapeutically effective amount of an immune checkpoint inhibitor, and a pharmaceutically acceptable carrier/excipient.

In some embodiments, the ATM inhibitor is selected from the group consisting of KU-55933, KU-60019, KU-559403, NVP-BEZ235, AZD1390, AZD156, AZ31, AZ32, M3541 (also referred to as Merck KGA), Compound 12, Compound 21, N,N-Dimethyl-3-[[5-(3-Methyl-2-Oxo-1-Tetrahydropyran-4-YL-Imidazo[4,5-C]Quinolin-8-YL)-2-Pyridyl]Oxy]Propan-1-amine Oxide, CP-466722, CGK733 and combinations thereof.

In some embodiments, the immune checkpoint inhibitor is a therapy selected from the group consisting of an anti-PD1 therapy, an anti-PD-L1 therapy, an anti-CTLA-4 therapy and combinations thereof.

In one embodiment, the anti-CTLA4 therapy is selected from the group consisting of ipilimumab, tremelimumab, an anti-CTLA-4 antibody, and combinations thereof.

In another embodiment, the anti-PD1 therapy is selected from the group consisting of nivolumab, pembrolizumab, pidilizumab, MEDI0680, Libtayo (cemiplimab), M7824 (MSB0011395C) (PDL1 and TGF-beta dual inhibiting antibody), Infinzi (durvaluma), Bavencio (avelumab), Toripalimab, Tyvyt, camrelizumab, Tislelizumab and anti-PD1 antibody, and combinations thereof.

In yet another embodiment, the anti-PD-L1 therapy is selected from the group consisting of atezolizumab, BMS-936559, MEDI4736, MSB0010718C, an anti-PD-L1 antibody, and combinations thereof.

Another aspect of the present disclosure provides all that is described and illustrated herein.

These and other features and provisions and advantages of the present invention will be more fully understood from the following detailed description of the invention taken together with the accompanying claims. It is noted that the scope of the claims is defined by the recitations therein and not by the specific discussion of features and advantages set forth in the present invention.

INCORPORATION BY REFERENCE

All publications and patent applications mentioned in this specification are hereby incorporated by reference herein to the same extent as if each individual publication or patent application was specifically and individually indicated to be incorporated by reference.

BRIEF DESCRIPTION OF THE DRAWINGS

The foregoing aspects and other features of the disclosure are explained in the following description, taken in connection with the accompanying drawings, herein:

FIGS. 65-66 present additional human clinical data regarding the influence of ATM mutations on tumor responses to ICB therapy.

FIGS. 67-73 present additional data on tumor responses to ATM inhibition and PD-1 blockade in mouse tumors.

FIGS. 74-81 present Additional data on lymphocyte infiltration into ATM deficient tumors.

FIGS. 82-87 show RNAseq profiling of ATM deficient tumors in vivo and ATM deficient 4T1 cells in vitro.

FIGS. 95-98 show that ATM deficiency mediates ISG activation and tumor growth delays through cGAS/STING pathway not MDA5.

DETAILED DESCRIPTION OF THE INVENTION

Figure 1:
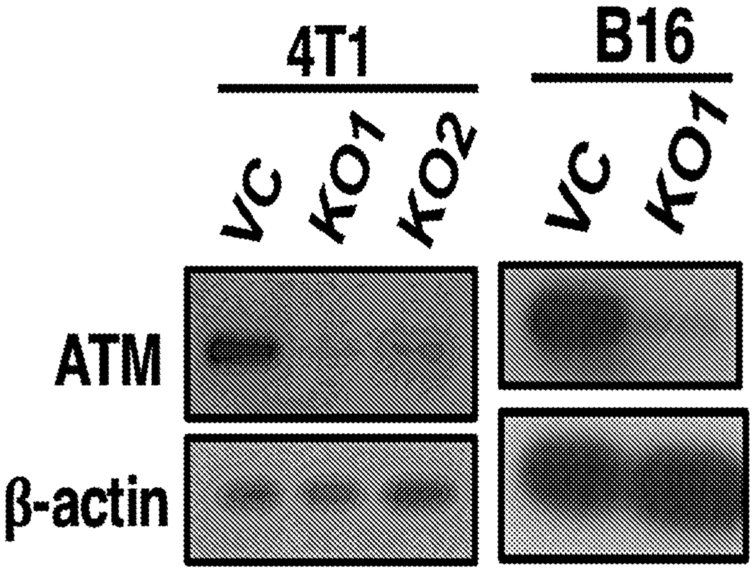
FIG. 1 presents Western blot images showing the successful knockout of ATM in 4T1 and B16F10 murine tumor cells in accordance with one embodiment of the present disclosure.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human. In certain embodiments, the subject comprises a human suffering from cancer.

The term "cancer" as used herein refers to diseases caused by uncontrolled cell division and the ability of cells to metastasize, or to establish new growth in additional sites. The terms "malignant," "malignancy," "neoplasm," "tumor," and variations thereof refer to cancerous cells or groups of cancerous cells. A cancer according to the present disclosure may comprise a solid tumor or non-tumor (e.g., "liquid") cancer. Suitable examples include, but are not limited to, bladder cancer, colorectal cancer, melanoma, non-small cell lung cancer, esophageal/gastric cancer, breast cancer, glioma, renal cell carcinoma, head and neck cancer, small bowel cancer, non-melanoma skin cancer, endometrial cancer, hepatobiliary cancer, mature B-cell neoplasms, appendiceal cancer, small cell lung cancer, prostate cancer, histiocytosis, salivary gland cancer, thyroid cancer, adrenocortical carcinoma, mature T and NK neoplasms, pancreatic cancer, soft tissue carcinoma, peripheral nervous system cancer, germ cell tumor, ovarian cancer, uterine sarcoma, mesothelioma, bone cancer, gastrointestinal stromal tumor. brain tumors, neuroblastoma, cervical cancer, colon cancer, stomach cancer, intestine cancer, liver cancer, biliary cancer, AML, Hodgkin's lymphoma, Non-Hodgkin's lymphoma, sarcoma, and combinations thereof.

Unless otherwise defined, all technical terms used herein have the same meaning as commonly understood by one of ordinary skill in the art to which this disclosure belongs.

A. Methods of Use

The present disclosure, is based in part, on research performed by the inventors examining the role of ATM on tumor growth in immunocompetent mouse models. We generated ATM-deficient murine tumor cells and evaluated their tumor-forming abilities and response to immune checkpoint therapy. Our data indicate that ATM deletion completely inhibits or severely attenuates tumor formation in syngeneic mouse models in the absence of radiotherapy. Moreover, ATM inhibition overcomes resistance to anti-PD1 immune checkpoint therapy in the majority of cases. In addition, ATM-deficiency leads to significant infiltration of T cells and other immune effector cells. At the mechanistic level, we show that ATM inhibition leads to the significant activation of the cGAS/Sting pathway, which in turn activates cellular interferon response and stimulates immune cell infiltrate in the tumors. Furthermore, we show that the cGAS/STING pathway appears to be essential for ATM deficiency-induced tumor suppression. Accordingly, while not desiring to be bound by theory, the data presented herein indicate that inhibition of ATM expression and/or function may be useful to activate anti-tumor immunity, particularly in combination with immune checkpoint inhibitors and/or immune checkpoint inhibitors therapy.

Accordingly, one aspect of the present disclosure provides a method of enhancing immune checkpoint inhibitor therapy in a subject suffering from a cancer, the method comprising, consisting of, or consisting essentially of administering to the subject a therapeutically effective amount of at least one ATM inhibitor and at least one immune checkpoint inhibitor such that the activity of the cancer immune checkpoint inhibitor is enhanced.

Another aspect of the present disclosure provides a method of treating cancer in a subject, the method comprising, consisting of, or consisting essentially of administering to the subject a therapeutically effective amount of at least one ATM inhibitor and at least one immune checkpoint inhibitor such that the cancer is treated in the subject.

In some embodiments, the at least one ATM inhibitor activates the cGAS/STING pathway of innate cellular immunity. In some embodiments, the at least one ATM inhibitor increases lymphocyte infiltration into the tumor microenvironment. In some embodiments, the at least one ATM inhibitor stimulates CD8+ T cell infiltration into the tumor microenvironment. In some embodiments, the at least one ATM inhibitor stimulates CD4+ T cell infiltration into the tumor microenvironment. In some embodiments, the at least one ATM inhibitor inhibits cancer cell growth. In some embodiments, the at least one ATM inhibitor stimulates mitochondrial DNA release in a subject. In some embodiments, the at least one ATM inhibitor stimulates natural killer (NK) cell infiltration into a tumor microenvironment in a subject. In some embodiments, the at least one ATM inhibitor inhibits mitochondrial transcription factor A (TFAM) in a subject. In some embodiments, the at least one ATM inhibitor activates an innate interferon response in a subject.

Suitable ATM inhibitors include any compound, small molecule, antibody, drug, and the like. In some embodiments, the at least one ATM inhibitor comprises a small molecule. Suitable examples include, but are not limited to, KU-55933, KU-60019, KU-559403, NVP-BEZ235, AZD1390, AZD156, AZ31, AZ32, M3541 (also referred to as Merck KGA), N,N-Dimethyl-3-[[5-(3-Methyl-2-Oxo-1-Tetrahydropyran-4-YL-Imidazo[4,5-C]Quinolin-8-YL)-2-Pyridyl]Oxy]Propan-1-amine Oxide, CP-466722, and CGK733. Also included are the compounds found in Barlaam, B. et al. 2018 *ACS Med. Chem. Letts,* 9:809-814, and in certain embodiments the following compounds having the following formula:

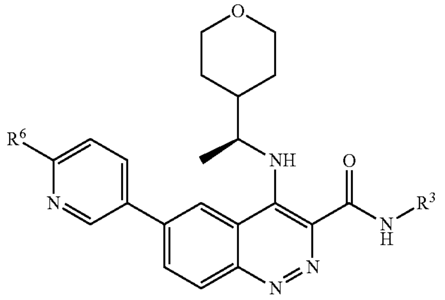

wherein $R_3$ comprises an H and $R_6$ comprises $OCH_2CH_2CH_2NMe_2$, and any salts, esters, and derivatives thereof (herein termed Compound 12); and

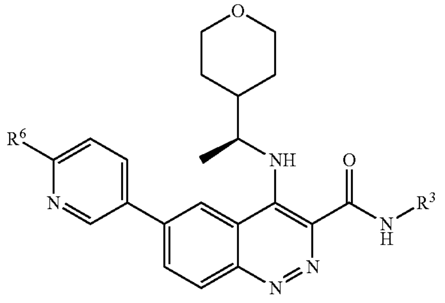

wherein $R_3$ comprises an Me and $R_6$ comprises $OCH_2CH_2CH_2NMe_2$, and any salts, esters, and derivatives thereof (herein termed Compound 21). Other suitable inhibitors of ATM include siRNAs or shRNAs against the human ATM gene that can deplete the mRNA levels of ATM in cancer cells and sgRNA against the human ATM gene and delivered into cancer cells in combination with the bacterial Cas genes (e.g. Cas9 or Cpf1) with viral or non-viral approaches.

Immune checkpoint inhibitors include agents that inhibit CTLA-4, PD-1, PD-L1, and the like. Suitable anti-CTLA-4 therapy agents for use in the methods of the disclosure, include, without limitation, anti-CTLA-4 antibodies, human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, ipilimumab, tremelimumab, anti-CD28 antibodies, anti-CTLA-4 adnectins, anti-CTLA-4 domain antibodies, single chain anti-CTLA-4 fragments, heavy chain anti-CTLA-4 fragments, light chain anti-CTLA-4 fragments, inhibitors of CTLA-4 that agonize the co-stimulatory pathway, the antibodies disclosed in PCT Publication No. WO 2001/014424, the antibodies disclosed in PCT Publication No. WO 2004/035607, the antibodies disclosed in U.S. Publication No. 2005/0201994, and the antibodies disclosed in granted European Patent No. EP1212422B1. Additional anti-CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. 2002/0039581 and 2002/086014. Other anti-CTLA-4 antibodies that can be used in a method of the present disclousre include, for example, those disclosed in: WO 98/42752; U.S. Pat. Nos. 6,682,736 and 6,207,156; Hurwitz et al., *Proc. Natl. Acad. Sci. USA,* 95(17):10067-10071 (1998); Camacho et al., *J. Clin. Oncology,* 22(145): Abstract No. 2505 (2004) (antibody CP-675206); Mokyr et al., *Cancer Res,* 58:5301-5304 (1998), U.S. Pat. Nos. 5,977,318, 6,682,736, 7,109,003, and 7,132,281.

Suitable anti-PD-1 and anti-PD-L1 therapy agents for use in the methods of the invention, include, without limitation, anti-PD-1 and anti-PD-L1 antibodies, human anti-PD-1 and anti-PD-L1 and anti-PD-L1 antibodies, mouse anti-PD-1 and anti-PD-L1 antibodies, mammalian anti-PD-1 and anti-PD-L1 antibodies, humanized anti-PD-1 and anti-PD-L1 antibodies, monoclonal anti-PD-1 and anti-PD-L1 antibodies, polyclonal anti-PD-1 and anti-PD-L1 antibodies, chimeric anti-PD-1 and anti-PD-L1 antibodies. In specific embodiments, anti-PD-1 therapy agents include nivolumab, pembrolizumab, pidilizumab, MEDI0680, and combinations thereof. In other specific embodiments, anti-PD-L1 therapy agents include atezolizumab, BMS-936559, MEDI4736, MSB0010718C, and combinations thereof.

Suitable anti-PD-1 and anti-PD-L1 antibodies are described in Topalian, et al., Immune Checkpoint Blockade: A Common Denominator Approach to Cancer Therapy, Cancer *Cell* 27: 450-61 (Apr. 13, 2015), incorporated herein by reference in its entirety.

Combination treatments involving one or more ATM inhibitors and one or more immune checkpoint inhibitors can be achieved by administering the ATM inhibitor(s) and the immune checkpoint inhibitor(s) at the same time. Such combination treatments can be achieved by administering a single composition or pharmacological formulation that includes both agents, or by administering two distinct compositions or formulations, at the same time, wherein one composition includes the ATM inhibitor and the other includes the immune checkpoint inhibitor.

Alternatively, treatment with the ATM inhibitor(s) can precede or follow treatment with the immune checkpoint inhibitor(s) by intervals ranging from minutes to weeks. In embodiments where the immune checkpoint inhibitor(s) and ATM inhibitor(s) are administered separately, one would generally ensure that a significant period of time did not expire between the time of each delivery, such that the immune checkpoint inhibitor and ATM inhibitor treatment would still be able to exert an advantageously combined effect. In such instances, it is provided that one would contact the cell (and/or administer to the subject) with both modalities within about 12-24 hours of each other and, optionally, within about 6-12 hours of each other. In some situations, it can be desirable to extend the time period for treatment significantly, however, where several days (2, 3, 4, 5, 6 or 7) to several weeks (1, 2, 3, 4, 5, 6, 7 or 8) lapse between the respective administrations. Also, under some circumstances, more than one administration of either the ATM inhibitor(s) or of the immune checkpoint inhibitor(s) will be desired.

In one embodiment, a method of treating cancer is provided, the method comprising administering to a subject in need thereof a therapeutically effective amount of one or more ATM inhibitor; and (2) one or more immune checkpoint inhibitor such that the cancer is treated in the subject.

In another embodiment, a method of enhancing the effectiveness of an immune checkpoint inhibitor in a subject suffering from a cancer, the method comprising, consisting of, or consisting essentially of administering to the subject a therapeutically effective amount of one or more ATM inhibitors and one or more immune checkpoint inhibitors such that the activity of the one or more cancer immune checkpoint inhibitors is enhanced.

In some embodiments, the one or more immune checkpoint inhibitors is an anti-CTLA-4 antibody selected from the group consisting of ipilimumab, tremelimumab, and combinations thereof. In a specific embodiment, the immune checkpoint inhibitor is ipilimumab.

In another embodiment, the one or more immune checkpoint inhibitors is an anti-PD-1 antibody selected from the group consisting of nivolumab, pembrolizumab, pidilizumab, MEDI0680, and combinations thereof. In another embodiment, the one or more immune checkpoint inhibitor is an anti-PD-L1 antibody selected from the group consisting of atezolizumab, BMS-936559, MEDI4736, MSB0010718C, and combinations thereof.

In still another embodiment, the one or more ATM inhibitors is administered with one or more immune checkpoint inhibitors selected from the group consisting of ipilimumab, tremelimumab, nivolumab, pembrolizumab, pidilizumab, MEDI0680, atezolizumab, BMS-936559, MEDI4736, MSB0010718C, and combinations thereof.

In another embodiment, a method of stimulating anti-tumor immunity in a subject in need thereof is provided, comprising administering to the subject a therapeutically effective amount of one or more ATM inhibitors. In some embodiments, the method further comprises administering an effective amount of one or more immune checkpoint inhibitors. In some embodiments, the one or more immune checkpoint inhibitors is an anti-CTLA-4 antibody. In other embodiments, the one or more immune checkpoint inhibitors is one or more selected from the group consisting of ipilimumab, tremelimumab, nivolumab, pembrolizumab, pidilizumab, MEDI0680, atezolizumab, BMS-936559, MEDI4736, MSB0010718C, and combinations thereof.

Also provided is a method of increasing the activity of an immune checkpoint inhibitor comprising administering to a subject in need thereof synergistic, therapeutically effective amount of one or more ATM inhibitors and (2) one or more immune checkpoint inhibitors. In certain embodiments, the one or more immune checkpoint inhibitors is an anti-CTLA-4 therapy selected from the group consisting of ipilimumab, tremelimumab, and combinations thereof. In a specific embodiment, the immune checkpoint inhibitor is ipilimumab. In another embodiment, the one or more immune checkpoint inhibitors is an anti-PD-1 therapy selected from the group consisting of nivolumab, pembrolizumab, pidilizumab, MEDI0680, and combinations thereof. In still another embodiment, the one or more immune checkpoint inhibitor is an anti-PD-L1 therapy selected from the group consisting of atezolizumab, BMS-936559, MEDI4736, MSB0010718C, and combinations thereof. In still another embodiment, the one or more ATM inhibitors is administered with one or more immune checkpoint inhibitors selected from the group consisting of ipilimumab, tremelimumab, nivolumab, pembrolizumab, pidilizumab, MEDI0680, atezolizumab, BMS-936559, MEDI4736, MSB0010718C, and combinations thereof.

Also provided herein is a method of immunotherapy comprising administering to a subject in need thereof a therapeutically effective amount of one or more ATM inhibitors. As with previous methods described herein, the one or more ATM inhibitors is optionally administered together with one or more immune checkpoint inhibitors, such as anti-CTLA-4, anti-PD-1, anti-PD-L1, and combinations thereof. In certain embodiments, the one or more ATM inhibitors is administered with one or more immune checkpoint inhibitors selected from the group consisting of ipilimumab, tremelimumab, nivolumab, pembrolizumab, pidilizumab, MEDI0680, atezolizumab, BMS-936559, MEDI4736, MSB0010718C, and combinations thereof.

In any of the methods according to the present disclosure, the one or more ATM inhibitors and/or one or more immune checkpoint inhibitors can be further co-administered or administered in combination with any other agent (or agents, e.g. one or more agents) useful for preventing or treating a cancer in a subject that does not attenuate or abolish the effect of the one or more ATM inhibitors or one or more immune checkpoint inhibitors. In any of the methods according to the present disclosure, the agent useful for preventing and/or treating the cancer includes, but is not limited to vaccines, antigens, antibodies, cytotoxic agents, chemotherapeutic agents, radiation/radiation therapy, allergens, antibiotics, antisense oligonucleotides, kinase inhibitors, TLR agonists, peptides, proteins, gene therapy vectors, DNA vaccines and/or adjuvants to enhance the specificity or magnitude of the immune response, or co-stimulatory molecules such as cytokines, chemokines, protein ligands, trans-activating factors, peptides, and peptides comprising modified amino acids. In some embodiments, the additional agent comprises a chemotherapeutic agent. Suitable chemotherapeutic agents include, but are not limited to, Gemcitabine methotrexate, vincristine, adriamycin, cisplatin, non-sugar containing chloroethylnitrosoureas, 5-fluorouracil, mitomycin C, bleomycin, doxorubicin, dacarbazine, fragyline, Meglamine GLA, valrubicin, carmustaine and poliferposan, MMI270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, NOVANTRONE®/Mitroxantrone, Metaret/Suramin, Batimastat, E7070, BCH-4556, CS-682, 9-AC, AG3340, AG3433, Incel NX-710, VX-853, ZD0101, IS1641, ODN 698, TA 2516/Marmistat, BB2516/Marmistat, CDP 845, D2163, PD183805, DX8951f, Lemonal DP 2202, FK 317, imatinib mesylate/GLEEVEC®, Picibanil/OK-432, AD 32/Valrubicin, METASTRON®/strontium derivative, Temodal/Temozolomide, Evacet/liposomal doxorubicin, Yewtaxan/Placlitaxel, TAXOL®/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT® (Tegafur/Uracil), ERGAMISOL®/Levamisole, Eniluracil/776C85/5FU enhancer, Campto/Levamisole, CAMPTOSAR®/Irinotecan, Tumodex/Ralitrexed, LEUSTATIN®/Cladribine, Paxex/Paclitaxel, DOXIL®/liposomal doxorubicin, Caelyx/liposomal doxorubicin, FLUDARA/Fludarabine, Pharmarubicin/Epirubicin, DEPOCYT®, ZD1839, LU 79553/Bis-Naphtalimide, LU 103793/Dolastain, Caetyx/liposomal doxorubicin, GEMZAR®/Gemcitabine, ZD 0473/ANORMED®, YM 116, iodine seeds, CDK4 and CDK2 inhibitors, PARP inhibitors, D4809/Dexifosamide, Ifes/MESNEX/Ifosamide, VUMON®/Teniposide, PARAPLATIN®/Carboplatin, Plantinol/cisplatin, Vepeside/Etoposide, ZD 9331, TAXOTERE®/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate. Preferred monocloncal antibodies include, but are not limited to, PANOREX® (Glaxo-Welicome), RITUXAN® (IDEC/Genentech/Hoffman la Roche), MYLOTARG® (Wyeth), CAMPATH® (Millennium), ZEVALIN® (IDEC and Schering AG), BEXXAR® (Corixa/GSK), ERBITUX® (Imclone/BMS), AVASTIN® (Genentech) HERCEPTIN® (Genentech/Hoffman la Roche), and TARCEVA® (OSI Pharmaceuticals/Genentech).

In certain embodiments, the chemotherapeutic agent is selected from the group consisting of taxol, doxorubicin, irinotecan, temozolomide, and combinations thereof.

In another embodiment, the method further comprises administering to the subject radiotherapy. In some embodiments, the one or more additional agents comprises both a chemotherapeutic agent and radiation/radiotherapy. In some embodiments wherein the one or more additional agents comprises both a chemotherapeutic agent and radiation/radiotherapy, the chemotherapeutic agent is selected from the group consisting of taxol, doxorubicin, irinotecan temozolomide, and combinations thereof.

Another aspect of the present disclosure provides a method for identifying a subject with a cancer that is suitable for immune checkpoint inhibitor therapy, the method comprising obtaining a sample from the subject with cancer, assaying for a mutation in ATM, wherein when a mutation is detected, the subject is suitable for immune checkpoint inhibitor therapy. In some embodiments, the ATM mutation is a nonsense mutation.

B. Pharmaceutical Compositions

The ATM inhibitors according to the present disclosure, and immune checkpoint inhibitors described herein are all referred to herein as "active compounds." Pharmaceutical formulations comprising the aforementioned active compounds also are provided herein. These pharmaceutical formulations comprise active compounds as described herein, in a pharmaceutically acceptable carrier. Pharmaceutical formulations can be prepared for oral or intravenous administration as discussed in greater detail below. Also, the presently disclosed subject matter provides such active compounds that have been lyophilized and that can be reconstituted to form pharmaceutically acceptable formulations (including formulations pharmaceutically acceptable in humans) for administration.

The term "carrier," as used herein, includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN polyethylene glycol, and PLURONICS®.

The therapeutically effective dosage of any specific active compound, the use of which is within the scope of embodiments described herein, will vary somewhat from compound to compound, and subject to subject, and will depend upon the condition of the subject and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level, such as up to about 10 mg/kg, with all weights being calculated based on the weight of the active base, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Preferred dosages are 1 μmol/kg to 50 μmol/kg, and more preferably 22 μmol/kg and 33 μmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

It is appreciated that the doses will vary, depending on the particular active agent and the condition to be treated. For example, if the subject is administered ipilimumab intravenously, a dose can vary from about 3 mg/kg (e.g., for stage IV melanoma) to about 10 mg/kg (e.g., for stage III melanoma). With respect to nivolumab, the intravenous dose can vary from 1-3 mg/kg for multiple indications. With respect to pembrolizumab, the intravenous dose can vary from 1-3 mg/kg, more specifically about 2 mg/kg for multiple indications. In some embodiments, the ATM inhibitor is administered intravenously at a dose of from about 10 to about 1000 $mg/m^2$, more specifically from about 10 to about 700 $mg/m^2$, and more specifically about 24 to about 650 $mg/m^2$.

In accordance with the presently disclosed methods, pharmaceutically active compounds as described herein can be administered orally as a solid or as a liquid, or can be administered intramuscularly, subcutaneously or intravenously as a solution, suspension, or emulsion. Alternatively, the compounds or salts also can be administered intravenously, subcutaneously or intramuscularly as a liposomal suspension. Pharmaceutically active compounds as described herein may also be administered, e.g., via the ocular route, the otic route, via inhalation, via nebulization, nasally, sublingually, transdermally, buccally, rectally, vaginally, and the like.

Pharmaceutical formulations suitable for intravenous or intramuscular injection are further embodiments provided herein. If a solution is desired, water is the carrier of choice with respect to water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

In addition to the one or more ATM inhibitors and one or more immune checkpoint inhibitors, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. The antimicrobial preservative is typically employed when the formulation is placed in a vial designed for multi-dose use. The pharmaceutical formulations described herein can be lyophilized using techniques well known in the art.

In yet another embodiment of the subject matter described herein, there is provided an injectable, stable, sterile formulation comprising one or more ATM inhibitors as described herein and one or more immune checkpoint inhibitors in unit dosage form in a sealed container. The active compounds are provided in the form of a lyophilizate, which is capable of being reconstituted with a suitable pharmaceutically acceptable carrier to form a liquid formulation suitable for injection thereof into a subject. When the active compounds are substantially water-insoluble, a sufficient amount of emulsifying agent, which is physiologically acceptable, can be employed in sufficient quantity to emulsify the compound or salt in an aqueous carrier.

In one embodiment, a pharmaceutical composition is provided, comprising: one or more ATM inhibitors as described herein; (b) a therapeutic amount of one or more immune checkpoint inhibitors; and (c) at least one pharmaceutically-acceptable carrier. In certain embodiments, the one or more immune checkpoint inhibitors is selected from the group consisting of ipilimumab, tremelimumab, nivolumab, pembrolizumab, pidilizumab, MEDI0680, atezolizumab, BMS-936559, MEDI4736, MSB0010718C, and combinations thereof. In other embodiments, the immune checkpoint inhibitor is a therapeutic agent selected from the group consisting of anti-CTLA-4, anti-PD-1, anti-PD-L, and combinations thereof.

Other aspects of the present disclosure further comprise a kit for treating cancer in a subject and/or for enhancing the efficacy of an immune checkpoint inhibitor therapy in a subject suffering from cancer, the kit comprising, consisting of, or consisting essentially of a pharmaceutical composition as provided herein, means for administering the pharmaceutical composition, and instructions for use. In some embodiments, the means for administering the pharmaceutical compositions comprises a syringe.

Yet another aspect of the present disclosure provides all that is disclosed and illustrated herein.

The following examples further illustrate the present invention but should not be construed as limiting its scope in any way.

EXAMPLES

In these Examples we show, in part, the unexpected result that Ataxia Telangiectasia Mutated (ATM), a key factor in cellular DNA damage response, can serve both as a biomarker and a therapeutic target to enable ICB therapy. Our work indicates that ATM mutations are predictive of clinical benefit from ICB therapy. Consistently, genetic depletion of ATM in murine cancer cells significantly delayed tumor growth in syngeneic mouse hosts in a T-cell-dependent manner. Further, chemical inhibition of ATM significantly potentiated anti-PD1 therapy of mouse tumors. We found that ATM inhibition potently activates the cGAS/STING pathway, which enhances lymphocyte infiltration into the tumor microenvironment. We further discovered that ATM inhibition downregulated TFAM levels, which led to mitochondrial DNA leakage into the cytoplasm, cGAS/STING activation, and activation of innate interferon response.

Example 1

Successful knockout of the ATM gene in 4T1 and B16F10 cells. By use of lentivirus-mediated CRISPR-Cas9 technology, we successfully generated ATM knockouts in 4T1 and B16F10 cells (FIG. 1). In vitro, ATM knockout did not cause any obvious growth delay in the tumor cells.

Example 2

Figure 2:
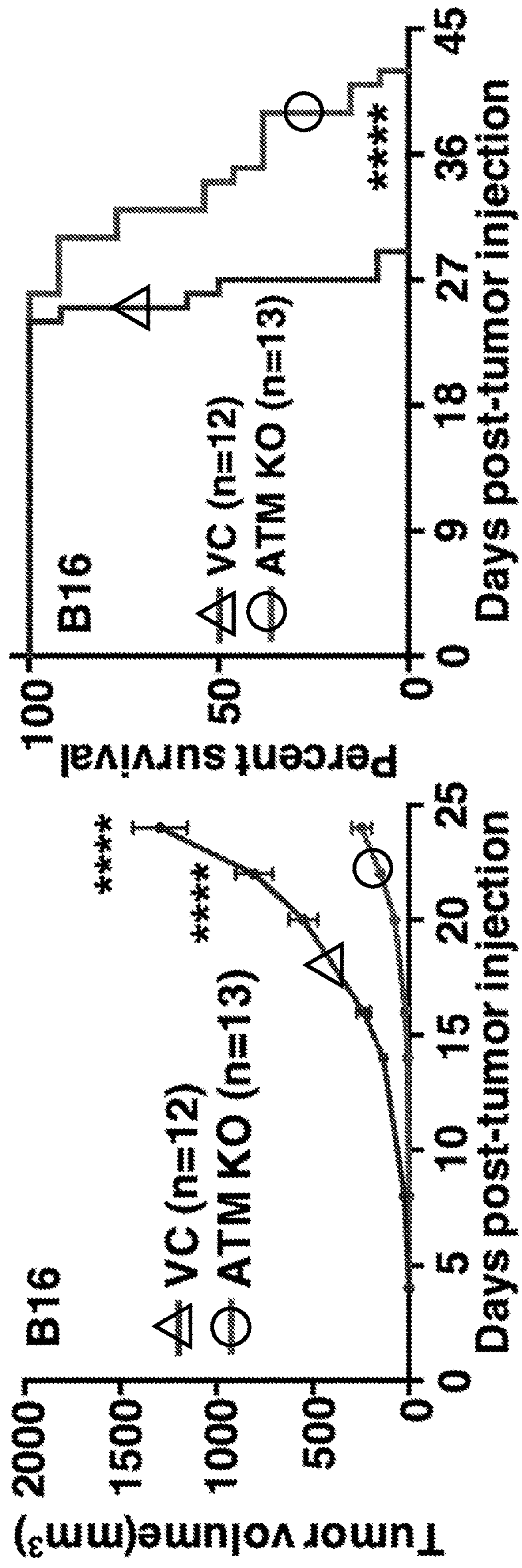
FIG. 2 presents graphs showing that ATM knockout caused significant growth delay in the B16F10 murine melanoma cells inoculated into syngeneic C57BL/6 mice in accordance with one embodiment of the present disclosure.

Effect of ATM knockout on tumor growth in syngeneic mice. In order to determine if ATM depletion has any effect on the tumorigenic ability of tumor cells in vivo, 4T1 murine breast cancer cells or B16F10 murine melanoma cells with ATM knockout were inoculated into sygeneic Balb/C or C57BL/6 mice, respectively. ATM knockout caused a significant growth delay of the B16F10 tumor cells in C57BL/6 mice (FIG. 2).

Figure 3:
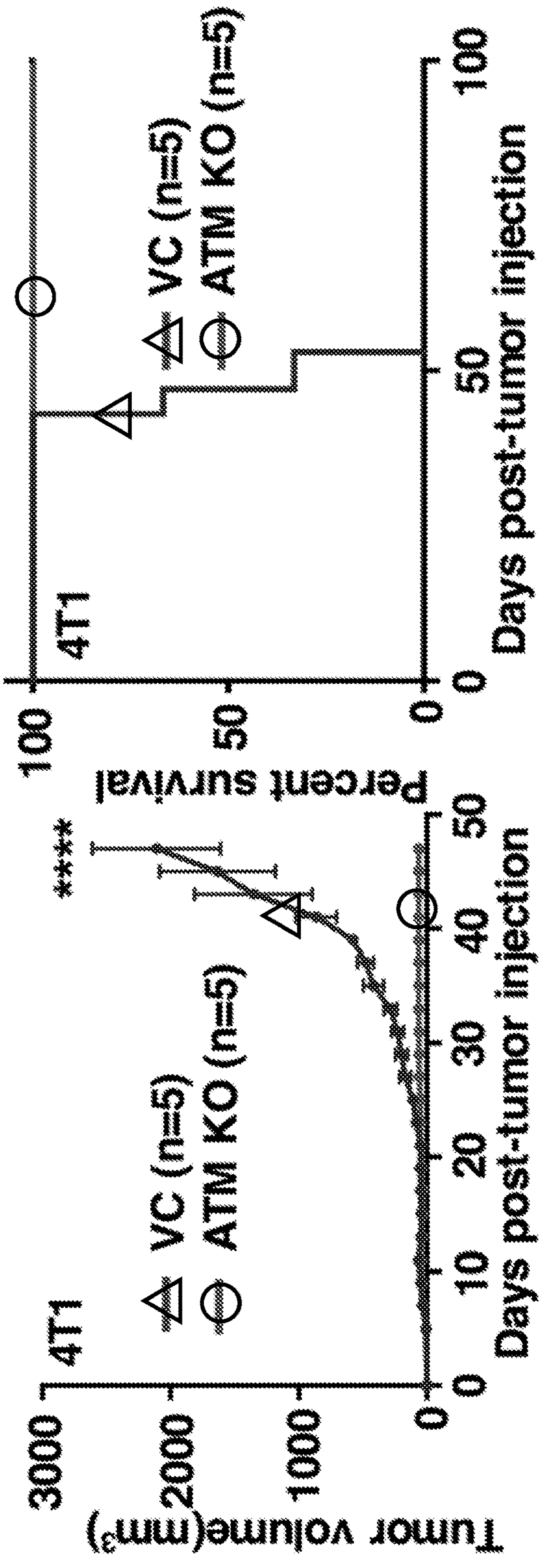
FIG. 3 presents graphs showing that ATM knockout completely inhibited tumor growth from 4T1 cells inoculated into syngeneic Balb/C mice in accordance with one embodiment of the present disclosure.

Surprisingly, ATM knockout in the 4T1 cells prevented tumor formation altogether in the Balb/C mice (FIG. 3). This is striking given that 4T1 tumor cells are known to be very malignant and form tumors in mice very easily. The inability to form tumors and the fact that it has no growth deficiencies in vitro intimated that ATM plays a critical role for the tumorigenic abilities of 4T1 in vivo.

Example 3

Figure 4:
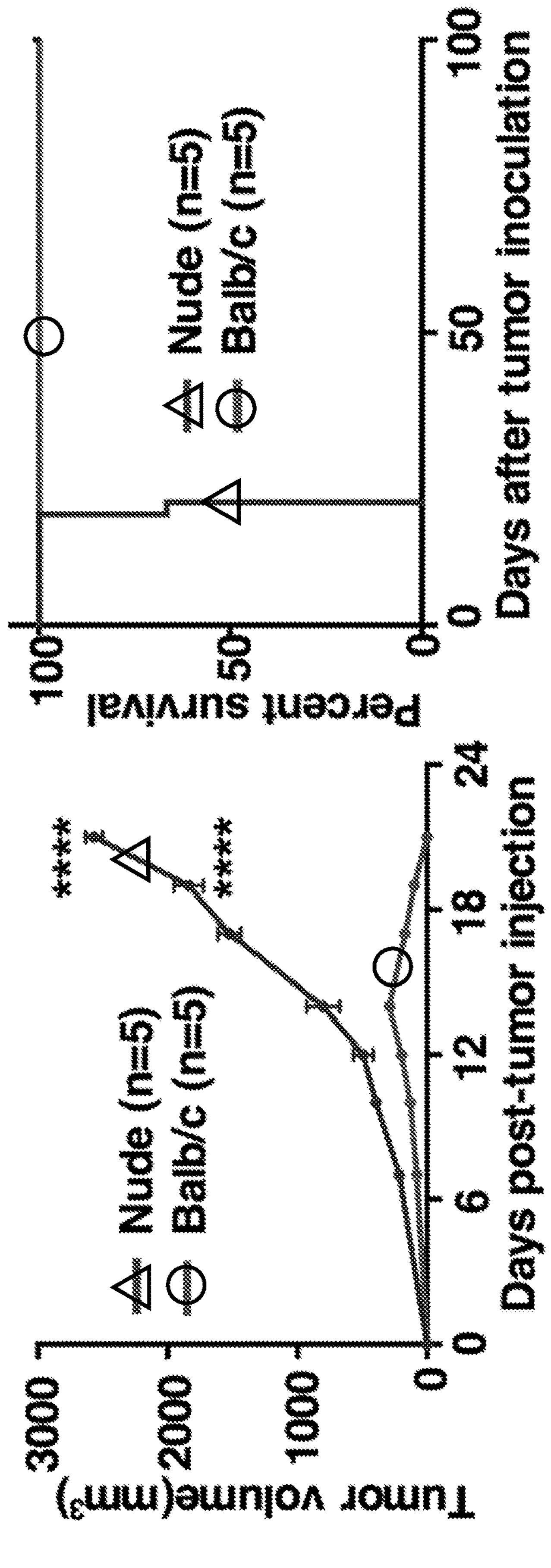
FIG. 4 presents graphs showing ATM knockout in the 4T1 murine breast cancer cell line inhibited tumor formation in the syngeneic mice but failed to do so in the athymic nude mice in accordance with one embodiment of the present disclosure.

Effect of ATM depletion on tumor growth in immune-deficient mice. Our data indicated a total lack of tumor growth in 4T1 injected Balb/C mice despite its normal growth rate in vitro. We hypothesized that there might be a role for the immune system. Thus, we attempted to evaluate the abilities of 4T1-ATMKO cells to form tumors in athymic nude mice, which do not have T cells. Unlike what was observed in syngeneic, immunocompetent hosts, ATM deficient 4T1 cells could form tumors at in nude mice (FIG. 4). These data support that the tumorigenic deficiencies observed in the syngeneic, immunocompetent hosts were dependent on host T cells.

Example 4

Figure 5:
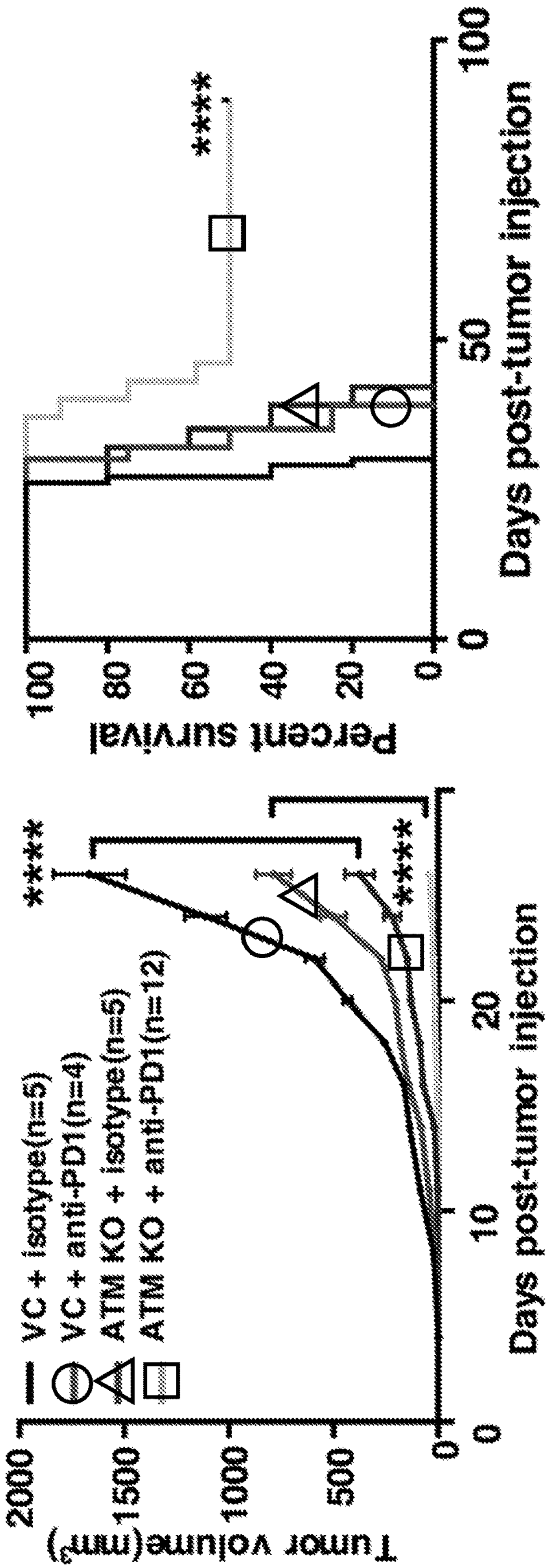
FIG. 5 presents graphs showing ATM depletion overcame resistance to anti-PD1 immune checkpoint inhibitor therapy in the B16F10 model in accordance with one embodiment of the present disclosure.

ATM depletion overcomes resistance to immune checkpoint therapy. In order to examine if ATM depletion could enhance immune checkpoint therapy, we inoculated B16F10-ATMKO cells into C57BL/6 mice. Earlier, ATM knockout in the C57BL/6 mice induced a clear growth delay (FIG. 2). However, in combination with anti-PD1 therapy, 6 out of 12 mice inoculated with B16F10-ATMKO cells did not form tumors at all (FIG. 5).

In comparison, all anti-PD1 (only) treated control B16F10 group formed tumors. Thus, our data support our hypothesis that ATM depletion in could overcome resistance to anti-PD1 immune checkpoint therapy.

Example 5

Figure 6:
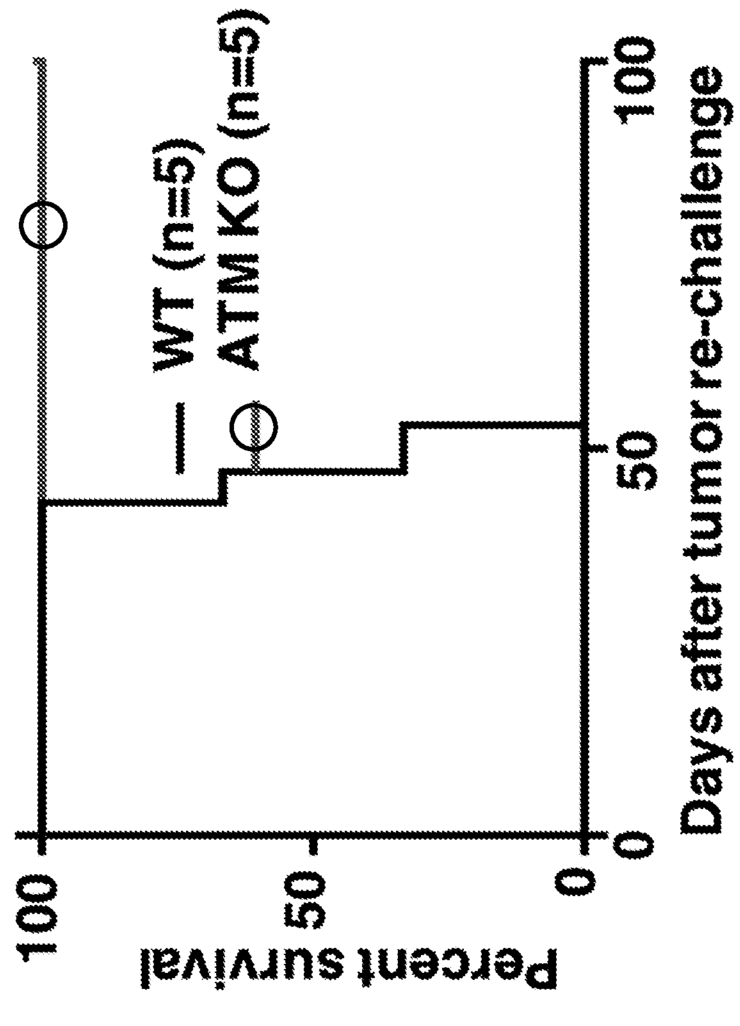
FIG. 6 presents a graph showing previously non-inoculated Balb/C mice and ones that remained cancer free after 4T1ATMKO inoculation were re-challenged with wild-type 4T1 cells ($1.0\times10^5$) and observed for tumor growth in accordance with one embodiment of the present disclosure.
Figure 7:
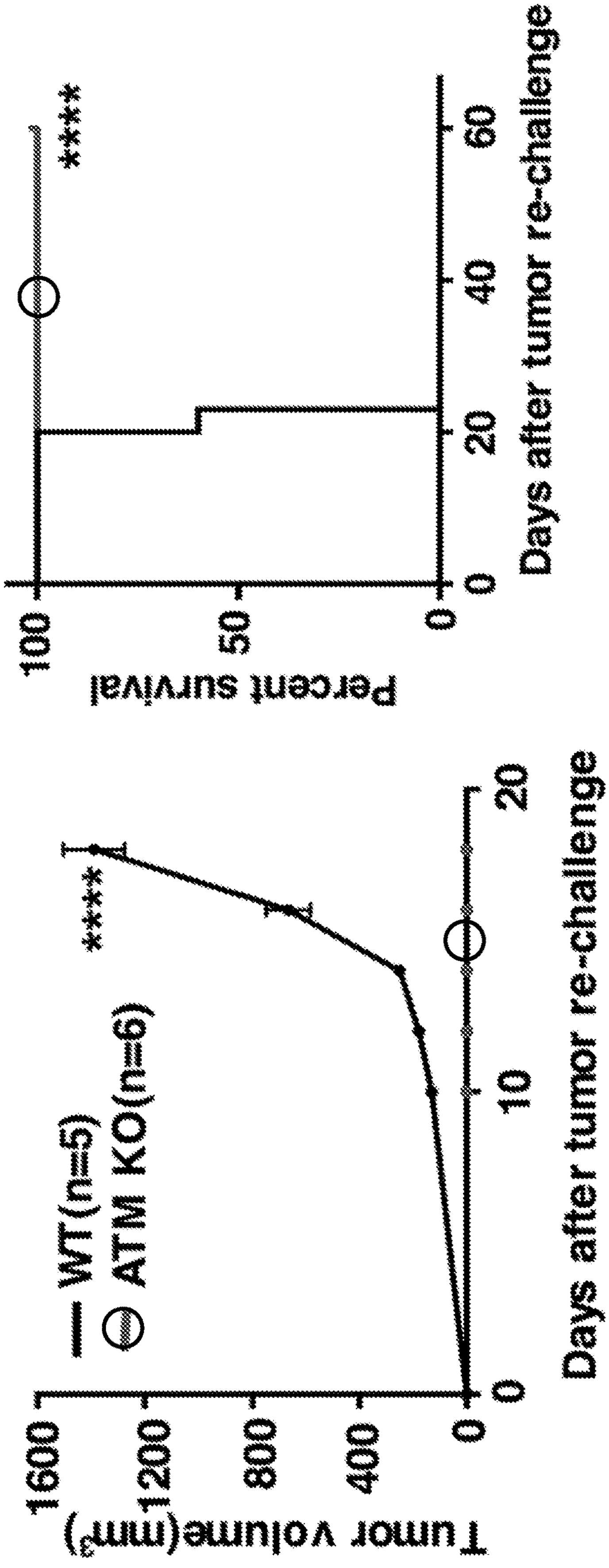
FIG. 7 presents graphs showing previously non-inoculated C57/BL6 mice and ones that remained cancer free after combined with PD1 and ATM-depletion treatment were re-challenged with wild-type B16F10 cells ($1.0\times10^5$) and observed for tumor growth in accordance with one embodiment of the present disclosure.

Development of long-term anti-tumor immunity in mice that remained tumor free after inoculation with ATMKO tumor cells. We also evaluated if those mice that remained tumor free after injection with 4T1-ATMKO alone or after B16F10-ATMKO and anti-PD1 therapy had developed long-term anti-tumor immunity. Wild type 4T1 cells and B16F10 cells were injected into Balb/C and C57BL/6 mice, respectively, that had survived previous inoculations of ATMKO 4T1 or B16F10 cells. Strikingly, 5 out of 5 Balb/C mice that had previously rejected 4T1ATMKO cells also became resistant to wild type 4T1 cells (FIG. 6) while 6 of 6 C57BL/6 mice that were cured of their B16F10ATMKO tumors with the help of anti-PD1 therapy became resistant to wild type B16F10 challenge (FIG. 7).

These data clearly demonstrate the development of long-term anti-tumor immunity in host mice inoculated with ATM deficient tumor cells.

Example 7

Figure 8:
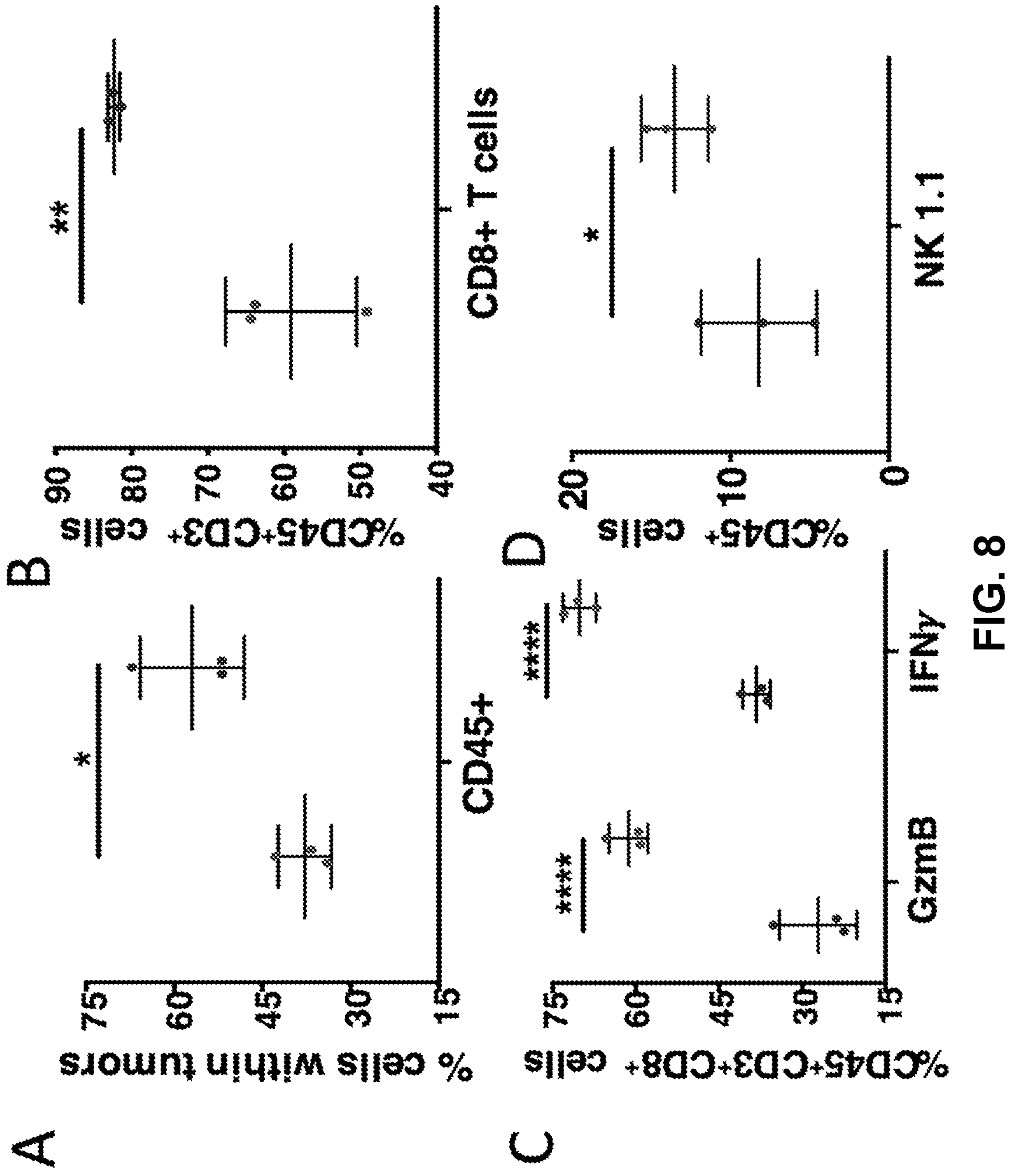
FIG. 8 presents graphs showing immune infiltrate analysis for the relative fractions of various immunoeffector cell subsets by use of flow cytometery in accordance with one embodiment of the present disclosure.

Increased intratumoral infiltration of immune effector cells. Because of the potent anti-tumor immunity observed in mice challenged with ATM deficient tumor cells, we examined immune cell infiltration into ATMKO tumors by use of flow cytometry. Our data indicated that there was significant increases in immune infiltrate such as CD45+ leukocytes (FIG. 8A), CD8+ T cells (FIG. 8B), Gzmb+ or IFNβ+CD8+ T cells (FIG. 8C), and NK1.1+NK cells (FIG. 8D) in ATM-deficient tumors, strongly suggesting that that ATM deficiency led to a "hotter" tumor microenvironment.

Example 8

Figure 9:
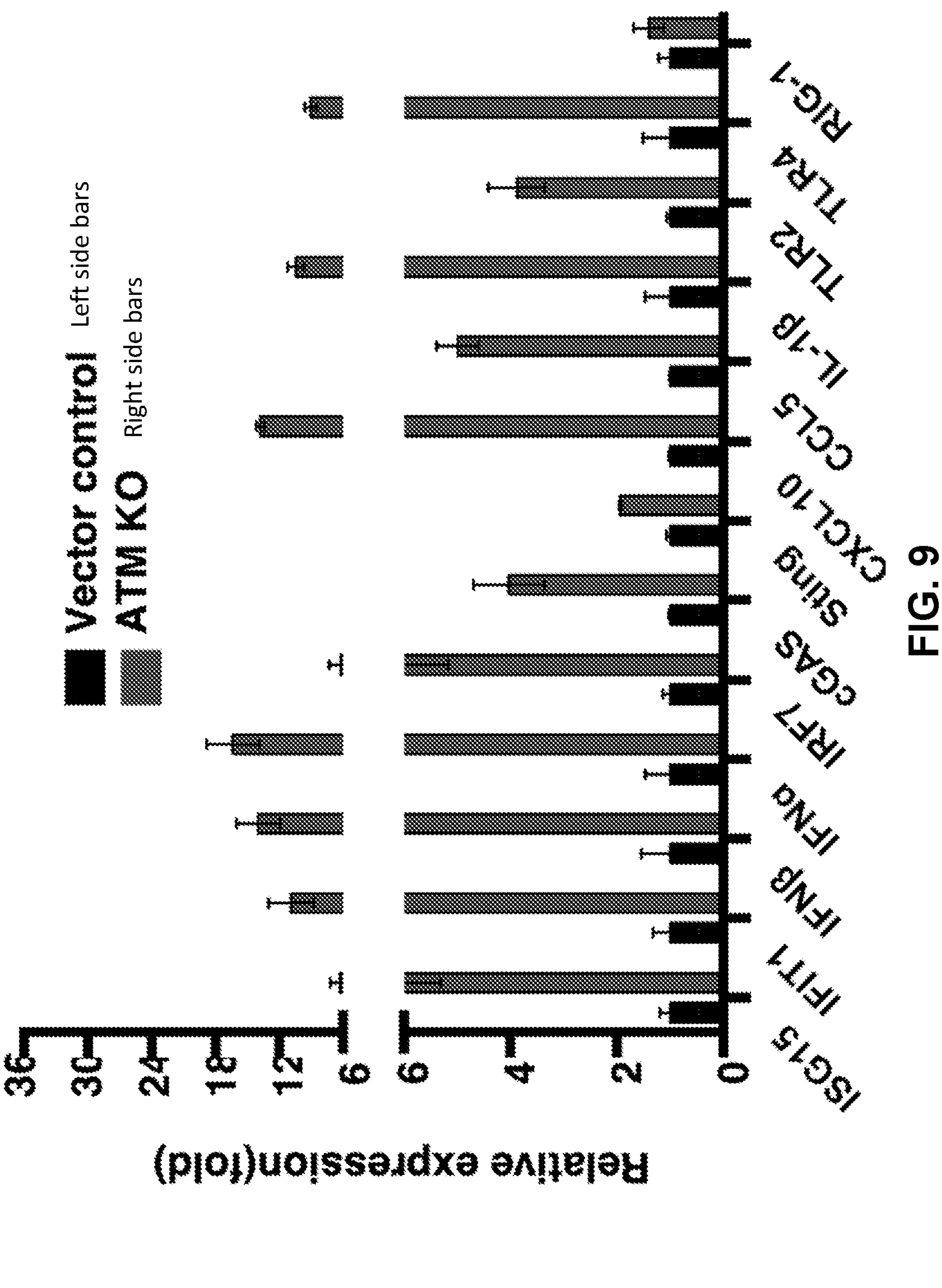
FIG. 9 presents a graph showing Q-RT-PCR analysis of the mRNA expression levels of various genes involved in activation of cellular innate immunity in accordance with one embodiment of the present disclosure.

Increased activation of cellular innate immunity in ATM-deficient tumor cells. To identify factors downstream of ATM that may lead to significant immune cell infiltration, we profiled different cytokine gene expression levels in ATMKO tumor cells by use of Q-RT-PCR (FIG. 9). Our results indicate that pro-inflammatory cytokines such as IFNa, IFNβ, IL-1β were expressed at significantly higher levels in ATMKO cells. In addition, the expression of both cGAS and Sting genes were also expressed at significantly higher levels, indicating involvement of the cellular innate immunity.

Example 9

Figure 10:
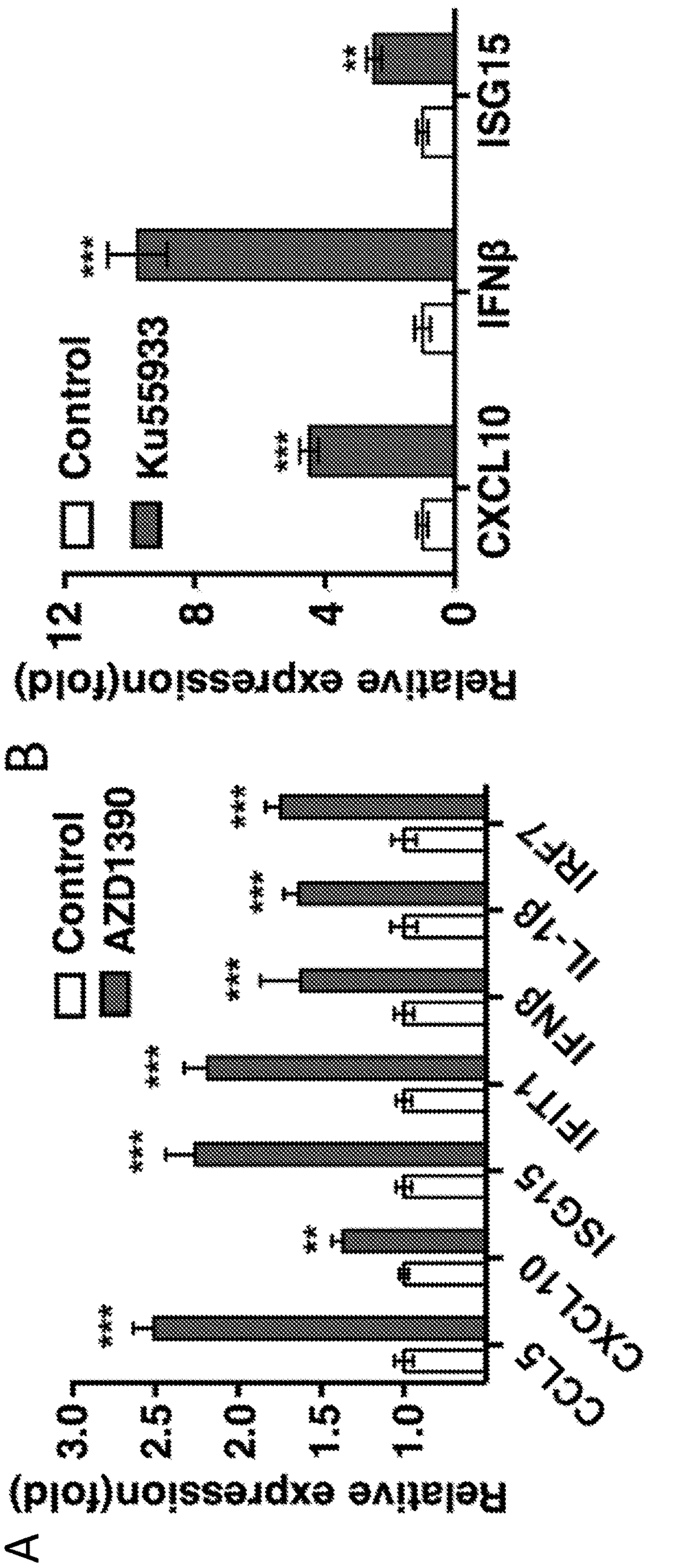
FIG. 10 presents graphs showing Q-RT-PCR analysis of mRNA expression of cytokines involved in cellular innate immunity in wild type 4T1 cells treated with ATM inhibitors AZD1390 (A) and Ku55933 (B) in accordance with one embodiment of the present disclosure.

Activation of innate cellular immunity and tumor suppression induced by a small molecule inhibitor of ATM. To determine if small molecule inhibitors of ATM could achieve similar effects in activating the cellular innate immunity, we used AZD1390 and KU55933, two small molecule inhibitors of ATM. AZD1390 is currently in phase I clinical trial. We quantified pro-inflammatory cytokine expression in cells treated with ATM inhibitors, and our results indicate they indeed induce the pro-inflammatory cytokine genes involved in cellular innate immunity (FIG. 10)

Example 10

Figure 11:
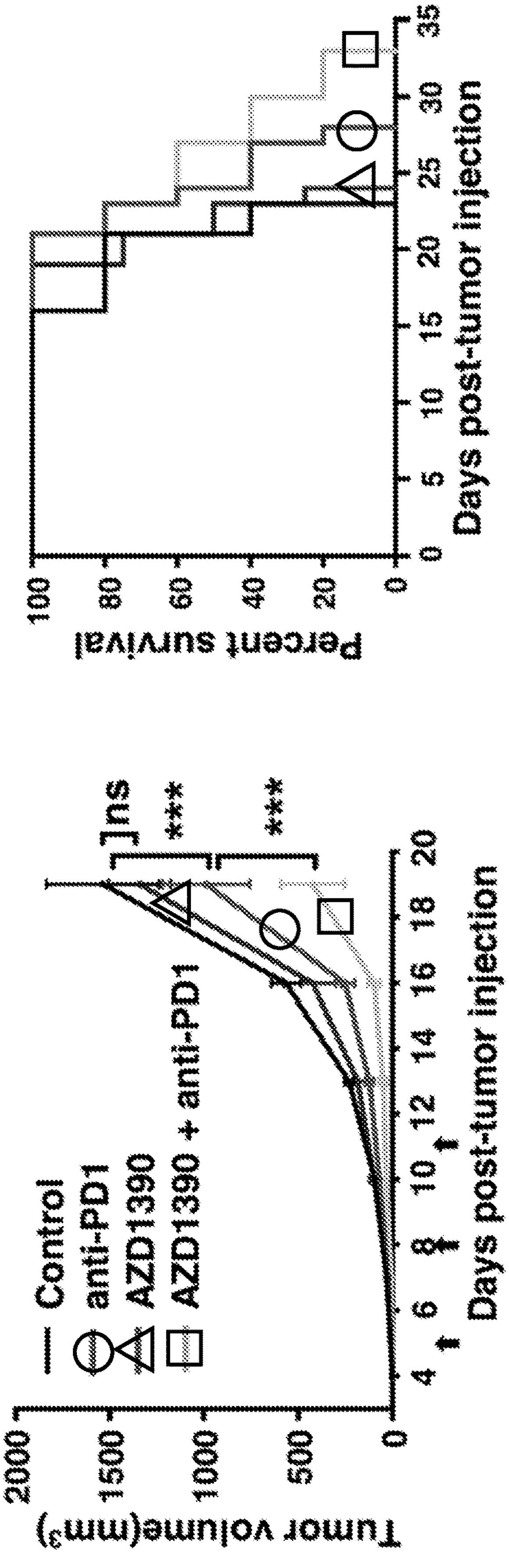
FIG. 11 presents graphs showing combined treatment of B16F10 melanoma with an anti-PD1 antibody (100 μg/mouse) and AZD1390 (2.5 mg/Kg) in accordance with one embodiment of the present disclosure.

Tumor suppression induced by small molecule inhibitors of ATM and anti-PD1 antibody. To determine if ATM inhibition by a small molecule inhibitor could enhance anti-PD1 therapy, we carried out tumor growth delay experiments in B16F10 melanoma (FIG. 11). Our data indicate that AZD1390 significantly enhanced tumor suppression mediated by an anti-PD1 antibody.

Example 11

Figure 12:
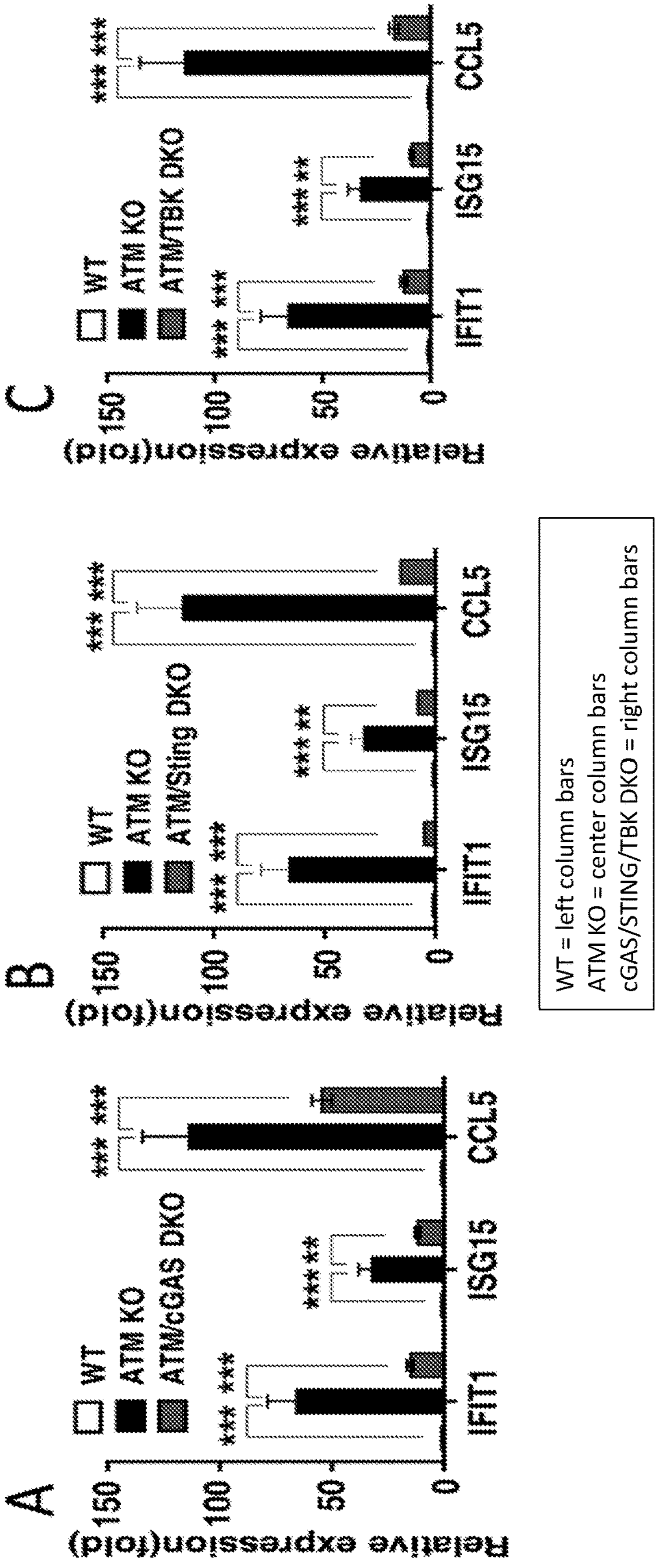
FIG. 12 presents graphs showing Q-RT-PCR profiling of cellular immunity gene expression in B16 cells with an individual ATM knockout and double ATM/cGAS (A), ATM/Sting (B), and ATM/TBK knockouts (C) in accordance with one embodiment of the present disclosure.
Figure 13:
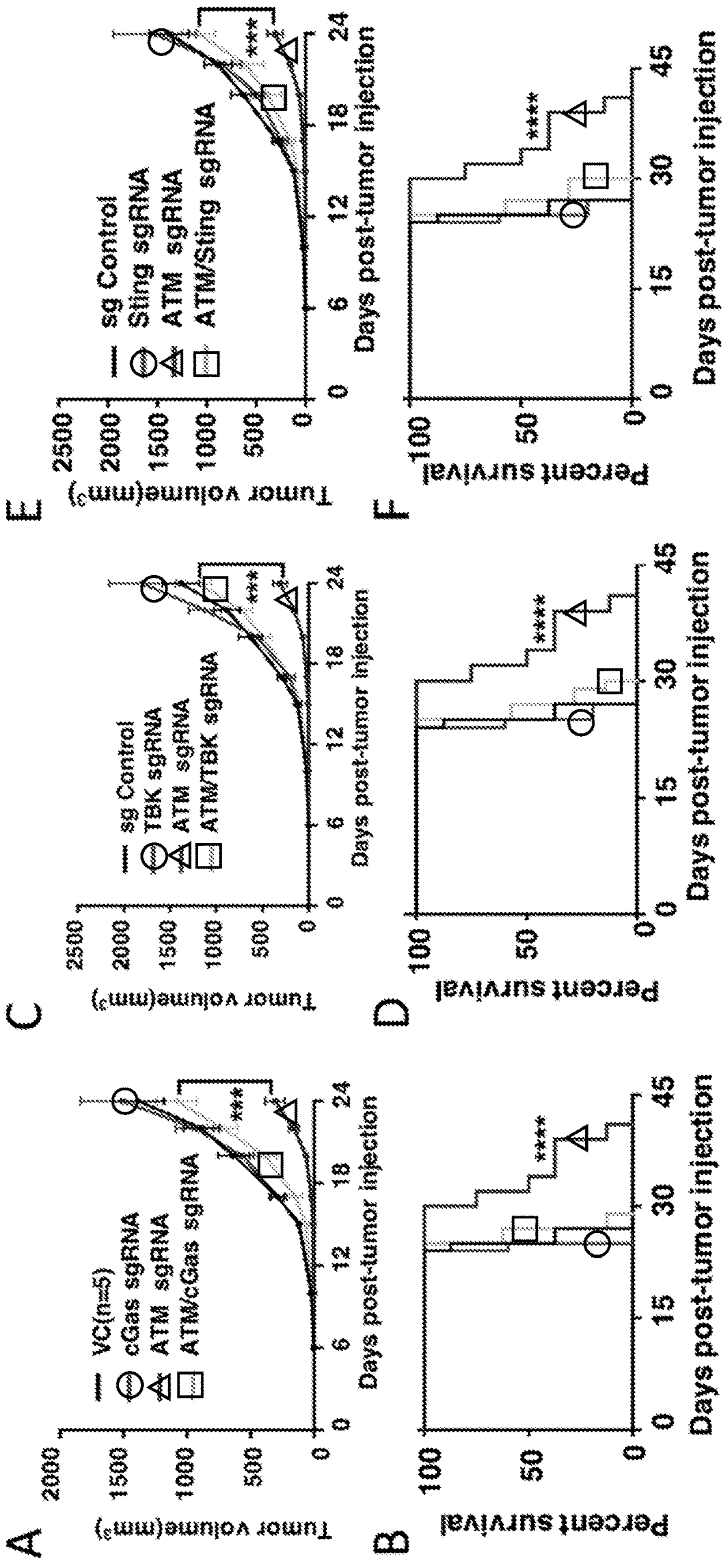
FIG. 13 presents graphs showing tumor formation and host mice survival from B16 cells with individual ATM knockout and double ATM/cGAS (A-B), ATM/Sting (C-D), and ATM/TBK knockouts (E-F) in accordance with one embodiment of the present disclosure.

Importance roles of cGAS/Sting in mediating increased inflammatory cytokine gene expression and tumor suppression in ATM-deficient B16F10 tumor cells. In order to determine if cGAS/Sting is the key effector downstream of ATM inhibition in ATM deficiency induced tumor suppression, we generated double cGAS or Sting knockout in B16F10 cells with ATM deficiency. We then profiled cytokine expression in these cells by use of Q-RT-PCR. Our results indicated that Sting knockout abolished most of the cytokine over-expression in the ATM KO cells (FIG. 12B). Similar results were also obtained for cGAS knockout. (FIG. 12C). Tumor growth delay experiments indicated that cGAS, Sting, or TBK knockout completely abolished ATM deficiency induced tumor growth delay in the B16F10 melanoma model (FIG. 13).

Example 12

Loss of ATM predicted for clinical benefit to ICB therapy in human cancer patients Because only a minority of patients can benefit from ICB treatment, biomarkers are needed to identify those patients to reduce costly and unnecessary treatments. However, currently available biomarkers that are clinically approved, including high PD-L1 expression (>50%) for non-small cell lung cancer (NSCLC) and microsatellite instability (MSI) for MMR deficient tumors, can only identify a subset of those who might benefit. This is because only 22% of NSCLC patients have high PD-L1 expression levels' (Dietel, M. et al. Lung Cancer (2019), doi:10.1016/j.lungcan.2019.06.012) and the prevalence of MSI across all cancer types is about 3.8% (Bonneville, R. et al., *JCO Precis Oncol* (2017), doi:10.1200/PO.17.00073).

Figure 14:
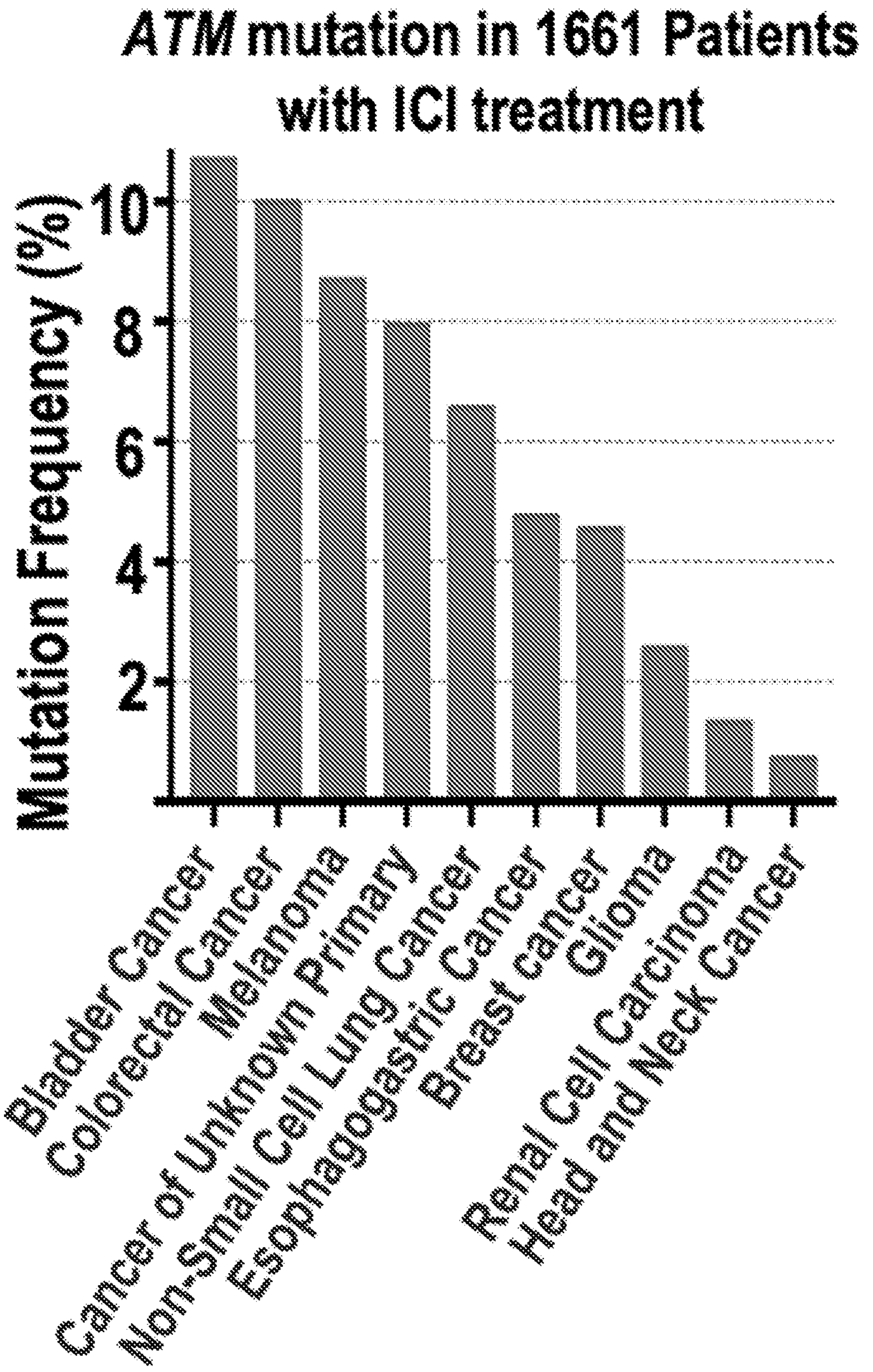
FIG. 14 presents ATM mutation frequencies across 10 human cancer types among 1661 advanced-stage cancer patients treated with ICB therapy.
Figure 15:
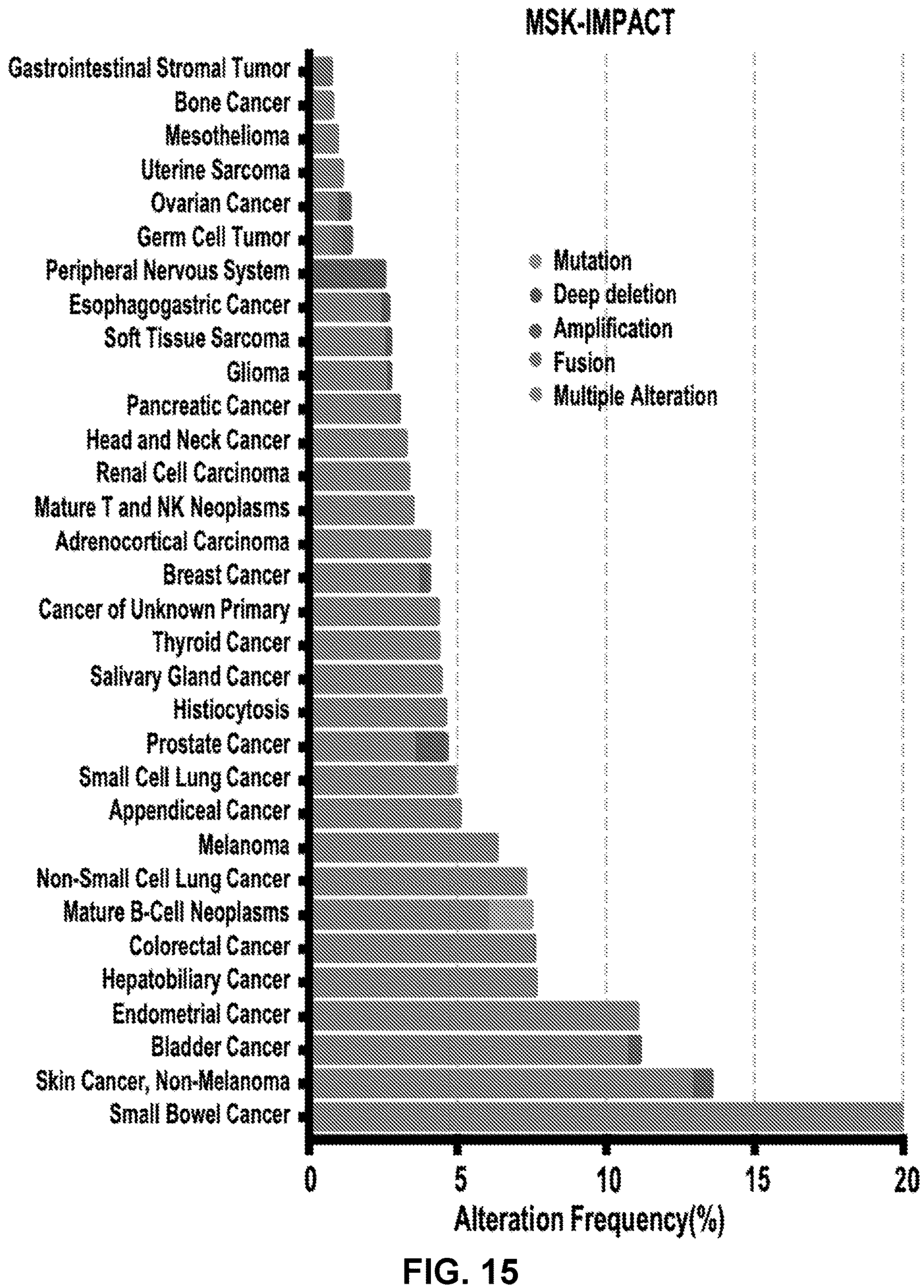
FIG. 15 presents frequencies of ATM alterations across different cancer types in the 10336-patient MSK-IMPACT cohort. Data from the cBioportal website.
Figure 16:
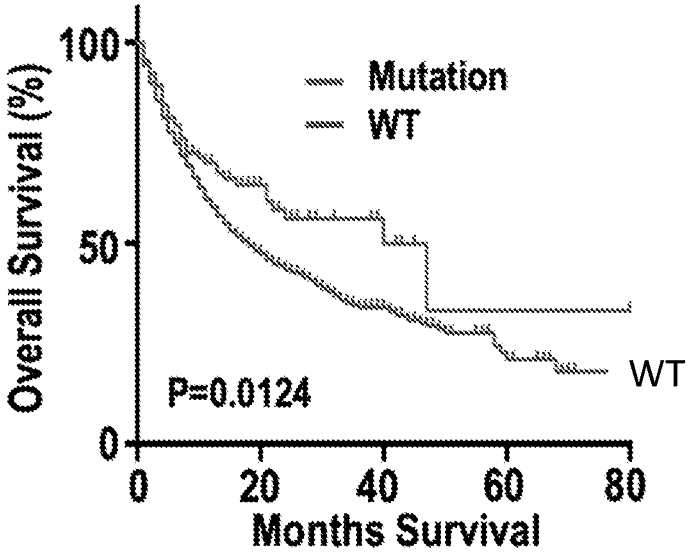
FIG. 16 presents Kaplan-Meier analysis of overall survival (OS) in immune checkpoint blockade (ICB)-treated patients with ATM mutations (unmarked trace) vs those without ("WT" trace). P values calculated by use of the logrank (Mantel-Cox) test.
Figure 17:
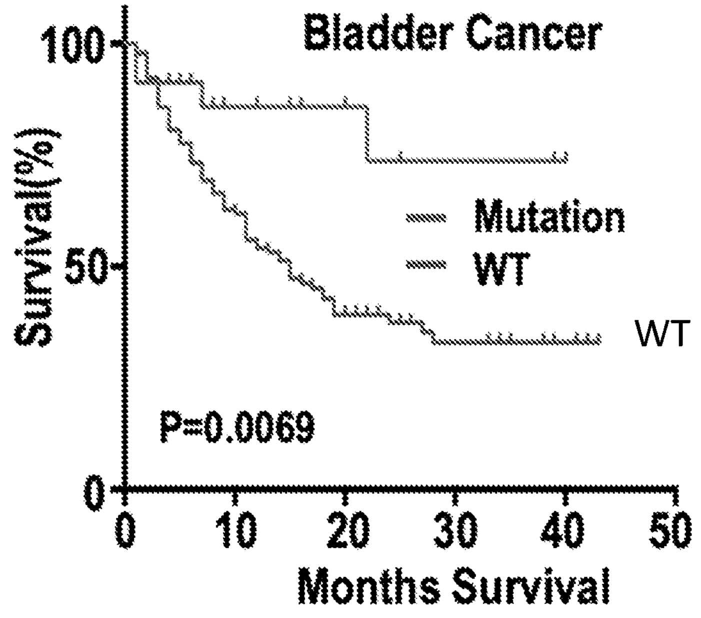
FIG. 17 presents Kaplan-Meier survival data of bladder cancer for patients with (unmarked trace) and or without ("WT" trace) ATM mutations. P values calculated by use of the logrank (Mantel-Cox) test.
Figure 65:
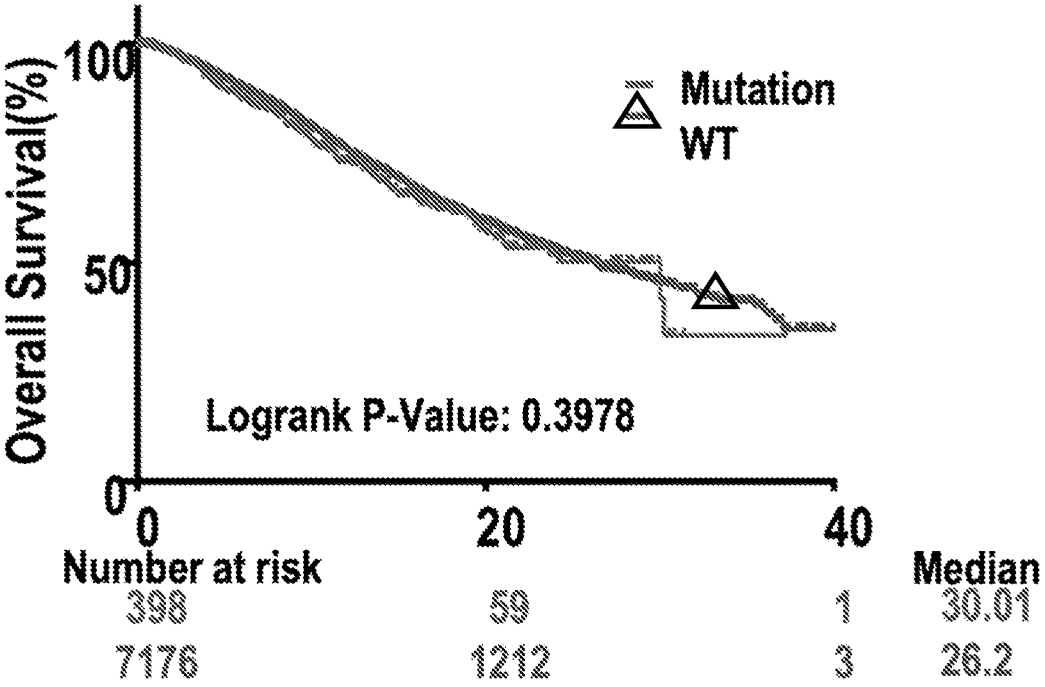
FIG. 65 presents Kaplan-Meier survival curve of patients from the whole MSK-IMPACT cohort with (unlabeled trace) or without (triangle trace) ATM mutations.
Figure 66:
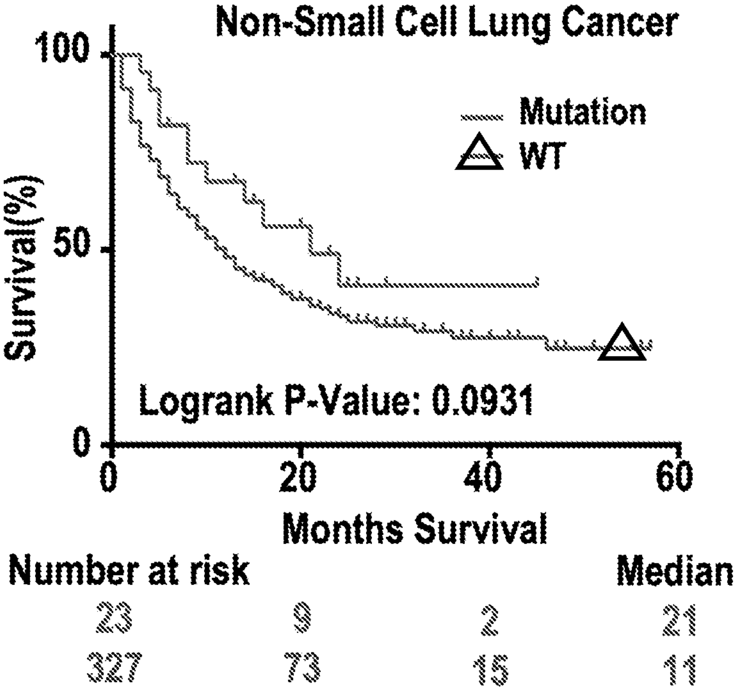
FIG. 66 presents Kaplan-Meier survival data non-small cell lung cancer for patients with (unlabeled trace) or without (triangle trace) ATM mutations. Collectively.

To explore the role of ATM in ICB cancer treatment, we analyzed recently published clinical and genomic data from a large cohort of 1,661 late stage cancer patients treated with ICB at Memorial Sloan Kettering Cancer Institute, which we refer to as the MSK-TMB cohort (Samstein, R. M. et al. *Nat Genet* (2019) doi:10.1038/s41588-018-0312-8). We found that about 6.32% of the patients in the cohort across different cancer types had mutations in the ATM gene (FIG. 14 and Table 1). Among them, bladder, colorectal, melanoma, non-small cell lung, esophagogastric, and breast cancer patients had the highest mutation rates. This pattern of mutation rates among different cancer patients also held true in the much larger 10,336-patient MSK-IMPACT cohort of cancer patients where the overall prevalence of ATM mutations reached 4.83% (FIG. 15 and Table 2) (Zehir, A. et al. *Nat Med* (2017), doi:10.1038/nm.4333). Most importantly, we found that the patients with ATM mutations had a significantly better overall survival (OS) than those without (p=0.0124, FIG. 16). This was in contrast to patients in the MSK-IMPACT cohort who had not gone through ICB treatment: those with ATM mutations had a similar OS as those without (FIG. 65), suggesting that mutation in the ATM gene was a predictive rather than prognostic biomarker for ICB treatment. Further analysis of MSK-TMB cohort showed that among different cancer types, ATM mutation also predicted for better OS (82.6%) in bladder cancer (p=0.0069, FIG. 17). A similar trend was also observed in non-small cell lung cancer (NSCLC) (p=0.0931, FIG. 66; data for FIG. 65 and FIG. 66 obtained from the 1661-patient ICB treatment cohort (Samstein et al, Nature Genetics, 2019) and the 10336 MSK-IMPACT clinical sequencing cohort (Zehir et al, Nature Medicine, 2017). Therefore, our identification of ATM mutation as a biomarker to select for patients for ICB treatment is highly significant clinically. Its impact as an ICB biomarker is can be as high as MSI or higher because the prevalence of ATM mutations is around 4.83% across the 10,336-patient MSK-IMPACT pan-cancer cohort and over or close to 10% in small bowl cancer, melanoma, bladder cancer, and endometrial cancer (FIG. 15; Zehir, A. et al. ibid.).

Figure 18:
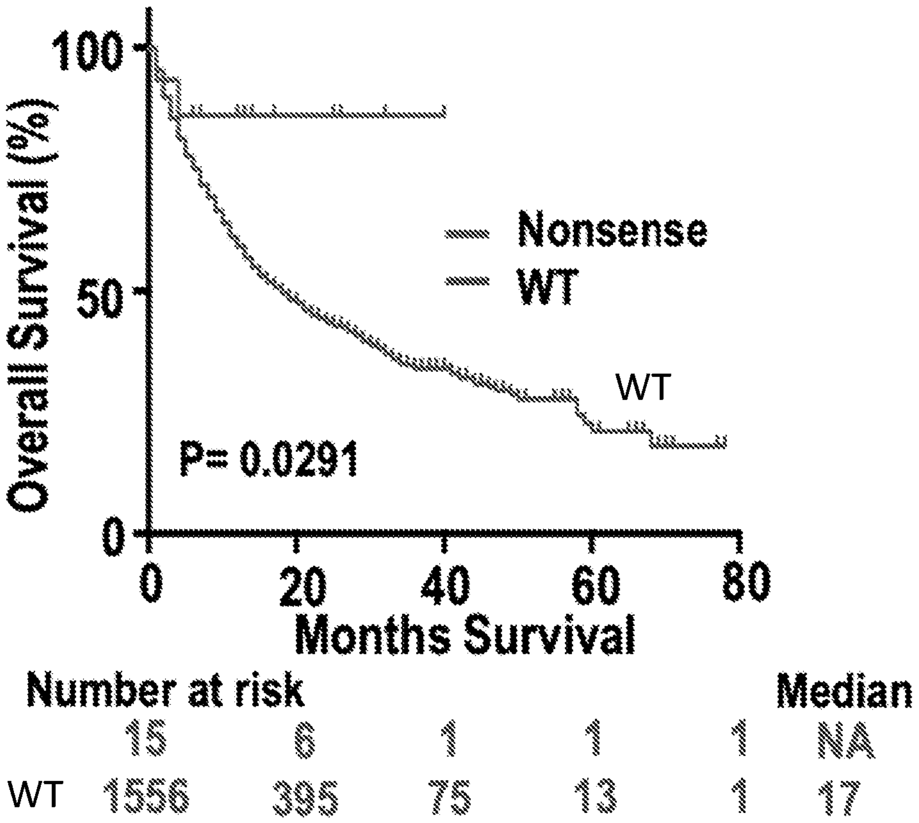
FIG. 18 presents Kaplan-Meier analysis of OS in ICB-treated patients with ATM nonsense mutation (unmarked trace) vs those without ("WT" trace). P values calculated by use of the logrank (Mantel-Cox) test. Collectively, FIGS. 14-18 indicate that ATM mutations predict the clinical benefit of ICB therapy in human cancer patients.

P values calculated by use of logrank test), although the difference did not reach statistical significance due to low patient numbers. Most notably, the functional relevance of ATM in ICB therapy was strongly suggested by the observation that patients in the ICB-treated MSK-TMB cohort with nonsense ATM mutations had a significantly better OS (>85%) than those without (p=0.0291, FIG. 18). Only two out of 15 patients died in the entire observation period. Therefore, our analysis of patient data suggested mutant ATM gene being functionally involved player as well as a promising predictive biomarker for ICB therapy.

Example 13

Figure 19:
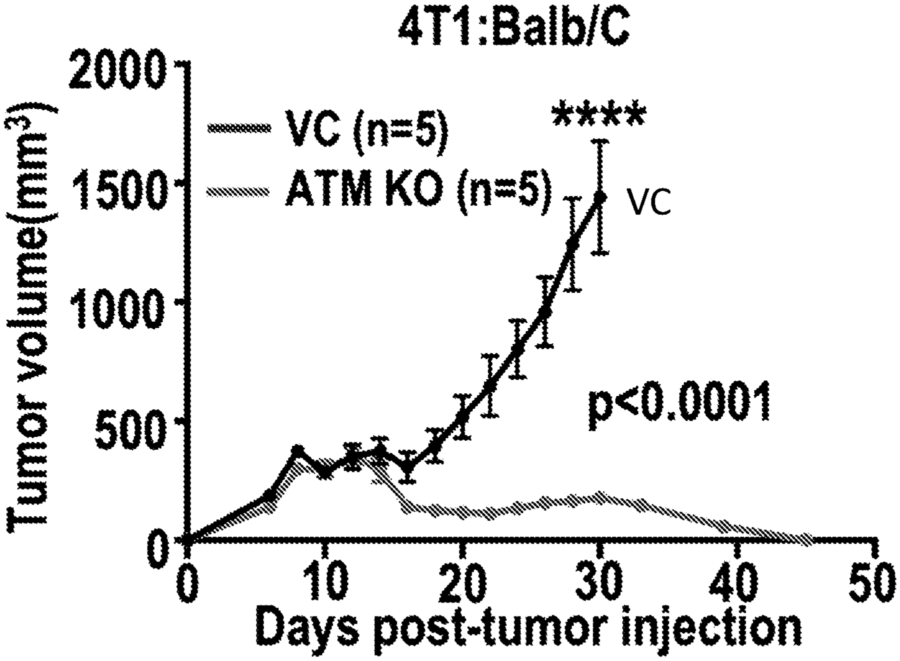
FIG. 19 presents tumor volume of Balb/c mice inoculated with about $2\times10^5$ vector control (VC) or ATM knockout 4T1 cells.
Figure 20:
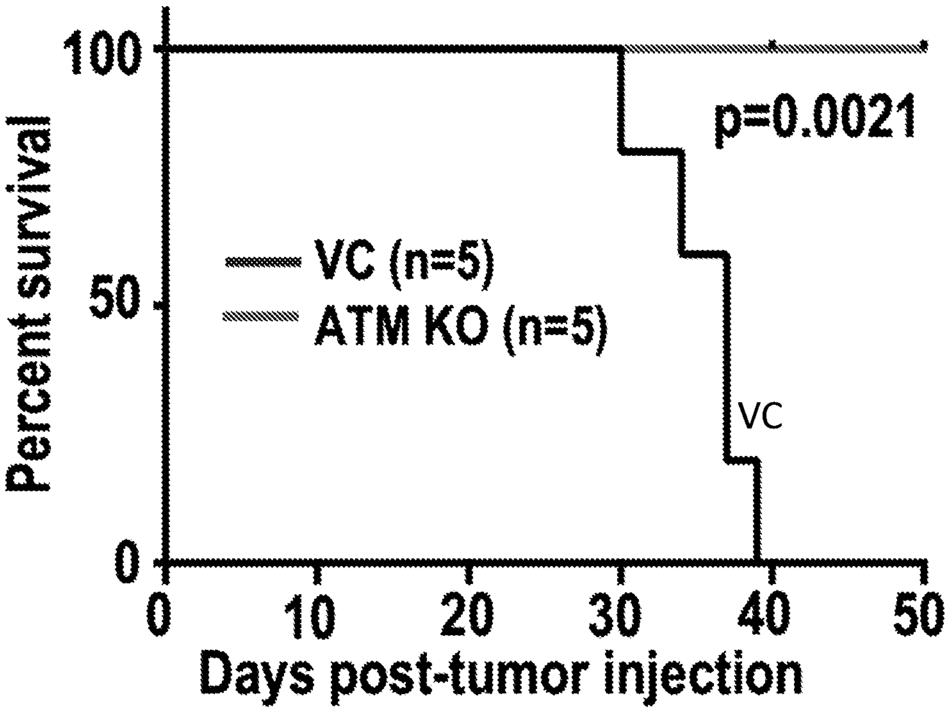
FIG. 20 presents Kaplan-Meier survival curve of Balb/c mice inoculated with about $2\times10^5$ vector control (VC) or ATM knockout 4T1 cells.
Figure 21:
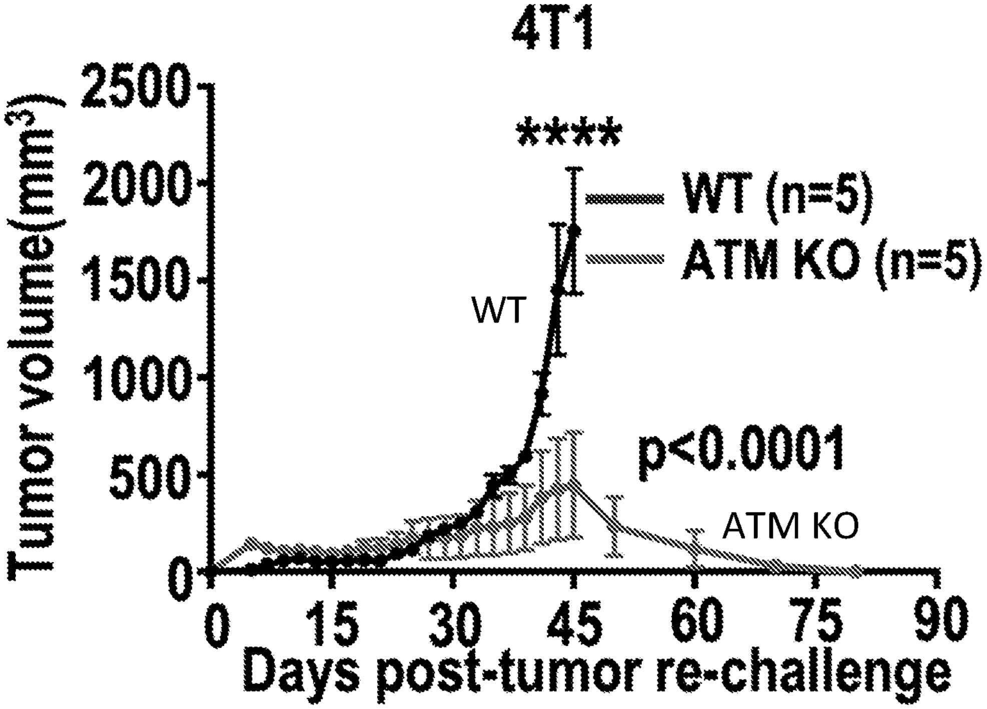
FIG. 21 presents tumor volume of naïve and previously challenged but tumor-free Balb/C mice after being re-challenged with $1\times10^5$ wild type 4T1 tumor cells. Tumor free Balb/C mice were re-challenged after remaining tumor free 40 days after initial inoculation with ATMKO 4T1 cells.
Figure 22:
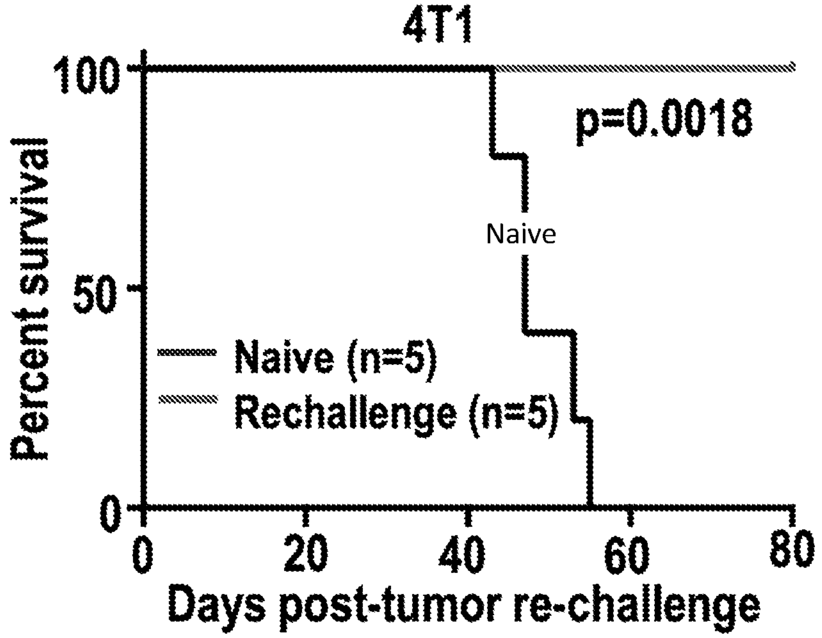
FIG. 22 presents Kaplan-Meier survival curve of naïve and previously challenged but tumor-free Balb/C mice after being re-challenged with $1\times10^5$ wild type 4T1 tumor cells. Tumor free Balb/C mice were re-challenged after remaining tumor free 40 days after initial inoculation with ATMKO 4T1 cells.
Figure 67:
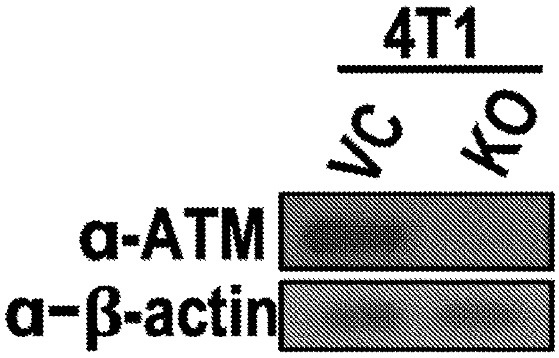
FIG. 67 presents western blot analysis of the expression of ATM in murine 4T1 tumor cells transduced with a vector control and an sgRNA targeting ATM.
Figure 68:
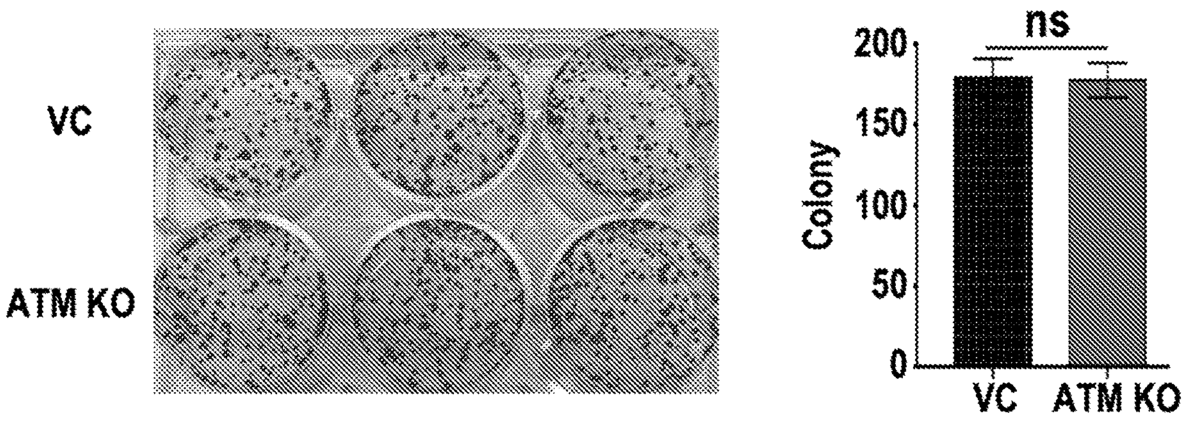
FIG. 68 presents clonogenic abilities of vector control and ATM KO 4T1 cells. Cell were seeded in 6-Well plates (500 cells per well) in triplicates and allowed to grow for 6 days before staining with crystal violet (left panel). Aggregate colony areas were quantified by use of Image J and plotted (right panel).
Figure 69:
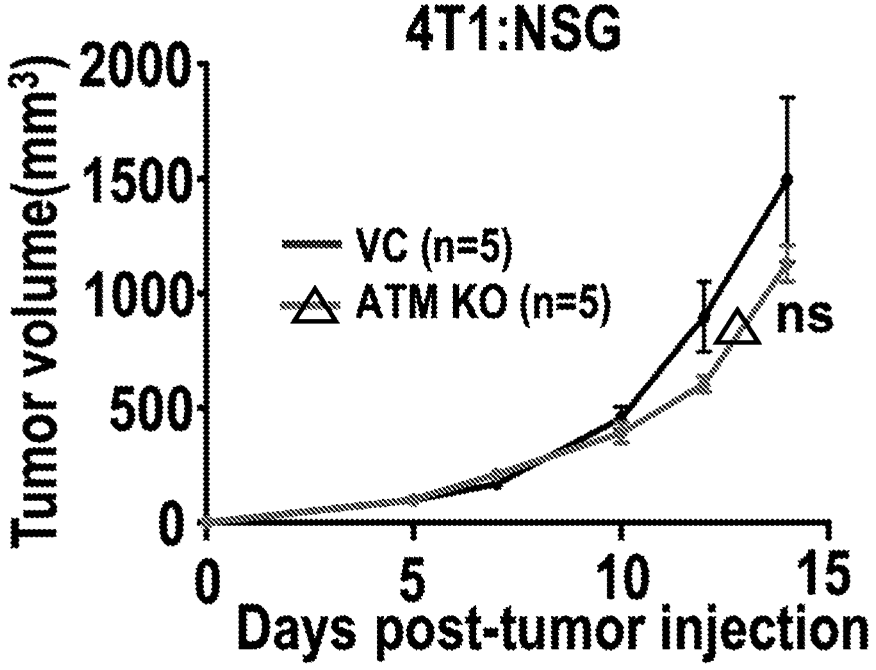
FIG. 69 presents tumor volume of immunodeficient NSG mice inoculated with about $1\times10^5$ control or ATMKO 4T1 cells.

ATM inhibition suppressed tumor growth and sensitized tumors to PD-1 blockade To test if genetic inhibition of ATM had similar functional relevance to immunotherapy as clinical patients results, we knocked out ATM in the poorly immunogenic 4T1 murine breast cancer cells by use of the CRISPR-Cas9 technology[45] (FIG. 67). In vitro growth of the tumor cells was not significantly affected (FIG. 68). However, when clonal 4T1ATMKO cells were inoculated into syngeneic Balb/C mice, those cells failed to form tumors while vector control cells formed tumors readily (FIGS. 19, 20). This striking result prompted us to determine if the observed tumor-suppressive effect of ATM deficiency on tumor growth was dependent on an intact immune system. ATM-deficient and vector control 4T1 cells were inoculated into immunodeficient NSG mice. Our results indicated that 4T1ATMKO cells formed tumors almost at the same rate as the vector control cells (FIGS. 69, 70), thereby suggesting that the strong tumor-suppressive effect of ATM knockout in the 4T1 tumor lines was dependent on an intact immune system. A further proof for the involvement of the immune system came from tumor cell re-challenge experiments where wild type 4T1 cells were injected into Balb/C mice that rejected 4T1ATMKO cells. All mice that survived initial 4T1ATMKO inoculation also rejected wild type 4T1 tumor cell re-challenge. In comparison, all naïve mice succumbed to wild type 4T1 challenge (FIGS. 21, 22).

Figure 23:
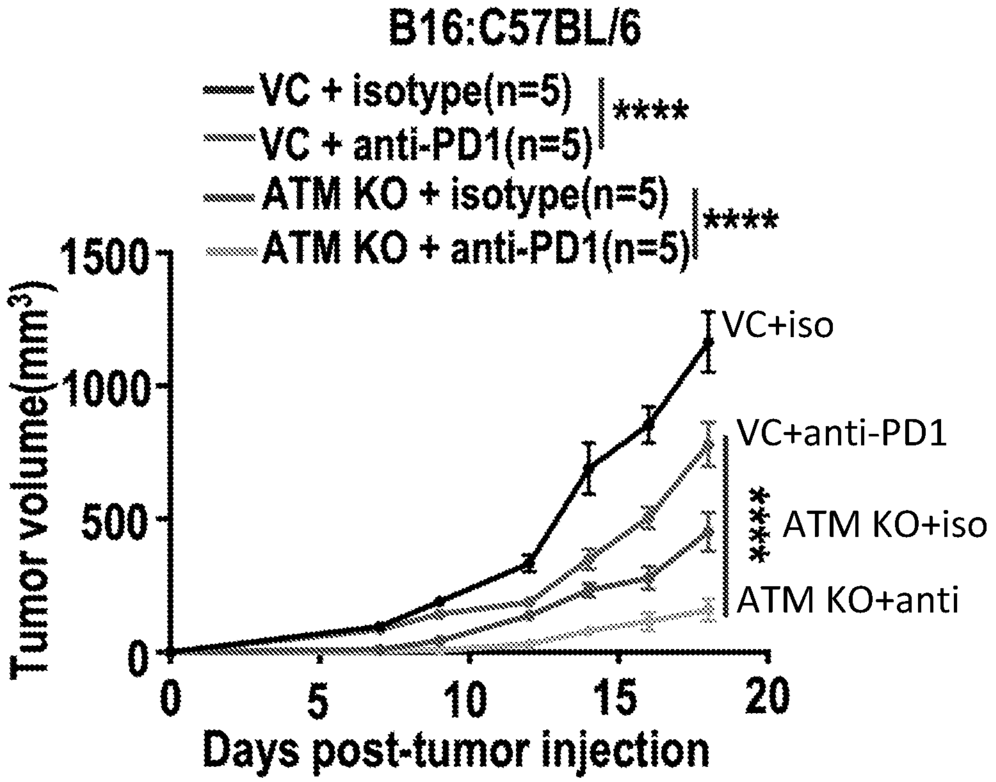
FIG. 23 presents tumor volume of C57BL/6 mice inoculated with about $1\times10^5$ vector control (VC) or mixed population of ATMKO B16F10 cells and treated with 100 μg/mouse anti-PD1 or isotype control Ab on days 6, 9, 12 post inoculation.
Figure 24:
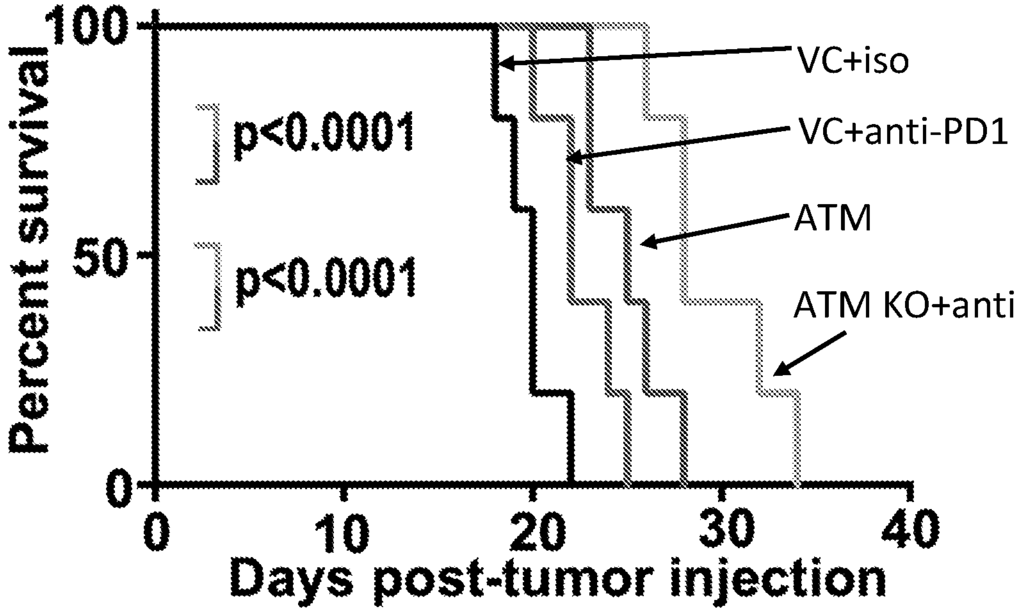
FIG. 24 presents Kaplan-Meier survival curve of C57BL/6 mice inoculated with about $1\times10^5$ vector control (VC) or mixed population of ATMKO B16F10 cells and treated with 100 μg/mouse anti-PD1 or isotype control Ab on days 6, 9, 12 post inoculation.
Figure 71:
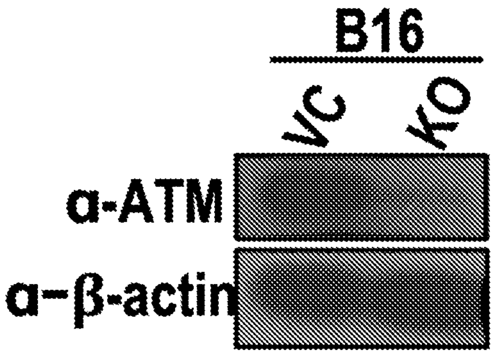
FIG. 71 presents western blot analysis of ATM expression of vector control and ATMKO murine B16 tumor cells.
Figure 72:
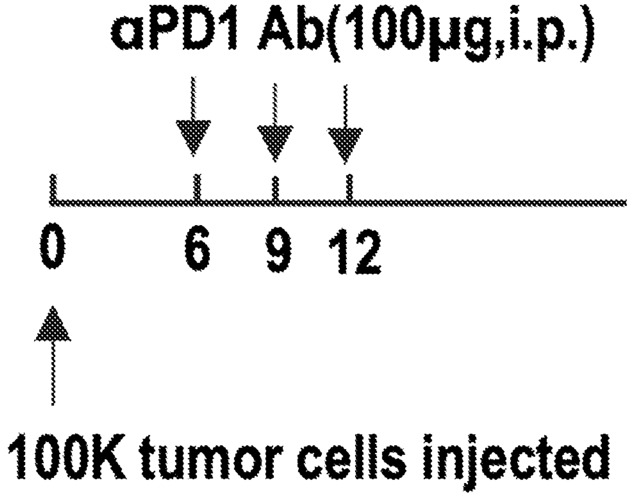
FIG. 72 presents the treatment schedule used for tumor growth delay experiments in FIG. 23 and FIG. 24.

To assess if ATM inhibition could synergize with ICB therapy, we generated mixed population ATMKO cells in the B16F10 (melanoma) background by use of the CRISPR-Cas9 technology (FIG. 71). Syngeneic mice were injected with the cells and treated with anti-PD1 antibodies following a schedule outlined in FIG. 72. Our results indicated that partial inhibition of ATM synergized with anti-PD1 therapy potently in suppressing tumor growth and prolonging host survival in the B16F10 melanoma model (FIGS. 23, 24). Thus, genetic inactivation of ATM showed significantly tumor growth delay and had strong synergic effects with anti-PD-1 immunotherapy.

Figure 25:
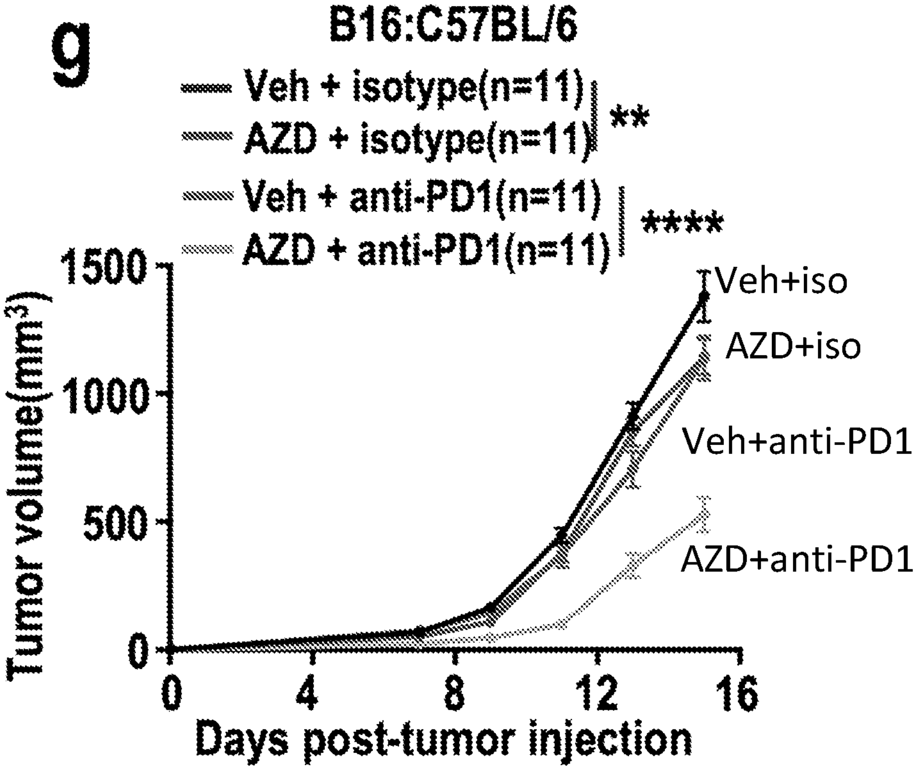
FIG. 25 presents tumor volume of C57BL/6 mice inoculated with about $1\times10^5$B16F10 cells and treated with 100 μg/mouse anti-PD1 or isotype control Ab on days 6, 9, 12 and AZD1390 (10 mg/kg) or vehicle (daily from days 4-14). Data from two independent experiments.
Figure 26:
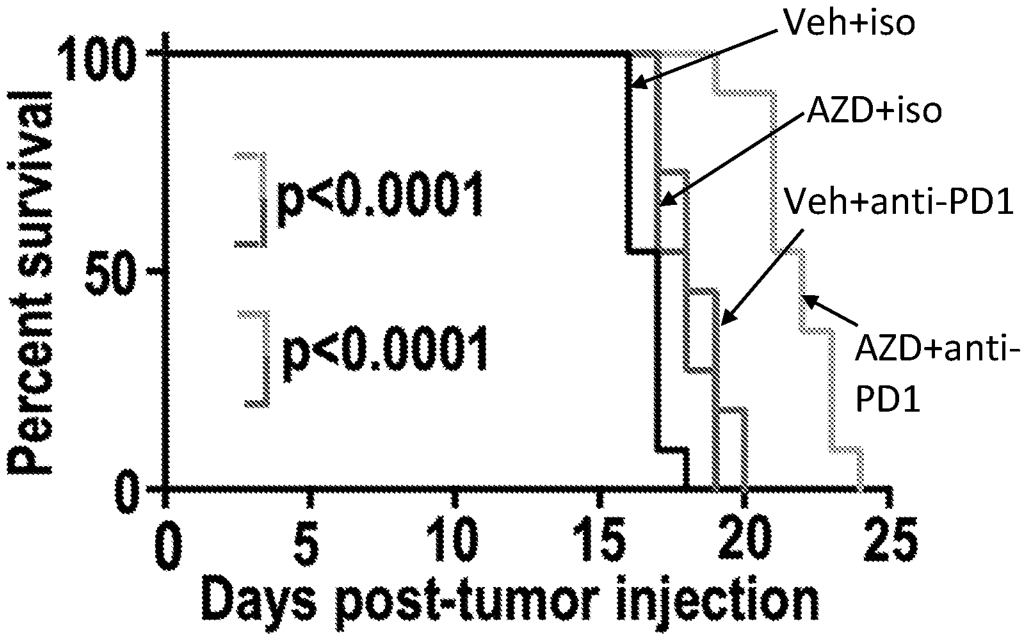
FIG. 26 presents Kaplan-Meier survival curve of C57BL/6 mice inoculated with about $1\times10^5$ B16F10 cells and treated with 100 μg/mouse anti-PD1 or isotype control Ab on days 6, 9, 12 and AZD1390 (10 mg/kg) or vehicle (daily from days 4-14). Data from two independent experiments.
Figure 27:
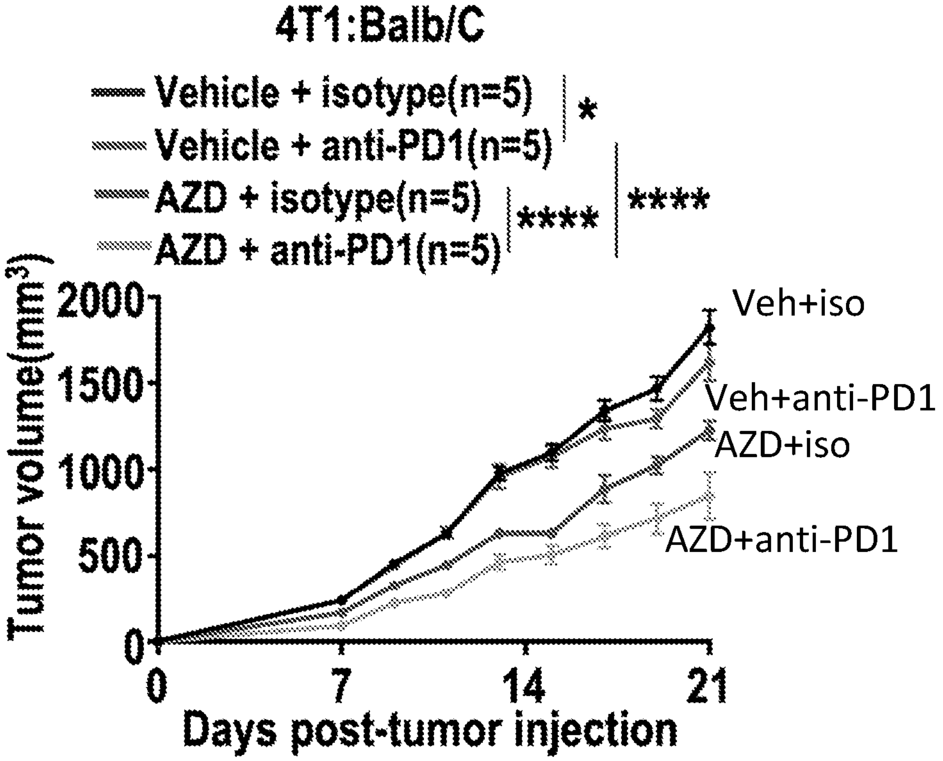
FIG. 27 presents tumor volume of Balb/c mice inoculated with about $1\times10^5$ 4 T1 cells and treated with 100 μg/mouse anti-PD1 or isotype control on days 6, 9, 12 and AZD1390 (10 mg/kg) or vehicle (daily from days 4-14).
Figure 28:
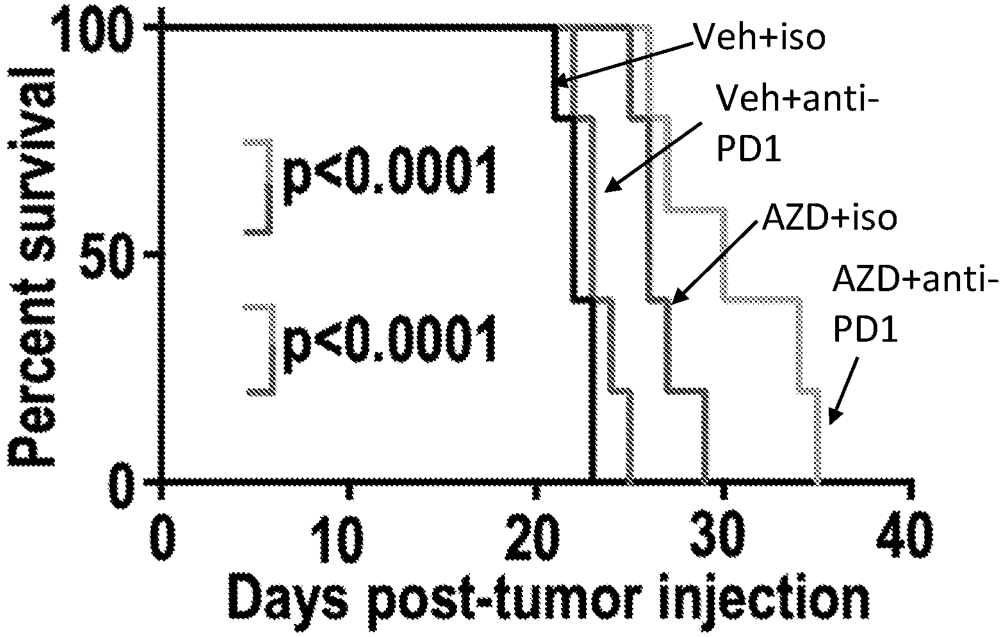
FIG. 28 presents Kaplan-Meier survival curve of Balb/c mice inoculated with about $1\times10^5$ 4 T1 cells and treated with 100 μg/mouse anti-PD1 or isotype control on days 6, 9, 12 and AZD1390 (10 mg/kg) or vehicle (daily from days 4-14). Collectively, FIGS. 19-28 demonstrate that ATM inhibition induces a significant tumor growth delay and overcomes tumor resistance to ant-PD-1 therapy.
Figure 73:
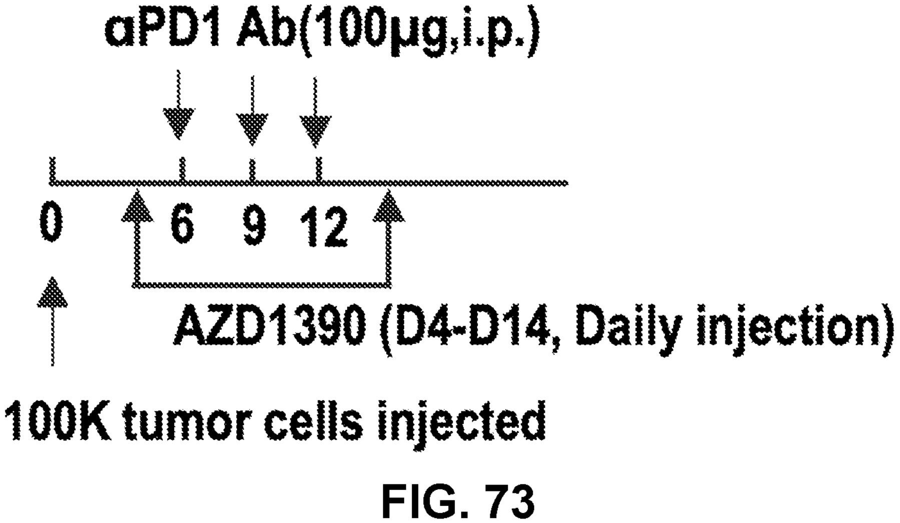
FIG. 73 presents the treatment schedule used for tumor growth delay experiments in FIGS. 25-28. Collectively.

We next examined if a similar synergy between ATM inhibition and anti-PD1 antibody treatment could be recapitulated by use of a small molecule inhibitor of ATM, AZD1390. AZD1390 is a potent and selective ATM kinase inhibitor that significantly enhanced radiotherapy of glioma in preclinical models (Durant, S. T. et al. *Sci Adv* (2018) doi:10.1126/sciadv.aat1719) and had been in phase I clinical trial (NCT03423628). Following a schedule shown in FIG. 73, we show that while AZD1390 alone had almost negligible effect on tumor growth in B16F10 tumors, it significantly enhanced the anti-tumor efficacy of the anti-PD1 antibody (FIGS. 25, 26). Similar results were also observed in the 4T1 model (FIGS. 27, 28). Here the anti-PD1 antibody had minimal effect on 4T1 tumor growth but the ATM inhibitor showed a more significant tumor-suppressive effect. Most importantly, combined AZD1390 and anti-PD1 treatment had a synergistic effect in prolonging the survival of host mice in both models (FIGS. 26, 28). Therefore, our results from both genetic depletion and chemical inhibition strongly suggested that ATM inhibition can effectively overcome tumor resistance to anti-PD1 therapy in two well established poorly immunogenic murine tumor models.

Figure 70:
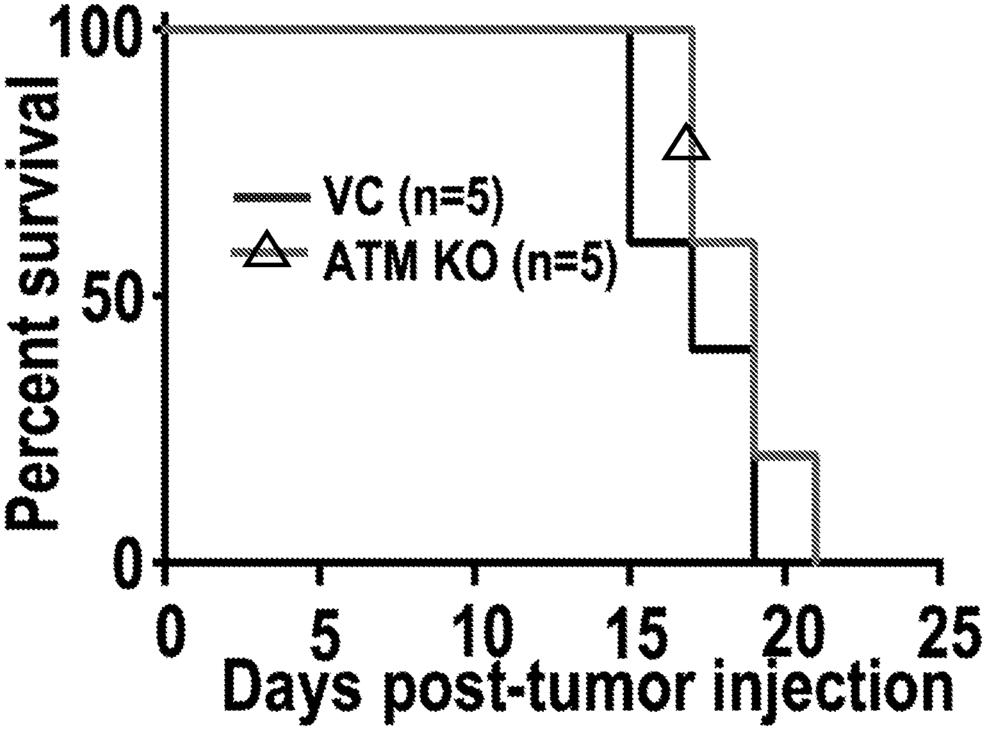
FIG. 70 presents a Kaplan-Meier survival curve of immunodeficient NSG mice inoculated with about $1\times10^5$ control or ATMKO 4T1 cells.

For FIGS. 19-28 described in this section, error bars represent standard error of the mean (SEM). *$p<0.05$, $p<0.01$, *$p<0.001$, **$p<0.0001$, ns, not significant, as determined by 2-way ANOVA (FIGS. 19, 21, 23, 25, and 27** *a, c, e, g* and *i*) or log-rank test (FIGS. 20, 22, 24, 26, 28). For FIGS. 68, FIG. 69 and FIG. 73, any error bars represent ±SEM. NS, not significant, was determined by unpaired t test (FIGS. 68 and 69) or log-rank test (FIG. 70).

Example 14

ATM Inhibition Promoted Intratumoral Lymphocyte Infiltration

Figure 29:
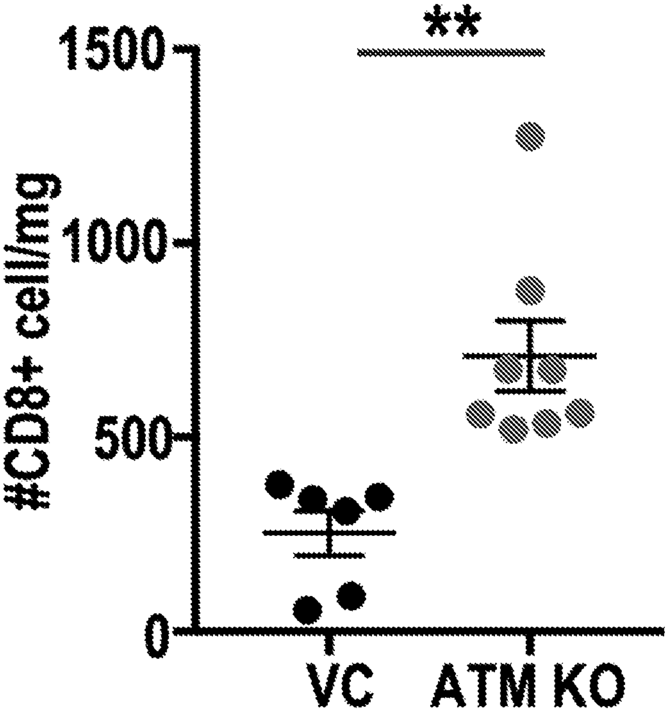
FIG. 29 presents average numbers of tumor-infiltrating $CD8^+$ T cells per mg of tissue from transplanted vector control (VC) or ATM KO B16F10 tumors grown in C57BL/6 mice. Flow cytometry analysis were done on day 13 post inoculation of $1\times10^5$ tumor cells. Data from two independent experiments.
Figure 30:
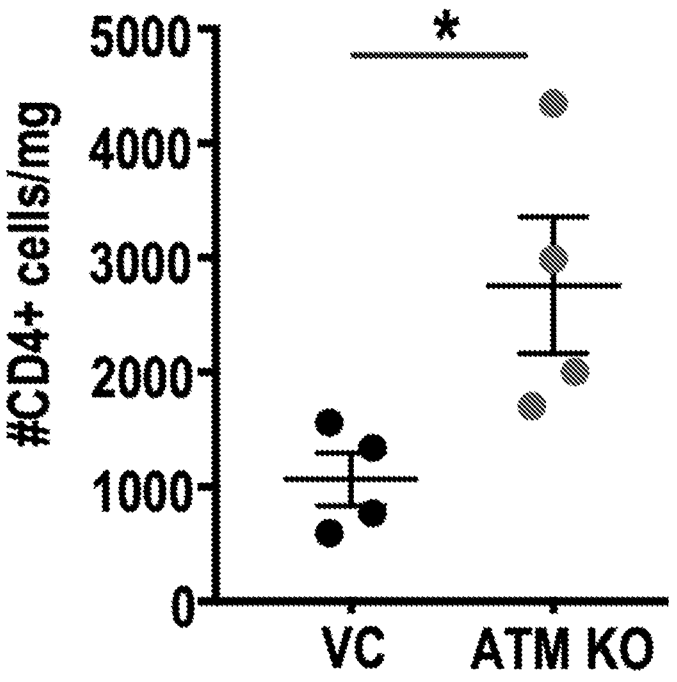
FIG. 30 presents average numbers of tumor-infiltrating $CD4^+$ T cells per mg of tissue from transplanted vector control (VC) or ATM KO B16F10 tumors grown in C57BL/6 mice. Flow cytometry analysis were done on day 13 post inoculation of $1\times10^5$ tumor cells. Data from two independent experiments.
Figure 31:
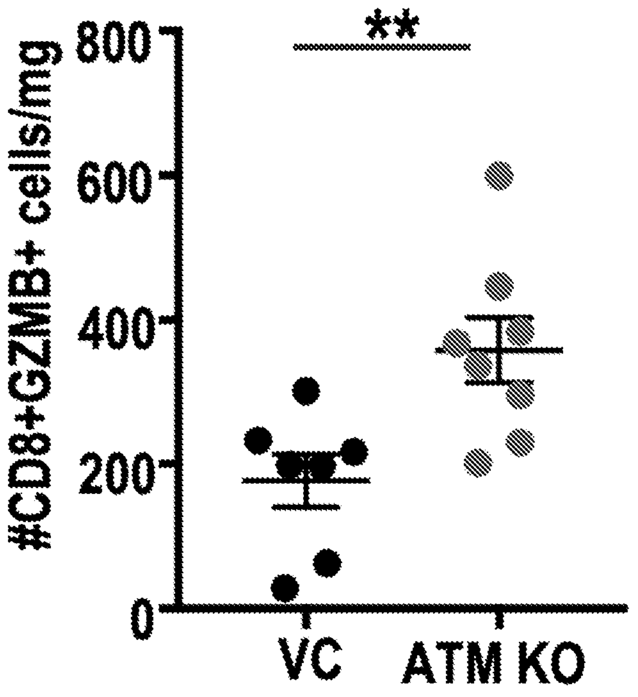
FIG. 31 presents average numbers of tumor-infiltrating $GZMB^+$ $CD8^+$ T cells per mg of tissue from transplanted vector control (VC) or ATM KO B16F10 tumors grown in C57BL/6 mice. Flow cytometry analysis were done on day 13 post inoculation of $1\times10^5$ tumor cells. Data from two independent experiments.
Figure 32:
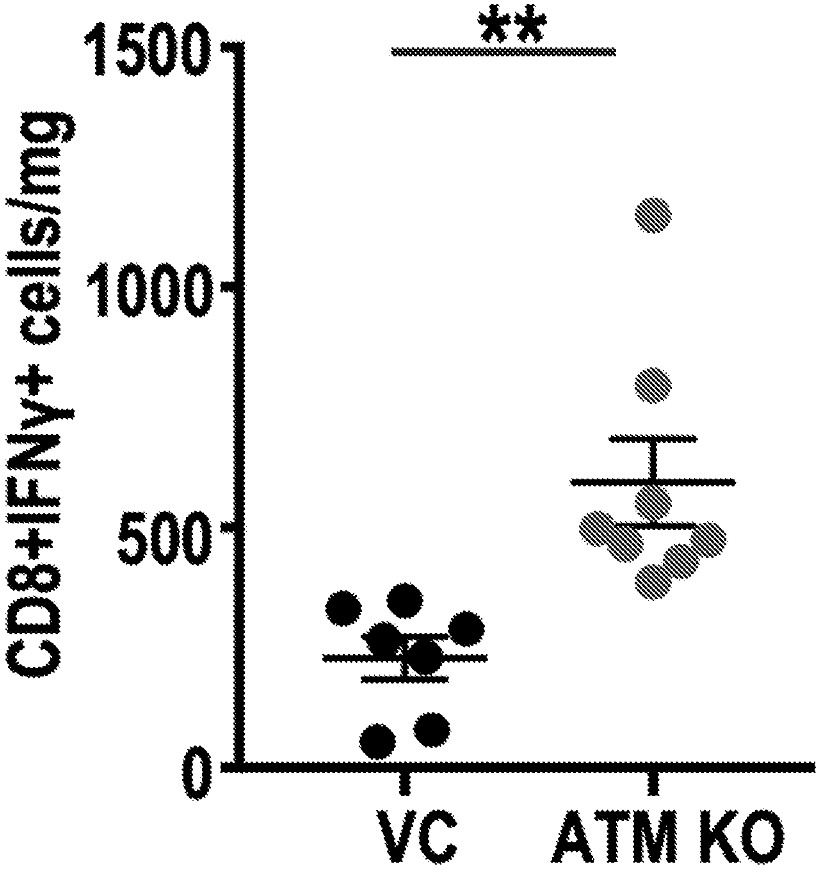
FIG. 32 presents average numbers of tumor-infiltrating $IFN\gamma^+CD8^+$ T cells per mg of tissue from transplanted vector control (VC) or ATM KO B16F10 tumors grown in C57BL/6 mice. Flow cytometry analysis were done on day 13 post inoculation of $1\times10^5$ tumor cells. Data from two independent experiments.
Figure 33:
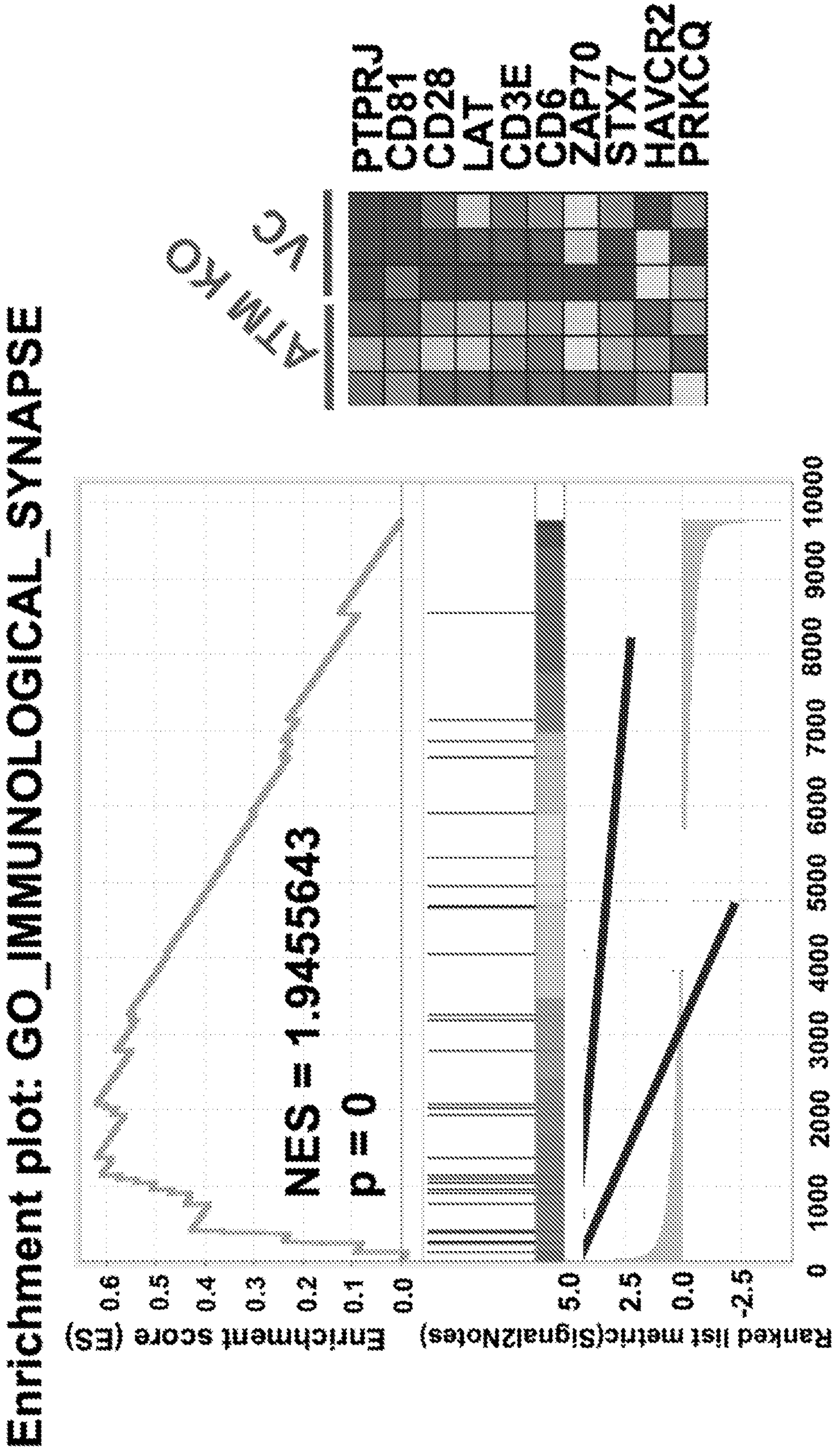
FIG. 33 presents gene set enrichment analysis (GSEA) of immunological pathway from B16 ATM KO tumors compared with vector control tumors. FDR calculated using GSEA.
Figure 34:
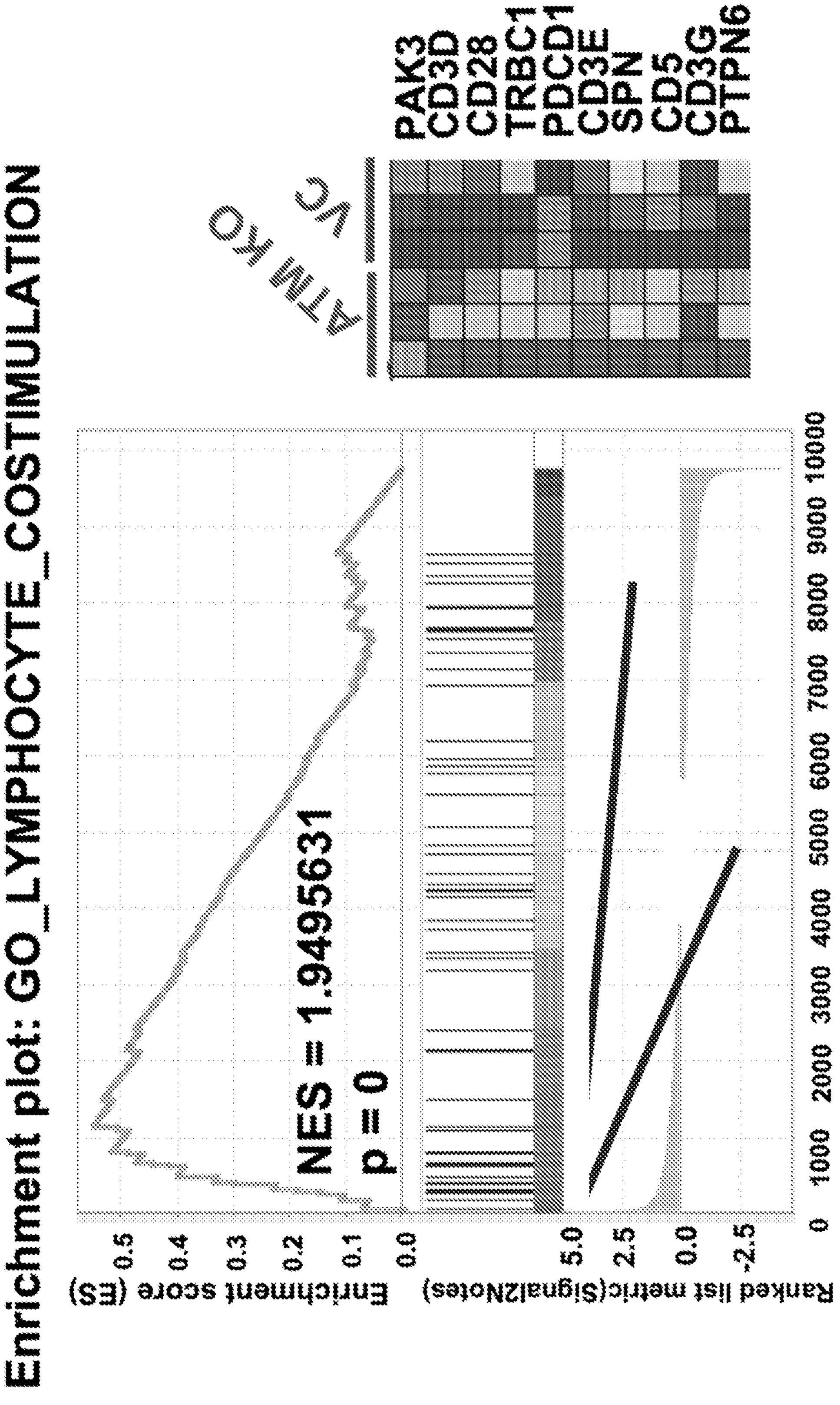
FIG. 34 presents gene set enrichment analysis (GSEA) of immunological pathway from B16 ATM KO tumors compared with vector control tumors. FDR calculated using GSEA.
Figure 35:
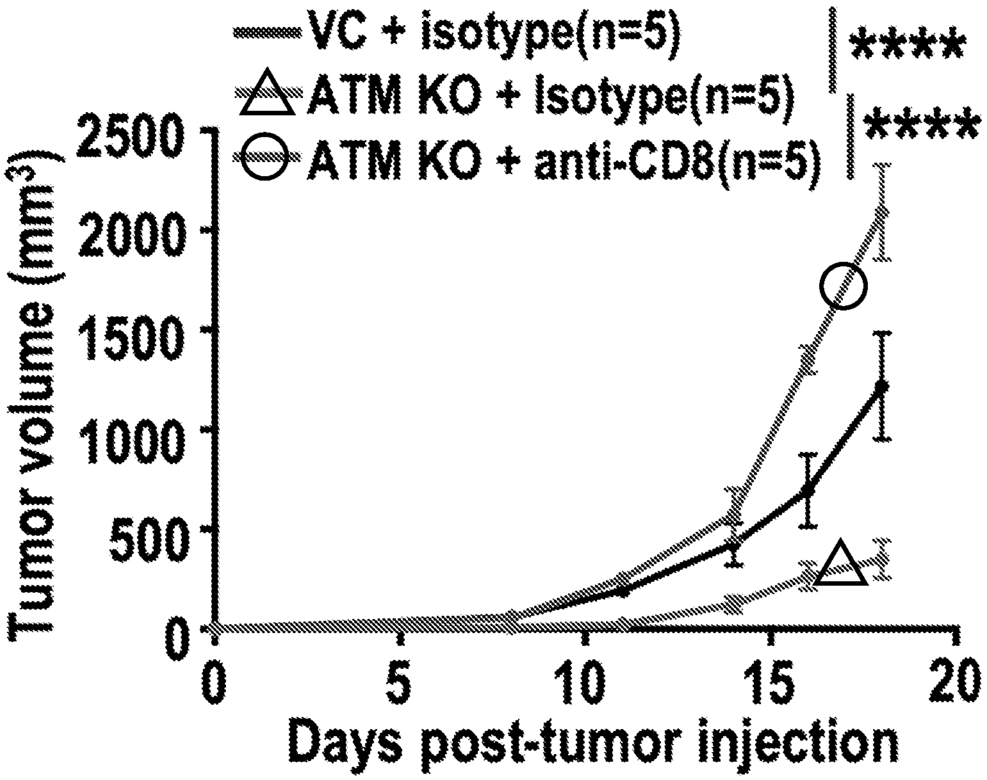
FIG. 35 presents tumor volume of C57BL/6 mice inoculated with about $1\times10^5$ vector control or ATMKO B16F10 cells and treated with 100 μg/mouse anti-CD8 or isotype control on days 1, 4, 7.
Figure 74:
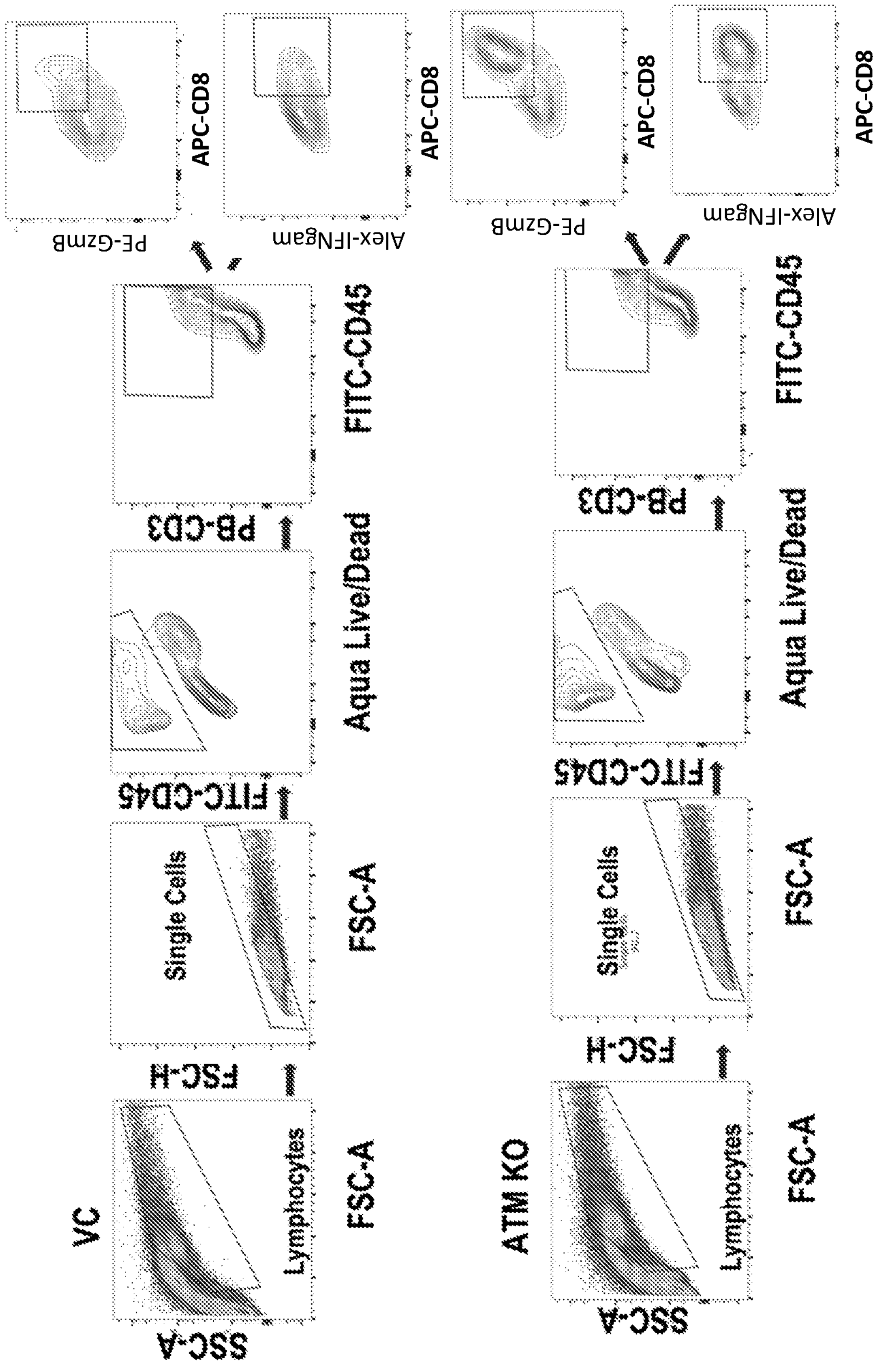
FIG. 74 presents gating strategy and representative flow cytometry plots for the quantification of $CD8^+$ T cells, $GzmB^+CD8^+$ and $IFN\gamma^+CD8^+$ T cells in vector control (VC) and ATM KO B16 tumors.
Figure 75:
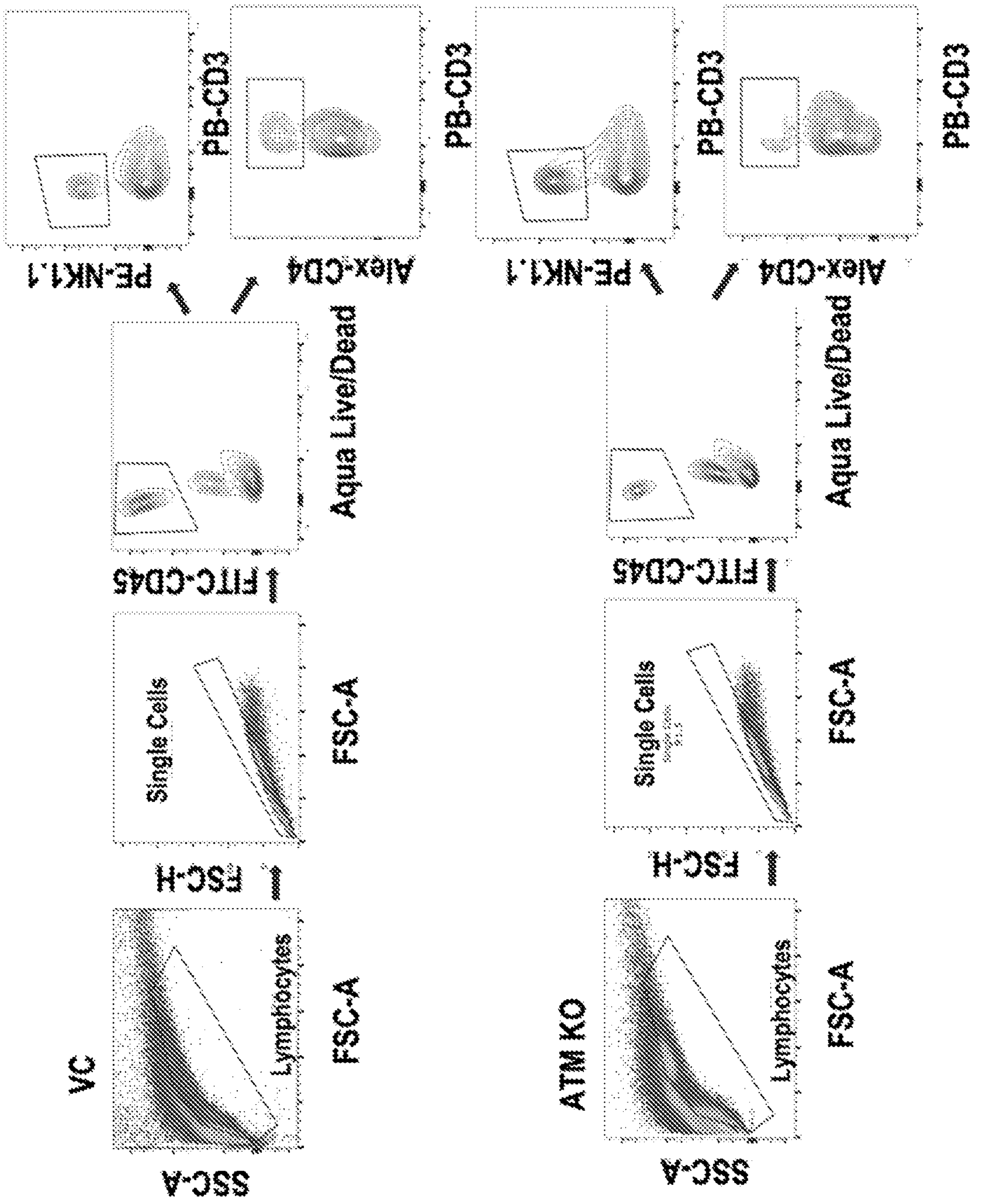
FIG. 75 presents gating strategy and representative flow cytometry graphs for the assessment of $CD4^+$ T cells and NK cells in vector control (VC) and ATM KO B16 tumors.
Figure 76:
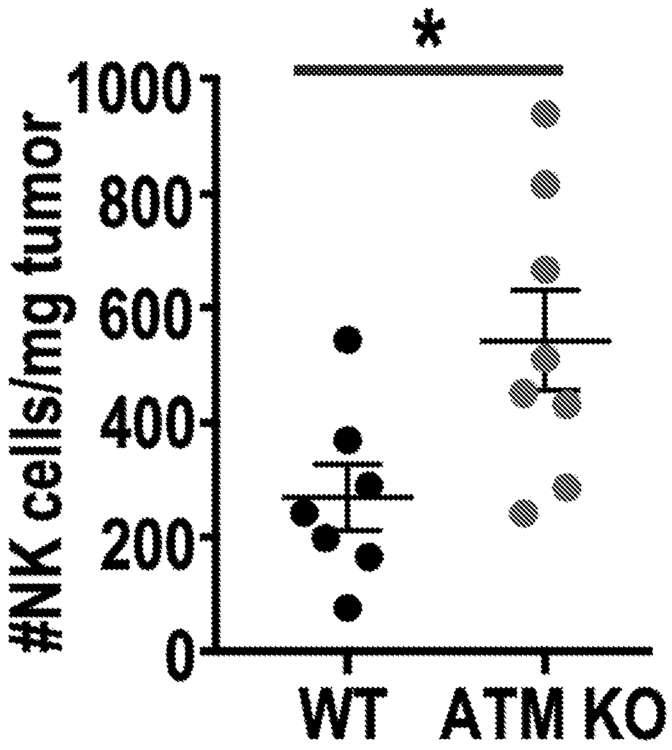
FIG. 76 presents average numbers of tumor-infiltrating $NK1.1^+$ NK cells per mg of tumor tissue in vector control (VC) and ATM KO B16F10 tumors grown in C57BL/6 mice. Tumors were analyzed by flow cytometry at day 13 post implantation. Data are aggregated from two independent experiments.
Figure 77:
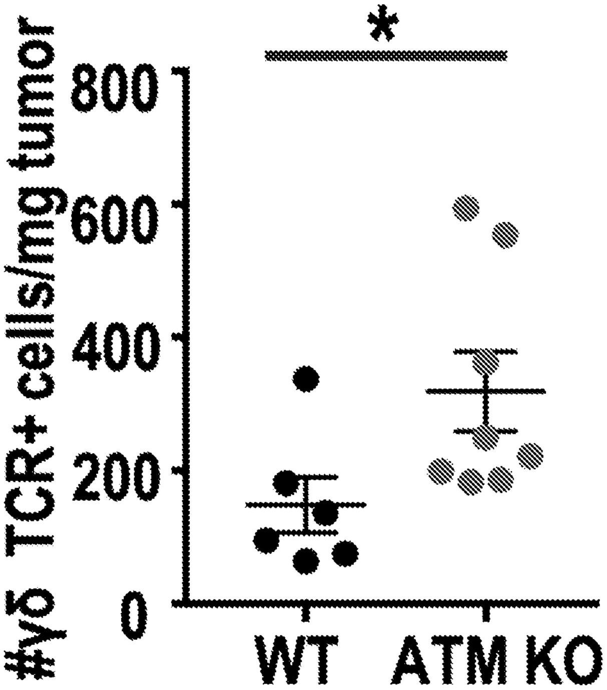
FIG. 77 presents average numbers of tumor-infiltrating F4-80 macrophages per mg of tumor tissue in vector control (VC) and ATM KO B16F10 tumors grown in C57BL/6 mice. Tumors were analyzed by flow cytometry at day 13 post implantation. Data are aggregated from two independent experiments.
Figure 78:
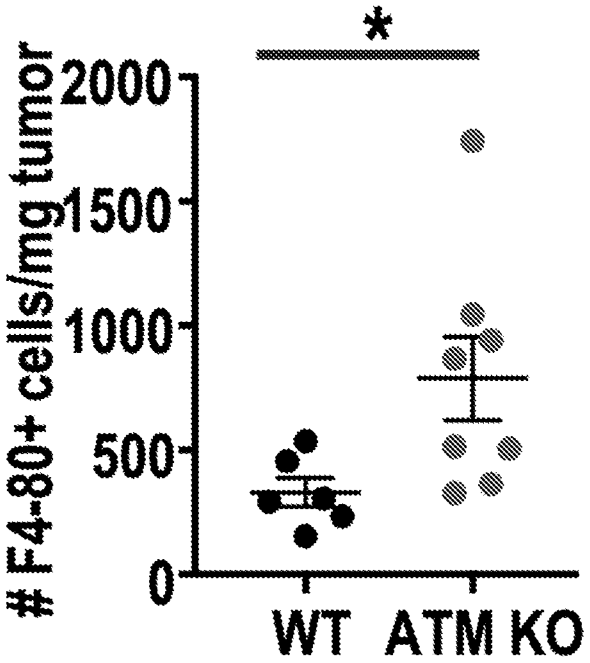
FIG. 78 presents average numbers of tumor-infiltrating γδTCR+ T cells per mg of tumor tissue in vector control (VC) and ATM KO B16F10 tumors grown in C57BL/6 mice. Tumors were analyzed by flow cytometry at day 13 post implantation. Data are aggregated from two independent experiments.
Figure 79:
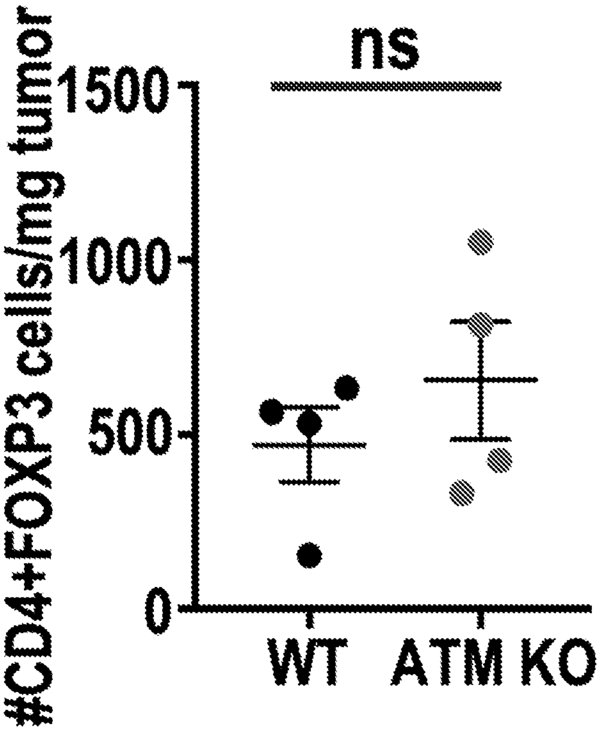
FIG. 79 presents average numbers of tumor-infiltrating $FOXP3^+$ Treg cells per mg of tumor tissue in vector control (VC) and ATM KO B16F10 tumors grown in C57BL/6 mice. Tumors were analyzed by flow cytometry at day 13 post implantation. Data are aggregated from two independent experiments.
Figure 82:
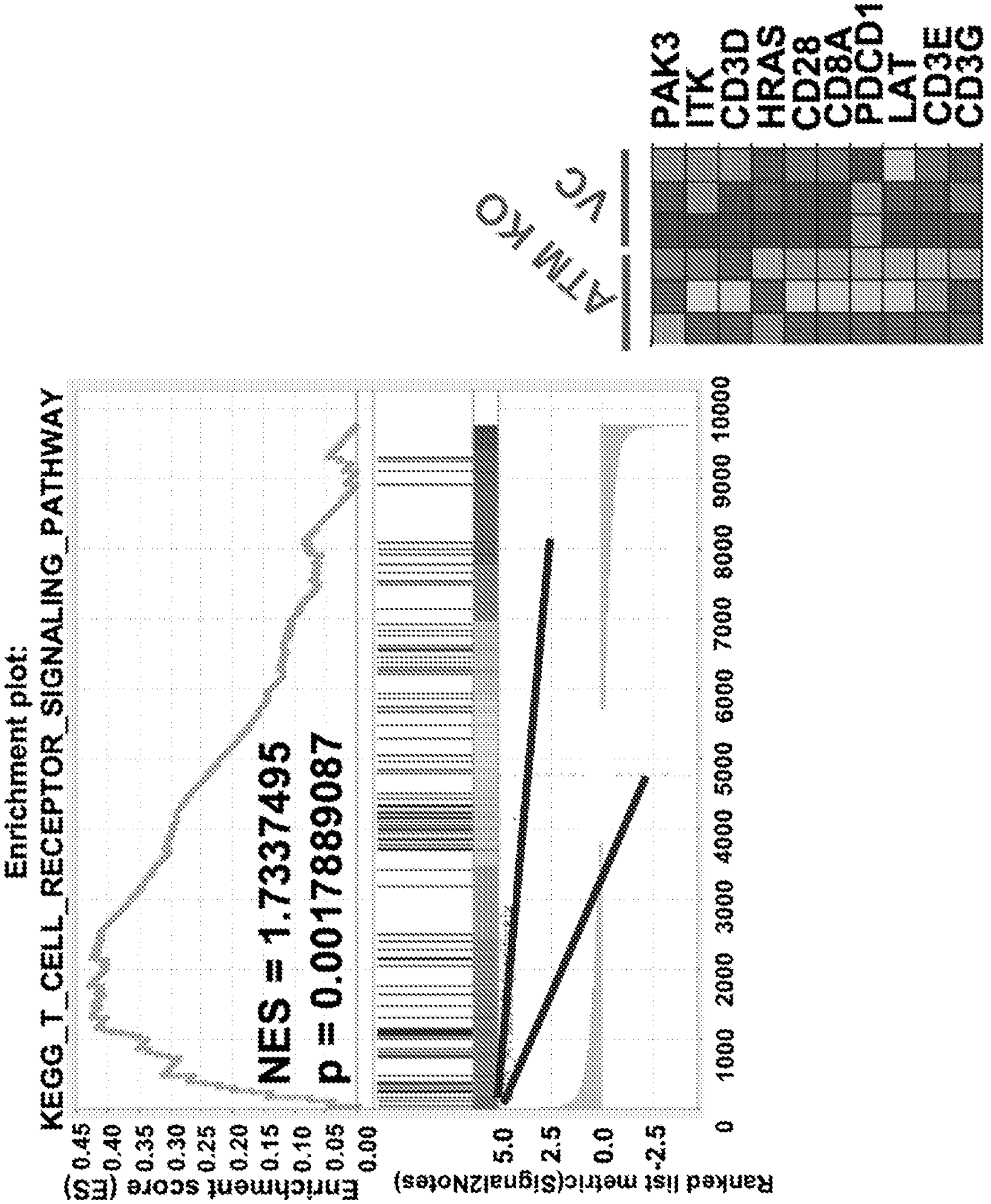
FIG. 82 presents gene set enrichment analysis (GSEA) of immunological pathway from B16 ATM KO tumors compared with vector control tumors. FDR calculated using GSEA.
Figure 83:
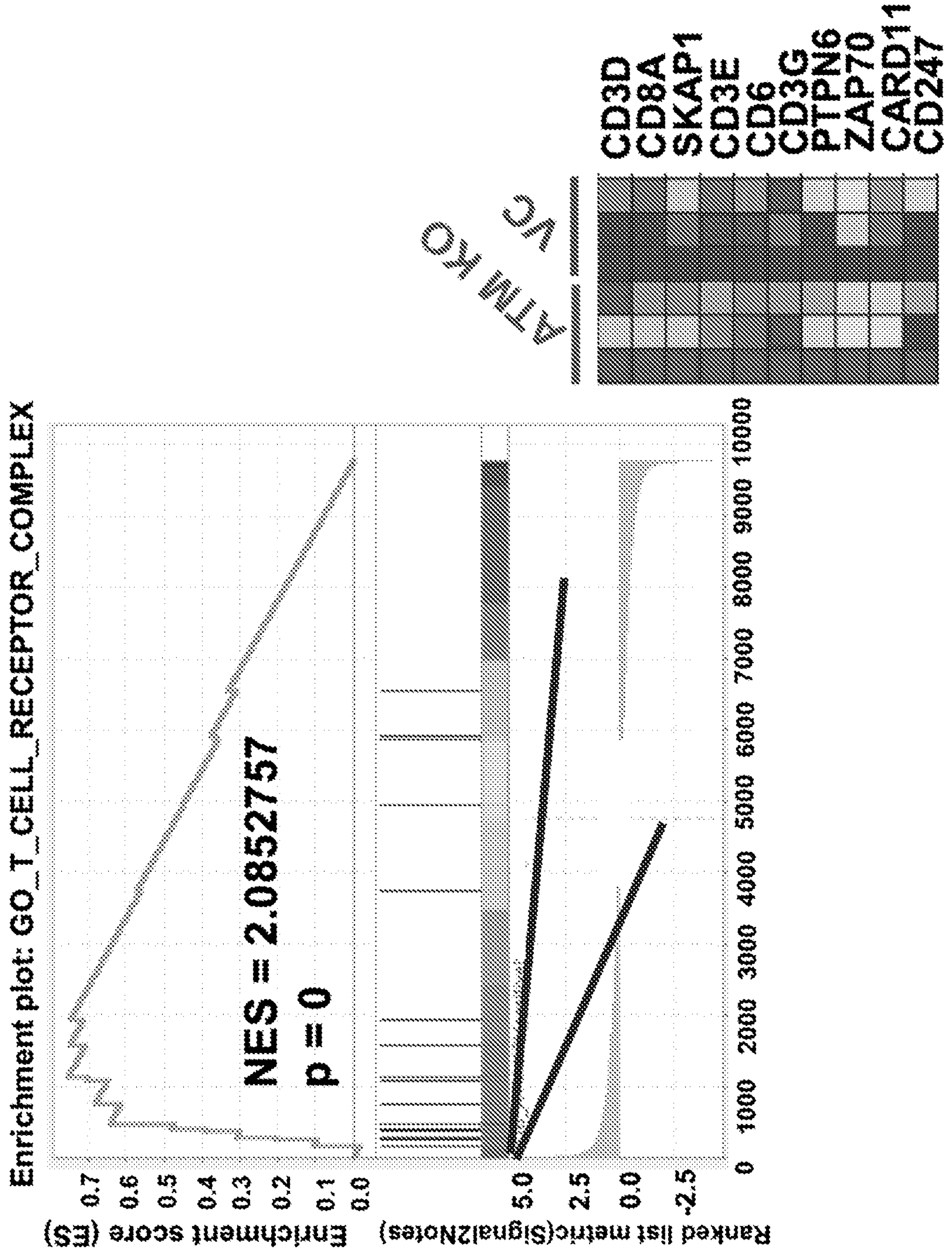
FIG. 83 presents gene set enrichment analysis (GSEA) of immunological pathway from B16 ATM KO tumors compared with vector control tumors. FDR calculated using GSEA.
Figure 84:
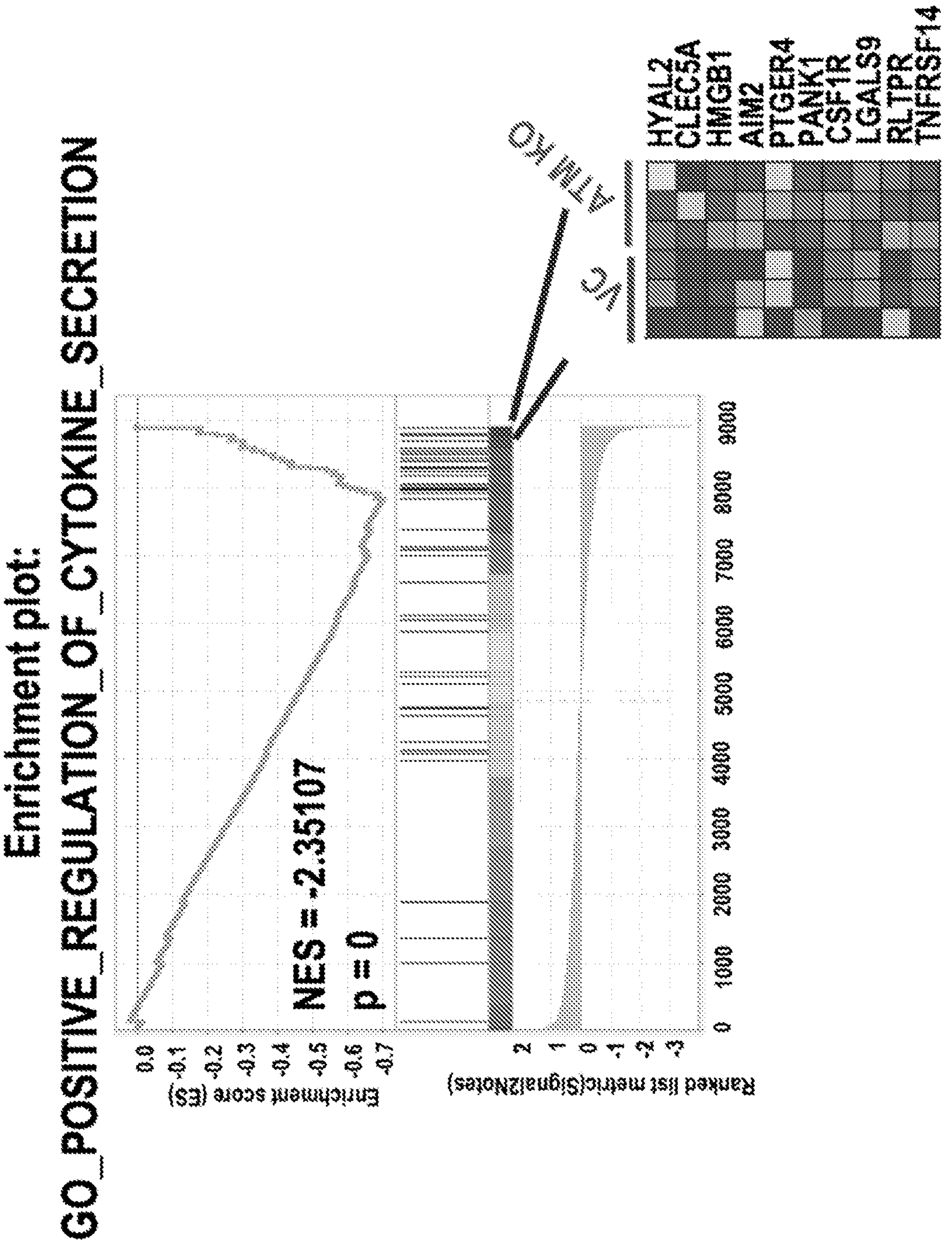
FIG. 84 presents gene set enrichment analysis (GSEA) of immunological pathways in 4T1 ATM KO cells vs vector control (VC) tumors. FDR calculated using GSEA.

As the efficacy of ICB therapy was shown to be associated with tumor infiltrating lymphocytes (TILs; Taube, J. M. et al. *Clin Cancer Res* (2014) doi:10.1158/1078-0432.CCR-13-3271), we therefore assessed if ATM inhibition can boost lymphocytes infiltration. Then we analyzed the tumor-infiltrating lymphocytes (TILs) in vector control and ATM-deficient B16F10 tumors by flow cytometry analysis (FIGS. 74, 75). We found a significant increase in CD8+ and $CD4^+$ T cell infiltration in ATM-deficient B16F10 tumors when compared with control tumors (FIGS. 29, 30). Furthermore, we also found increased levels of Granzyme-$B^+$ ($GzmB^+$) $CD8^+$, and $IFN\gamma^+$ $CD8^+$T cells, both indicators of activated cytotoxic T cells in ATM-deficient B16F10 tumors when compared with vector control tumors (FIGS. 31, 32). In addition, we also discovered that ATM deficiency enhanced infiltration of NK1.$1^+$ (NK cells) (FIG. 76), F4/$80^+$ (macrophage), and $\gamma\delta^+$($\gamma\delta$T cells) cells intratumorally when compared to vector control tumors (FIGS. 77, 78). In contrast, there were no significant increase in $CD4^+Foxp3^+$ Treg cells in ATM deficient tumors (FIG. 79). We further conducted transcriptomic profiling of control and ATM deficient B16F10 tumors. Gene set enrichment analysis (GSEA) analysis of our RNAseq results indicated that several important signaling pathways, including immune synapse (FIG. 33), lymphocyte co-stimulation (FIG. 34), and T-cell receptor signaling (FIG. 82, 83) were significantly enriched in ATM-deficient tumors.

Figure 80:
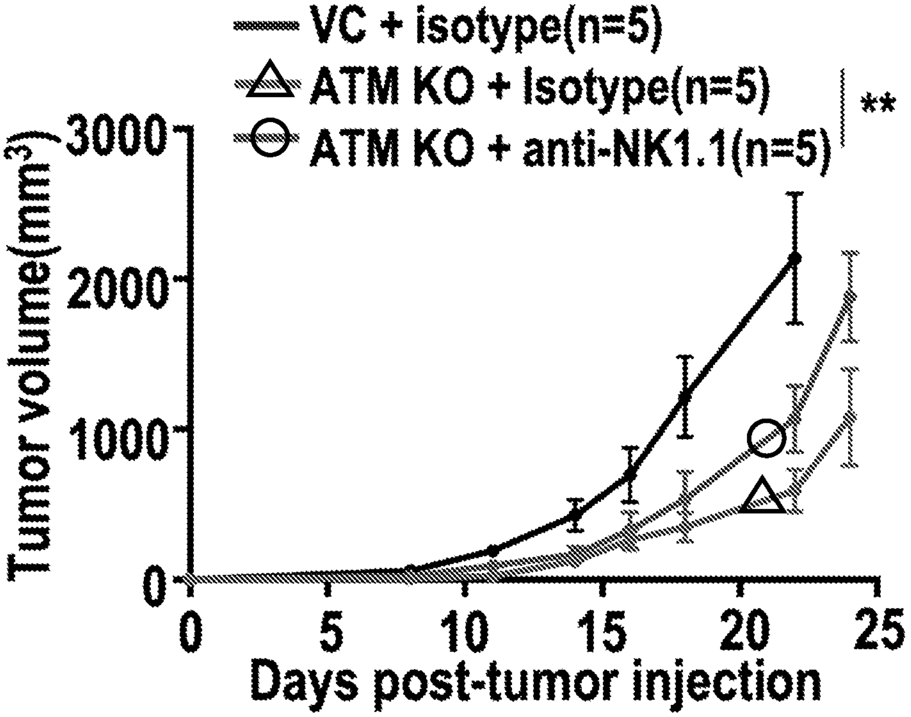
FIG. 80 presents tumor volume of C57BL/6 mice inoculated with about $1\times10^5$ vector control (VC) or ATM knockout B16F10 cells and treated with 100 μg/mouse anti-NK1.1 or isotype control on days 1, 4, 7.
Figure 81:
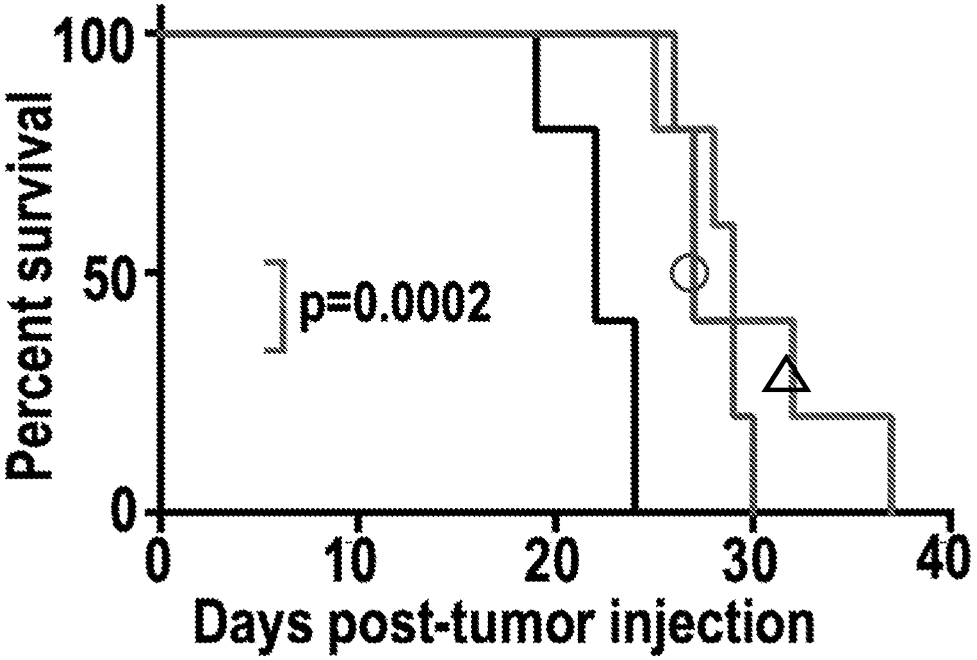
FIG. 81 presents Kaplan-Meier survival curve of C57BL/6 mice inoculated with about $1\times10^5$ vector control (VC) or ATM knockout B16F10 cells and treated with 100 μg/mouse anti-NK1.1 or isotype control on days 1, 4, 7. Collectively.

In order to determine the relative importance of different immune effector cells on the growth delay observed in ATM-deficient B16F10 tumors, we used well-established antibody-based methods to deplete $CD8^+$ T cells, $CD4^+$ T cells, and NK cells. Our results indicated that depletion of $CD8^+$ T cells or $CD4^+$ T cells significantly or completely abrogated the tumor growth delay in ATM-deficient B16F10 tumors, respectively (FIGS. 35, 36, 37, 38). In comparison, depletion of NK cells also had a statistically significant effect in attenuating tumor growth delay observed in ATM-deficient tumors (FIGS. 80, 81). Taken together, these results strongly suggested that ATM deficiency-induced tumor growth delay was dependent on intratumoral lymphocyte infiltration.

Figure 36:
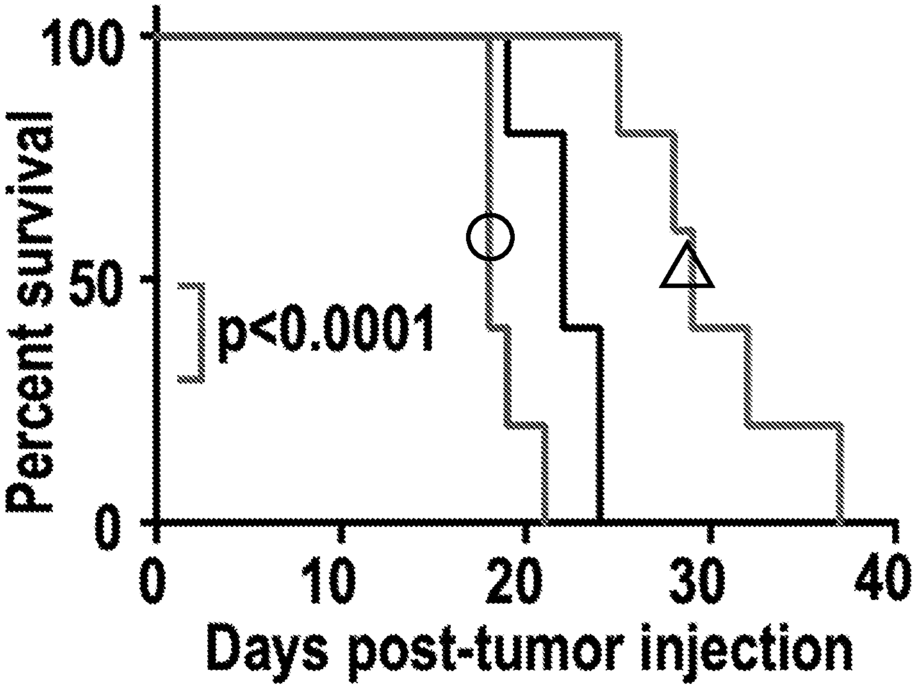
FIG. 36 presents Kaplan-Meier survival curve of C57BL/6 mice inoculated with about $1\times10^5$ vector control or ATMKO B16F10 cells and treated with 100 μg/mouse anti-CD8 or isotype control on days 1, 4, 7.
Figure 37:
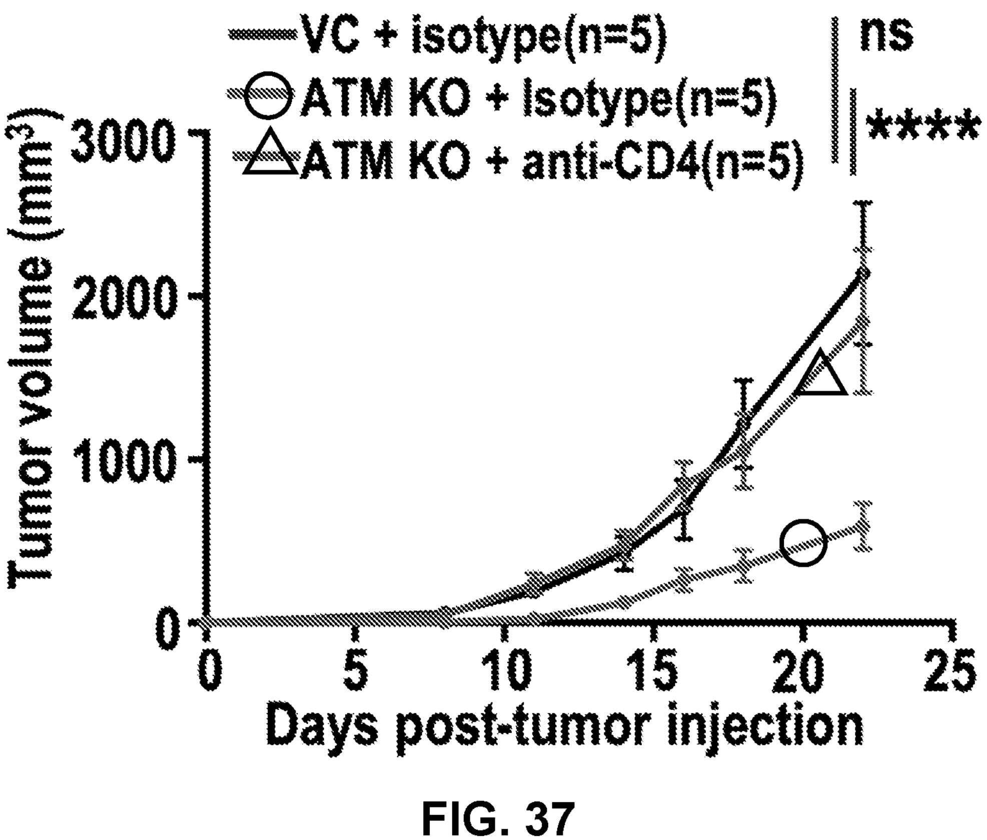
FIG. 37 presents tumor volume of C57BL/6 mice inoculated with about $1\times10^5$ vector control or ATMKO B16F10 cells and treated with 100 μg/mouse anti-CD4 or isotype control on days 1, 4, 7.
Figure 38:
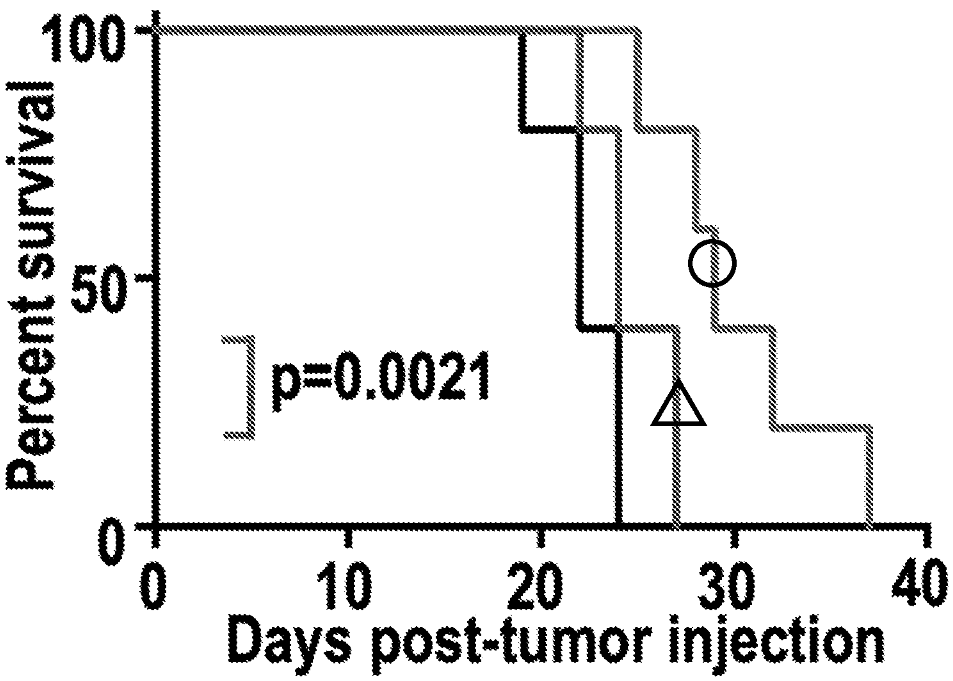
FIG. 38 presents Kaplan-Meier survival curve of C57BL/6 mice inoculated with about $1\times10^5$ vector control or ATMKO B16F10 cells and treated with 100 μg/mouse anti-CD4 or isotype control on days 1, 4, 7. Collectively, FIGS. 29-37 indicate that ATM inhibition enhances lymphocyte infiltration.
Figure 39:
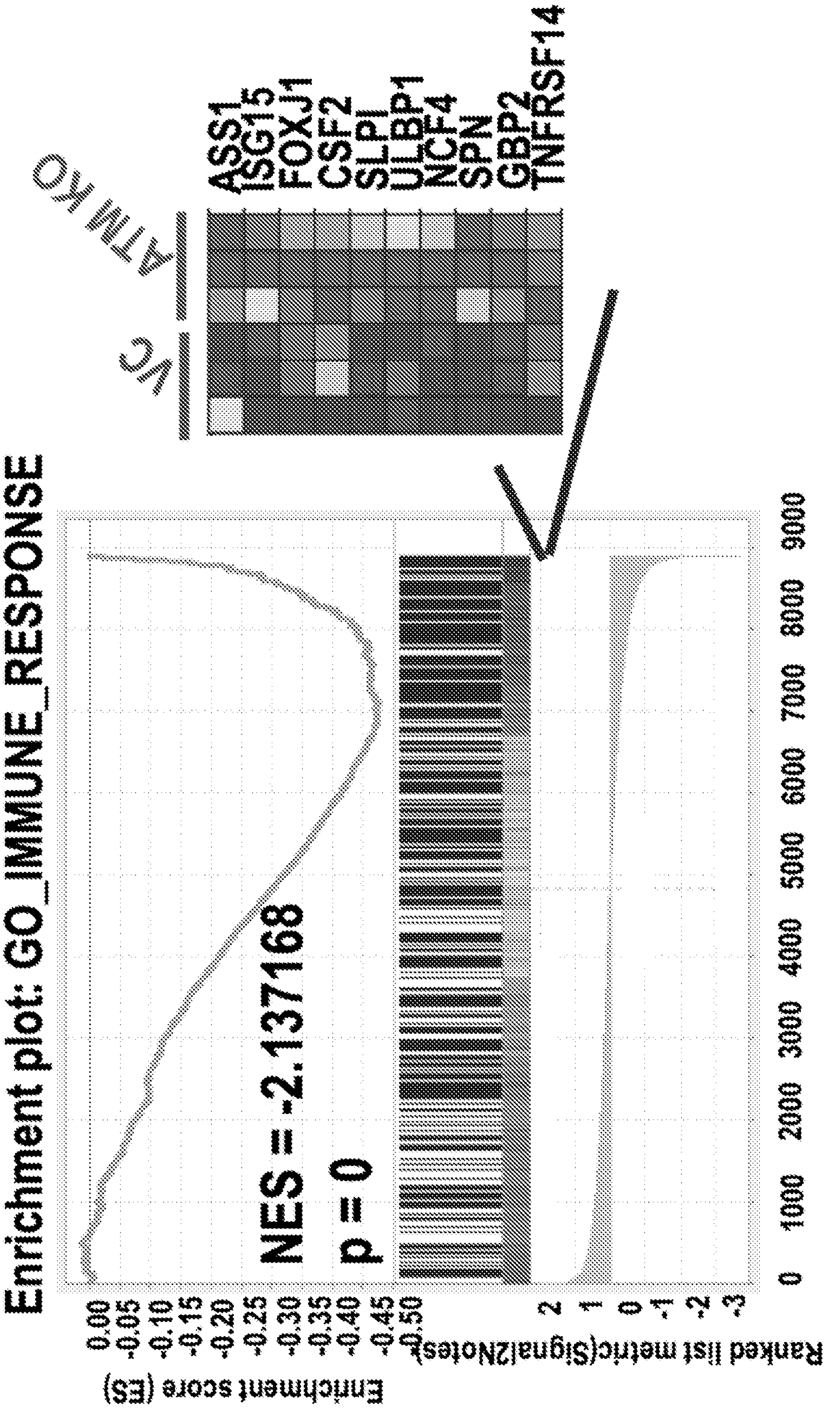
FIG. 39 presents gene set enrichment analysis (GSEA) of immunological pathways in 4T1 ATM KO cells vs vector control (VC) tumors. FDR calculated using GSEA.
Figure 40:
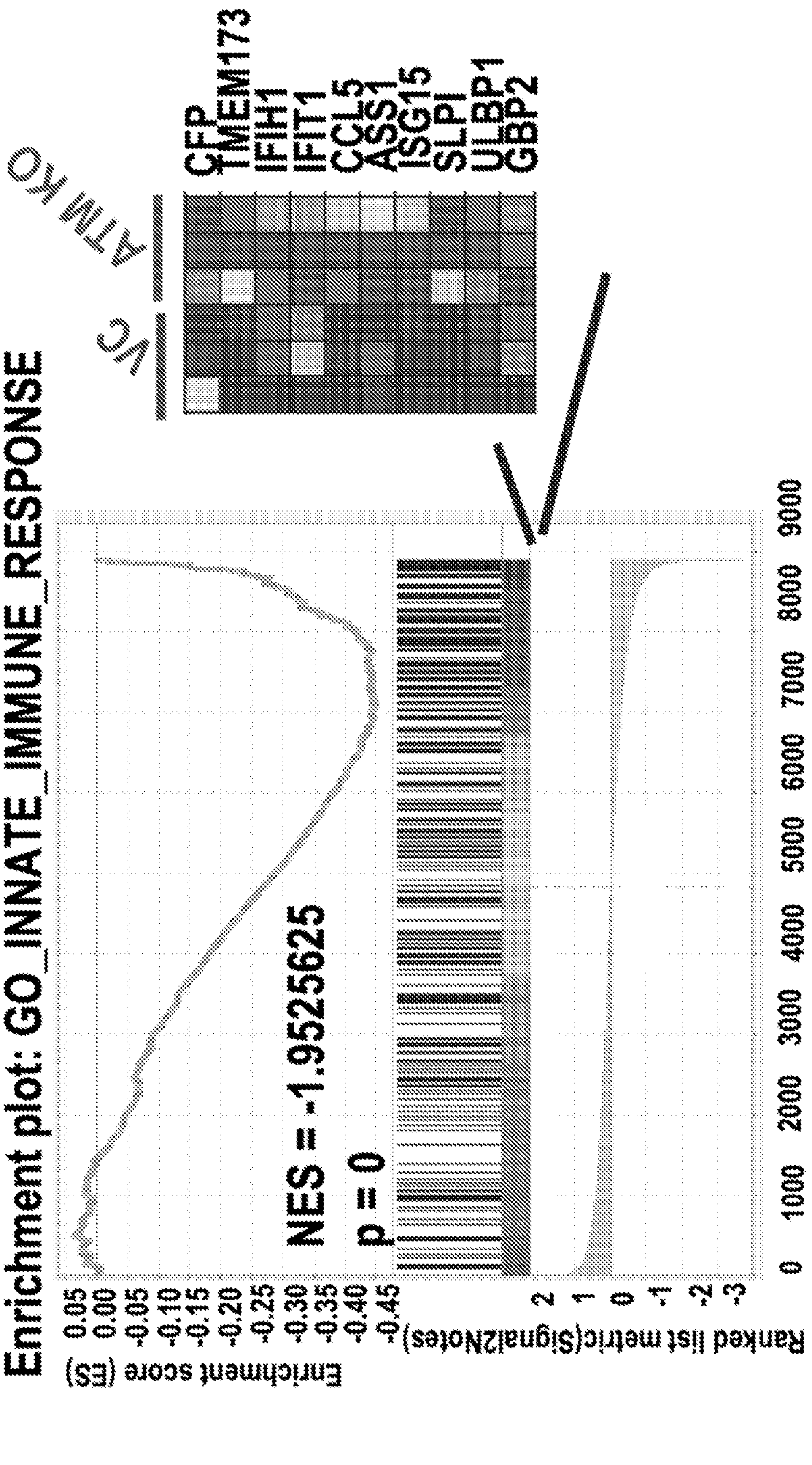
FIG. 40 presents gene set enrichment analysis (GSEA) of immunological pathways in 4T1 ATM KO cells vs vector control (VC) tumors. FDR calculated using GSEA.

For FIGS. 29-38 described in this section, error bars represent ±SEM. *$p<0.05$, $p<0.01$, *$p<0.001$, **$p<0.0001$, ns, not significant, as determined by unpaired t test (FIGS. 29-32, 33, 35) or log-rank test (FIGS. 36, 38). For FIG. 78 and FIG. 79**, error bars represent ±SEM. *$p<0.05$, $p<0.01$, *$p<0.001$, **$p<0.0001$, ns, not significant, as determined by unpaired t test (FIG. 78) or log-rank test (FIG. 79**).

Example 15

ATM Inhibition Activated the cGAS-STING Pathway

Figure 41:
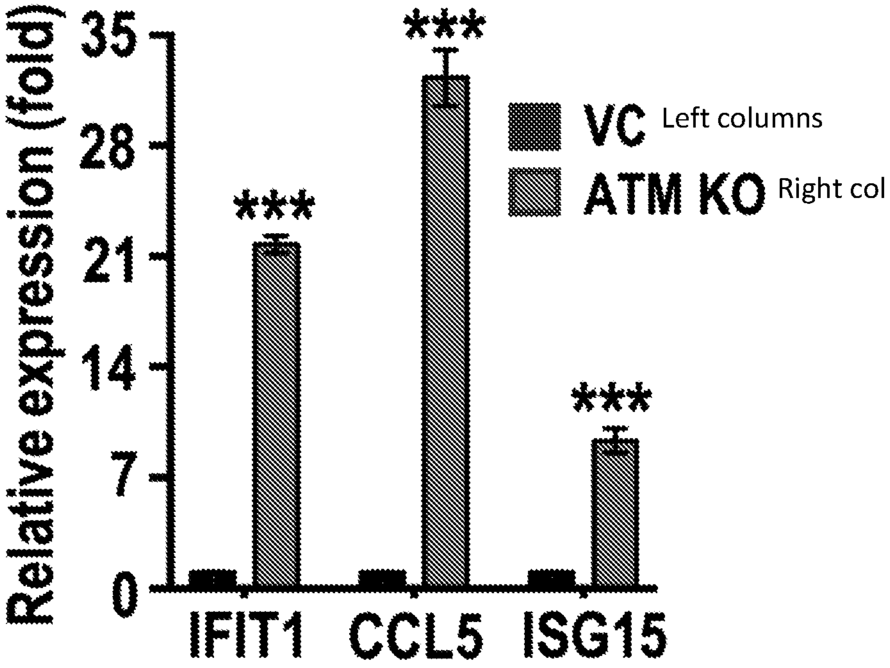
FIG. 41 presents the expression of IFIT1, CCL5 and ISG15 in vector control (VC) and ATM KO B16F10 cells analyzed by real-time qPCR.
Figure 42:
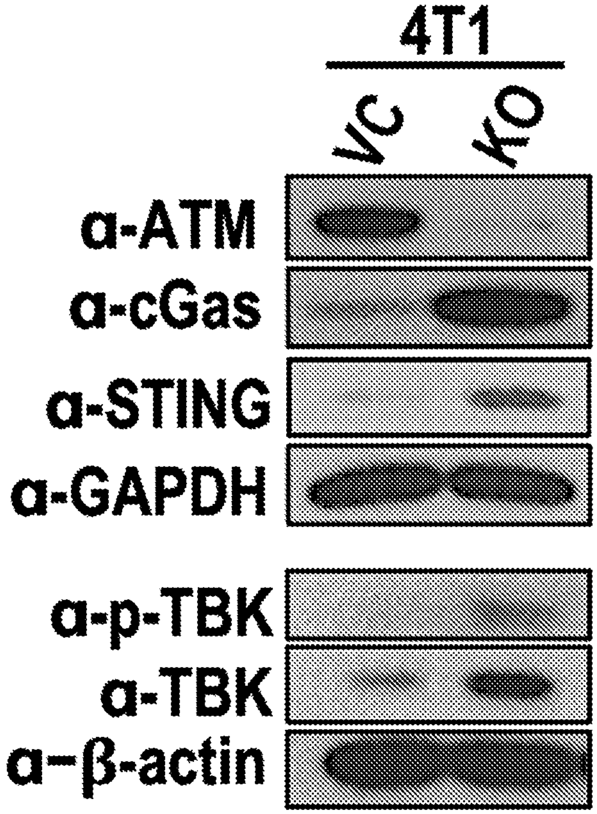
FIG. 42 presents western blot analysis of expression of cGas, STING, p-TBK, TBK in vector control (VC) and 4T1 cells. GAPDH or β-actin were used as protein loading controls.
Figure 43:
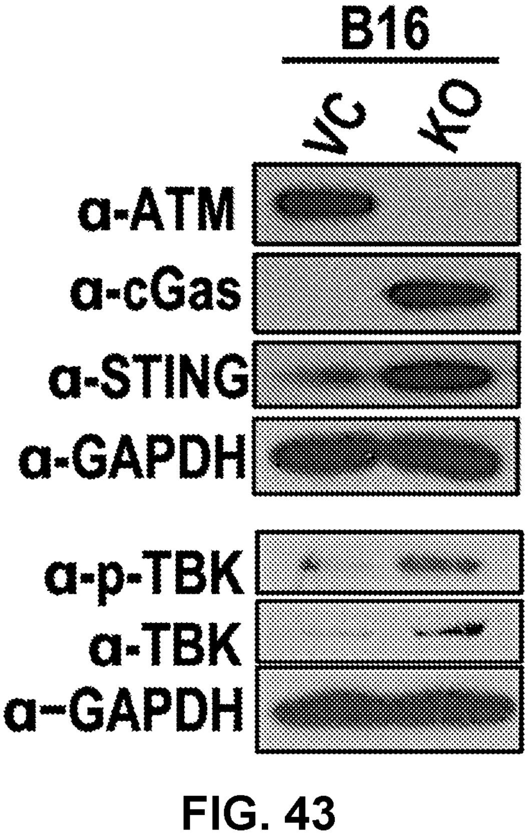
FIG. 43 presents western blot analysis of expression of cGas, STING, p-TBK, TBK in vector control (VC) and ATMKO B16F10 cells. GAPDH or β-actin were used as protein loading controls.
Figure 44:
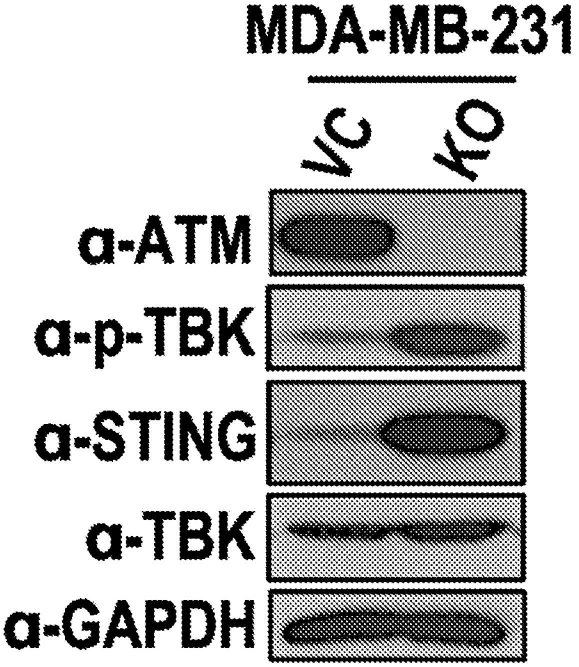
FIG. 44 presents western blot analysis of expression of cGas, STING, p-TBK, TBK in vector control (VC) and MDA-MB-231 cells. GAPDH or β-actin were used as protein loading controls.

We next investigated the molecular mechanisms involved in promoting TIL infiltration in ATM-deficient tumors. We first carried out GSEA analysis of RNAseq data of ATM-deficient 4T1 cells in vitro. Our data indicated that there was a significant enrichment of genes associated with innate cellular immune response in ATM-deficient 4T1 cells when compared with vector control cells (FIGS. 39, 40 and FIGS. 82-87). These data were consistent with earlier data suggesting ATM involvement in regulating cellular innate immunity (Petersen, A. J., et al. *Proc Natl Acad Sci* (2012), doi:10.1073/pnas.1110470109; Hartlova, A. et al. *Immunity* (2015), doi:10.1016/j.immuni.2015.01.012). One important pathway from GSEA analysis was the cGAS-STING pathway (FIG. 40; Chen, Q., et al. *Nat Immunol* (2016) doi:10.1038/ni.3558; Sun, L., et. al. Science (2013) doi:10.1126/science.1232458; Wu, J. et al. Science (2013) doi:10.1126/science.1229963). While cGAS-STING activation appeared to stimulate an interferon response synergized with anti-PD1 therapy (Wang, H. et al. *Proc Natl Acad Sci USA* (2017) doi:10.1073/pnas.1621363114), we examined the pathway more carefully in ATMKO cells. ATM-deficiency-induced mRNA expression of interferon-stimulated genes (ISGs) downstream of cGAS-STING: IFIT1, ISG15, and CCL5 (FIG. 41). In addition, Western blot analysis showed that protein levels of cGas, p-TBK and TBK increased significantly in ATM-deficient 4T1 breast cancer cell (FIG. 42), B16F10 melanoma (FIG. 43), and human breast cancer MDA-MB-231 cells (FIG. 44). Besides genetic inactivation of ATM, we further examined if chemical inhibitors of ATM, AZD1390 and Ku55933, could induce expression of ISGs.

Figure 45:
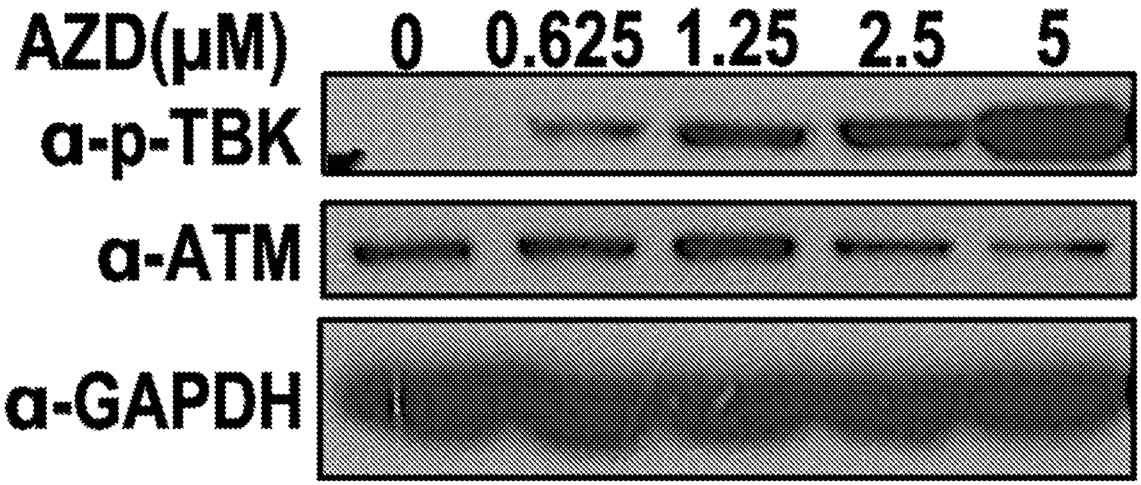
FIG. 45 presents western blot analysis of p-TBK levels in B16 cells treated with AZD1390 at indicated concentrations for 48 hrs.
Figure 46:
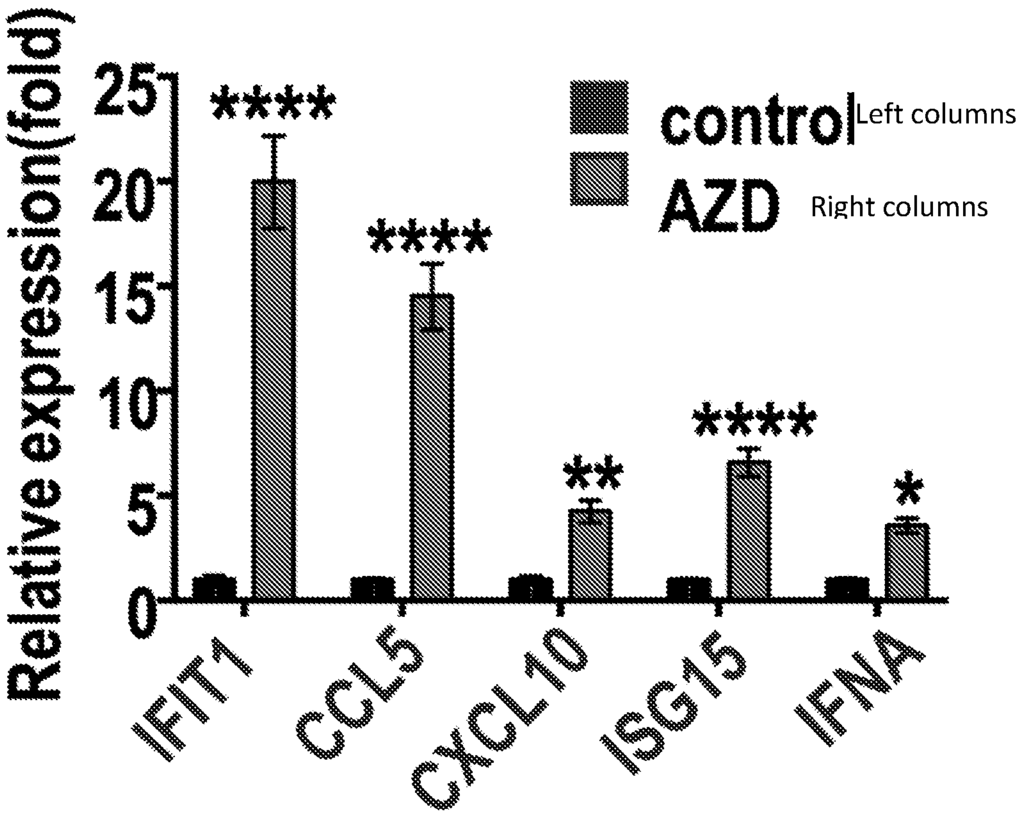
FIG. 46 presents transcription levels of IFNs and ISGs in B16 cells treated with 1 μM AZD1390 for 48 hrs and analyzed by Q-RT PCR.
Figure 88:
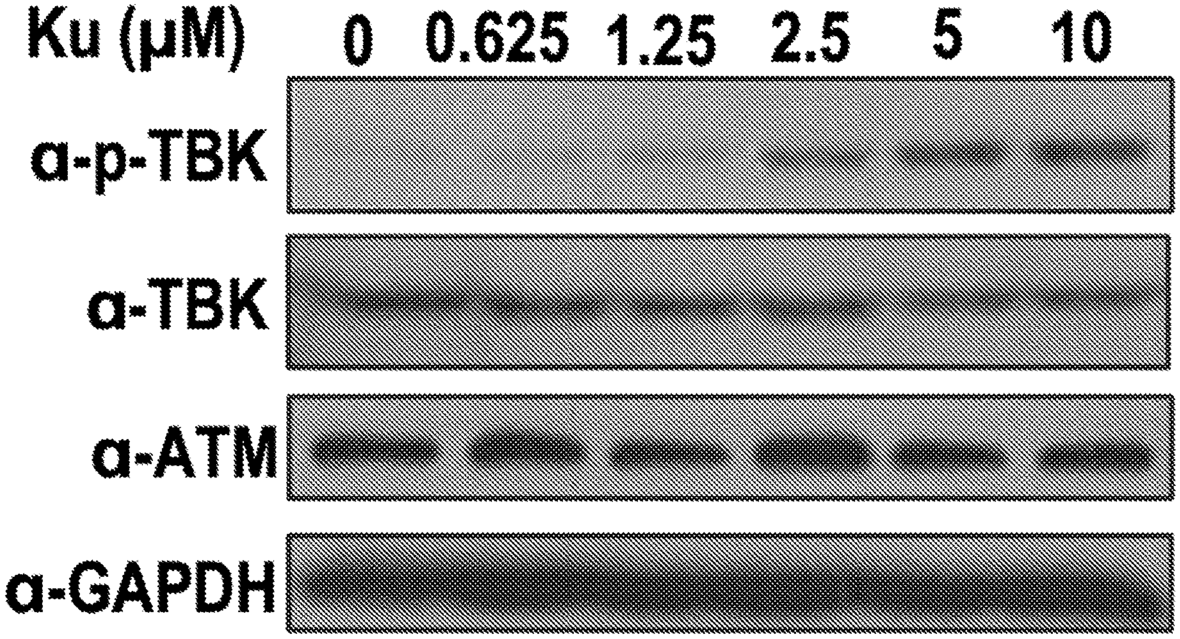
FIG. 88 presents western blot analysis of p-TBK and TBK in B16 cells treated with Ku55933 at indicated concentrations for 6 hours.
Figure 89:
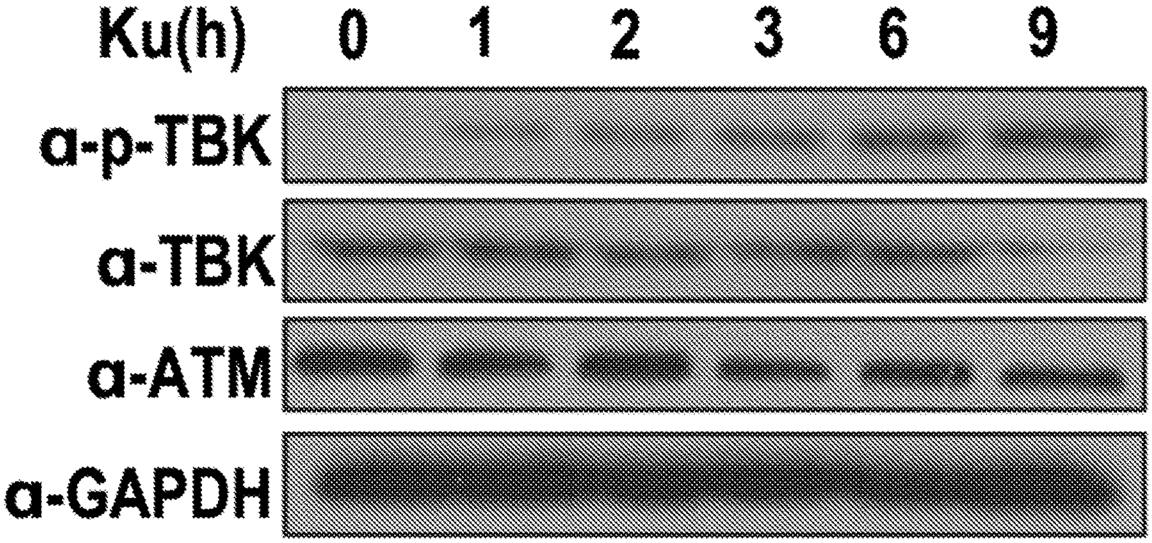
FIG. 89 presents western blot analysis of p-TBK and TBK in B16 cells treated with 5 μM Ku55933 at indicated times.
Figure 90:
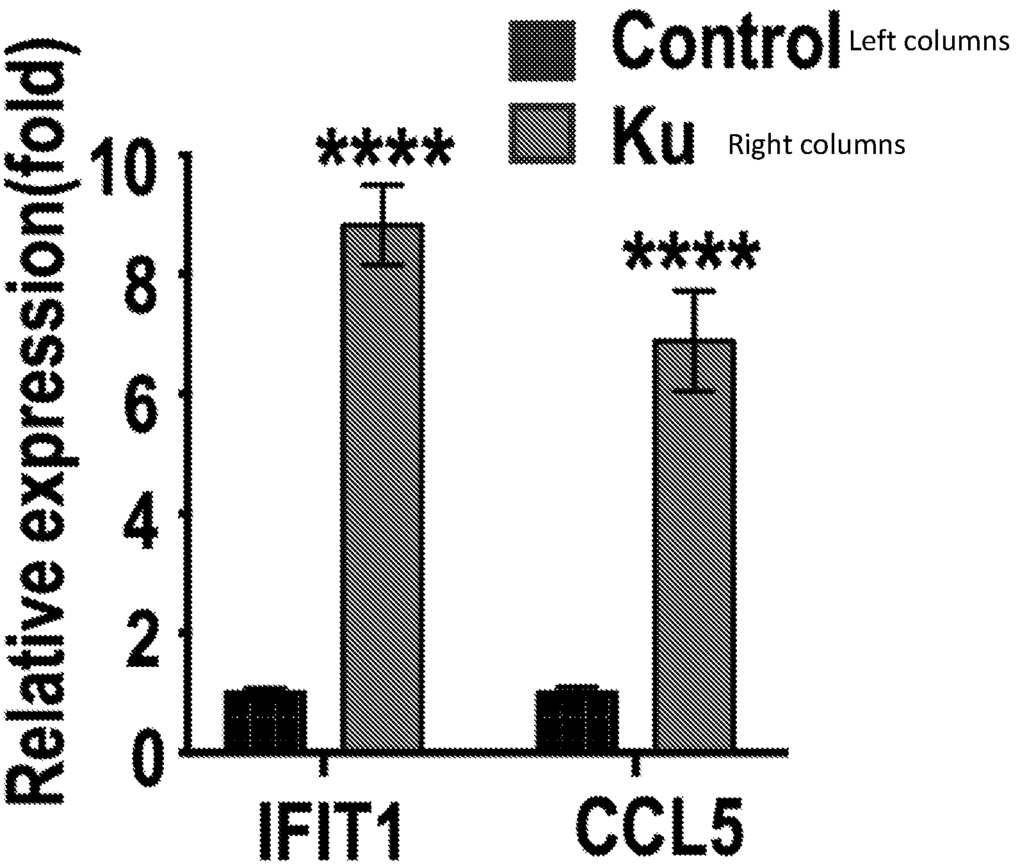
FIG. 90 presents transcription levels of IFIT1 and CCL5 in B16 cells treated with 10 μM Ku55933 for 9 hours and analyzed by real-time PCR. Error bars represent SEM. ***$p<0.001$, as determined by 2-way ANOVA.
Figure 91:
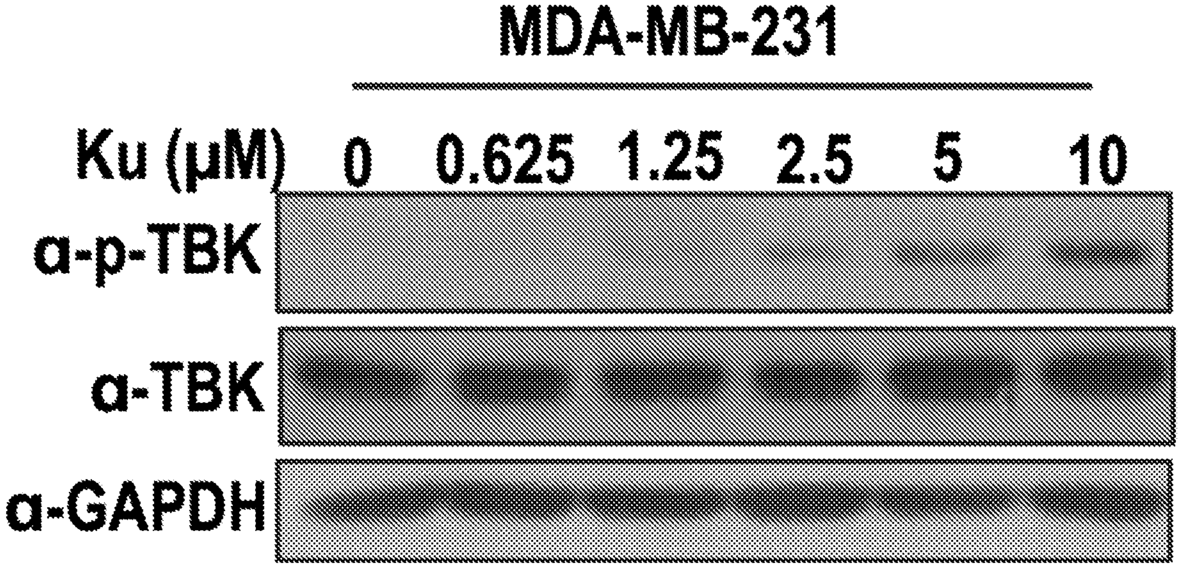
FIG. 91 presents western blot analysis of p-TBK and TBK in human MDA-MB-231 cells treated with Ku55933 for 6 hours.

Western blot analysis indicated that AZD1390 (FIG. 45) and Ku55933 (FIGS. 88, 89) induced increased phosphorylation of TBK. Consistent with western blot data, qRT-PCR analysis showed that AZD1390 (FIG. 46) and Ku55933 (FIG. 90) treatment also induced expression of ISGs in B16F10 cells. Furthermore, the latter also induced expression of p-TBK in human MDA-MB-231 cell line (FIG. 91). These data therefore demonstrated that chemical inhibition of ATM could induce the activation of cGas-STING and downstream signaling, similar to genetic depletion.

Figure 47:
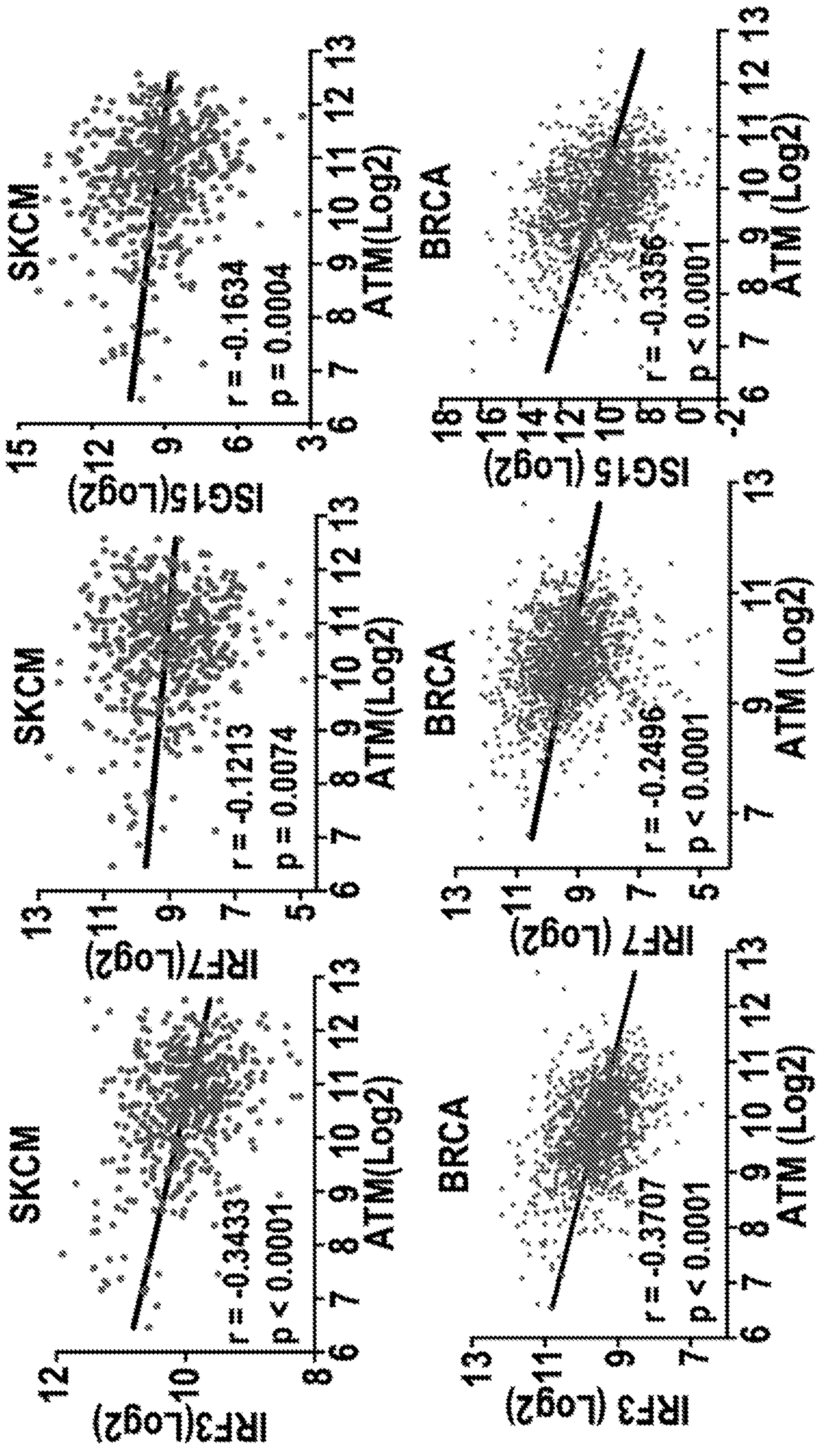
FIG. 47 presents correlation analysis for ATM expression level versus IRF3, IRF7, and ISG15 in human Skin Cutaneous Melanoma (SKCM, 472 samples) and Breast Invasive Carcinoma (BRCA, 1100 samples) from TCGA Pan Cancer Atlas. R and p represent Pearson correlation coefficients and two-tailed p values. Collectively, FIGS. 39-47 indicate that ATM inhibition enhances cGas-STING activation.
Figure 92:
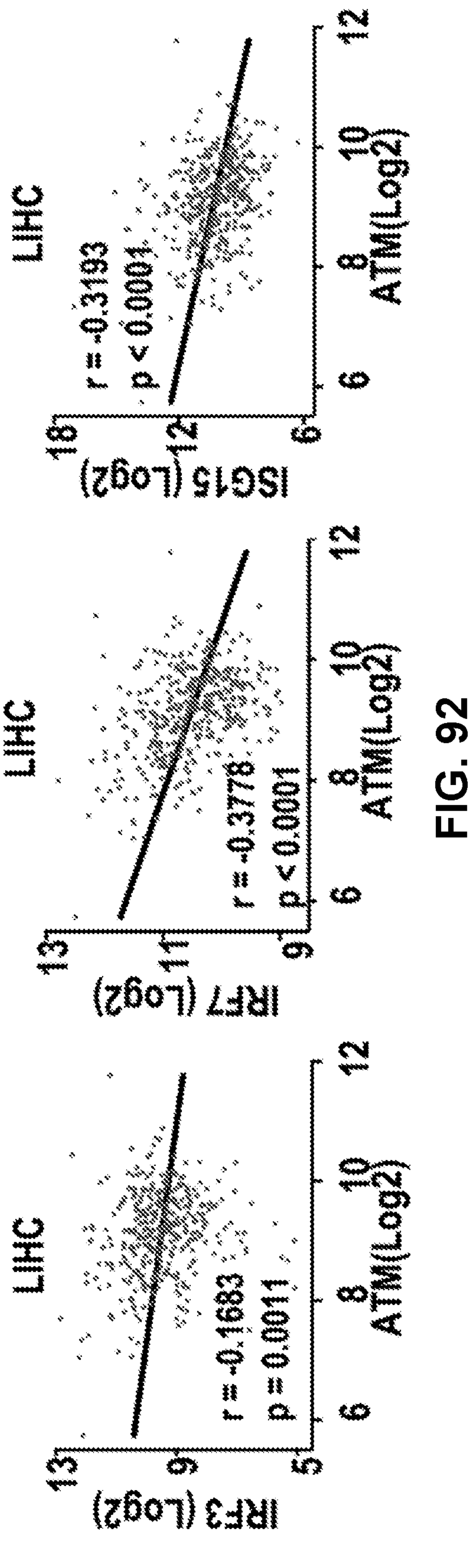
FIG. 92 presents correlation analysis for ATM expression level versus IRF3, IRF7, and ISG15 in human Liver Hepatocellular Carcinoma (LIHC, 366 samples) from TCGA Pan Cancer Atlas. R and p represent Pearson correlation coefficients and two-tailed p values.
Figure 93:
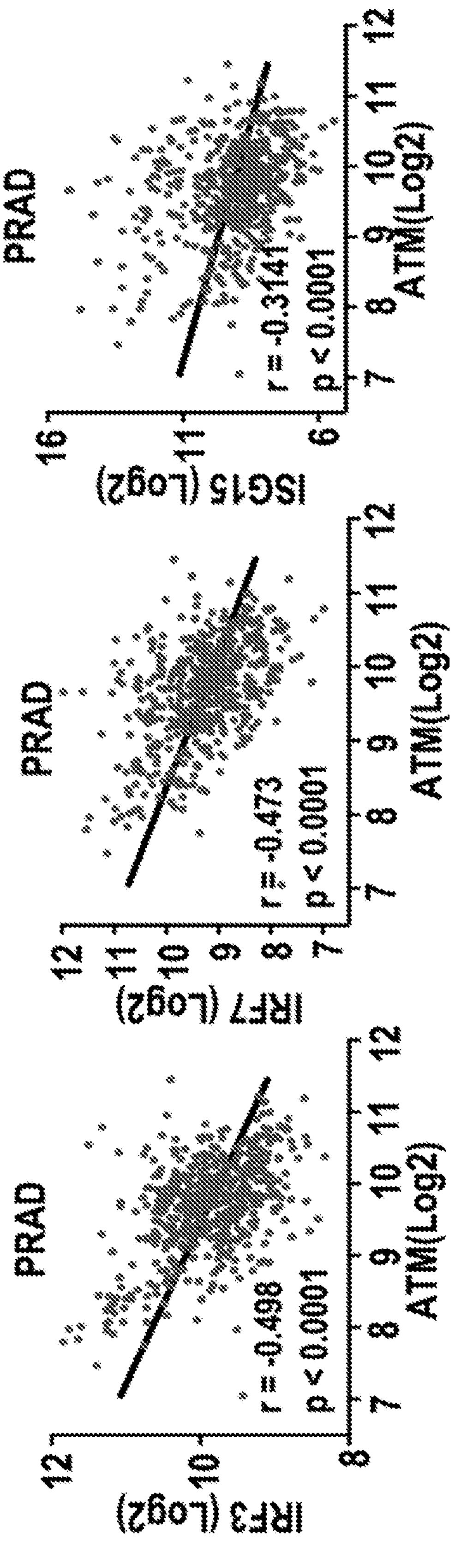
FIG. 93 presents correlation analysis for ATM expression level versus IRF3, IRF7, and ISG15 in human Prostate Adenocarcinoma (PRAD, 498 samples) from TCGA Pan Cancer Atlas. R and p represent Pearson correlation coefficients and two-tailed p values.
Figure 94:
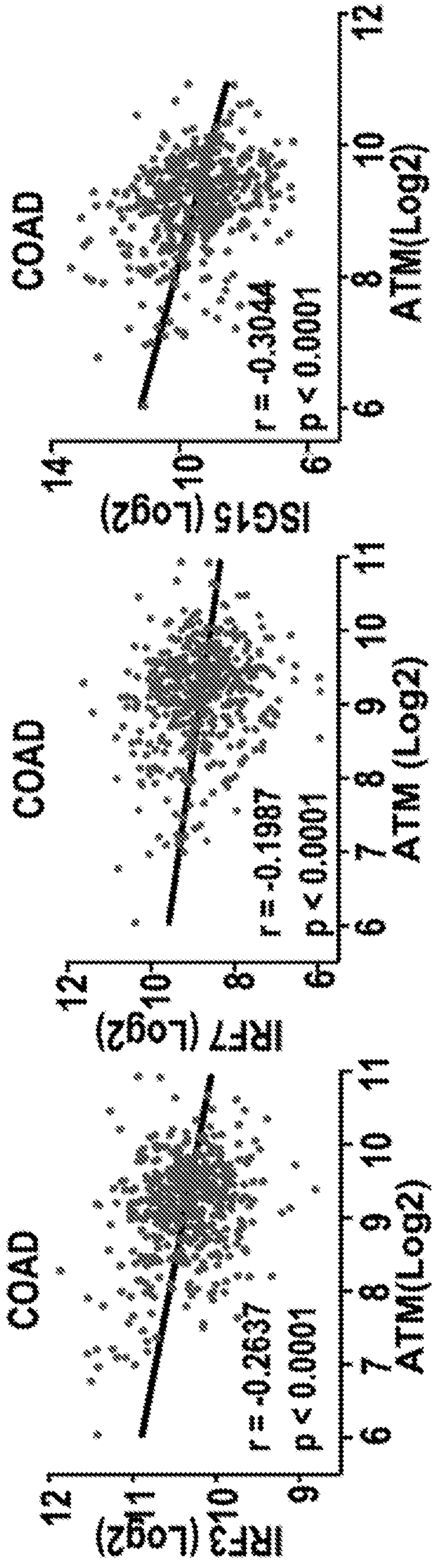
FIG. 94 presents correlation analysis for ATM expression level versus IRF3, IRF7, and ISG15 in human Colorectal Adenocarcinoma (COAD, 437 samples) from TCGA Pan Cancer Atlas. R and p represent Pearson correlation coefficients and two-tailed p values. Collectively, FIGS. 88-94 provide additional data on ATM inhibition and cGAS-STING activation.

We further examined the relationship among ATM and ISGs at the transcriptional level in human cancer patients by analyzing the transcriptome profiles in the TCGA database. Our analysis indicated ATM expression had a strong negative correlation with the expression of downstream ISG genes (ISG15, IRF3, IRF7) of the cGas-STING pathway in human Skin Cutaneous Melanoma (SKCM 472 samples) and Breast Carcinoma (BRCA, 1100 samples) (FIG. 47) which is consistent with our observation in mouse tumor cells. In addition, ATM negatively correlated with ISG15, IRF3 and IRF7 in some other cancer types (FIGS. 92, 93, 94), including cancers that are known to be resistant to anti-PD1 therapy, such as prostate cancer.

For the figures described in this section, error bars represent ±SEM. *p<0.05, p<0.01, *p<0.001, ns, not significant, as determined by two-way ANOVA.

Example 16

Figure 48:
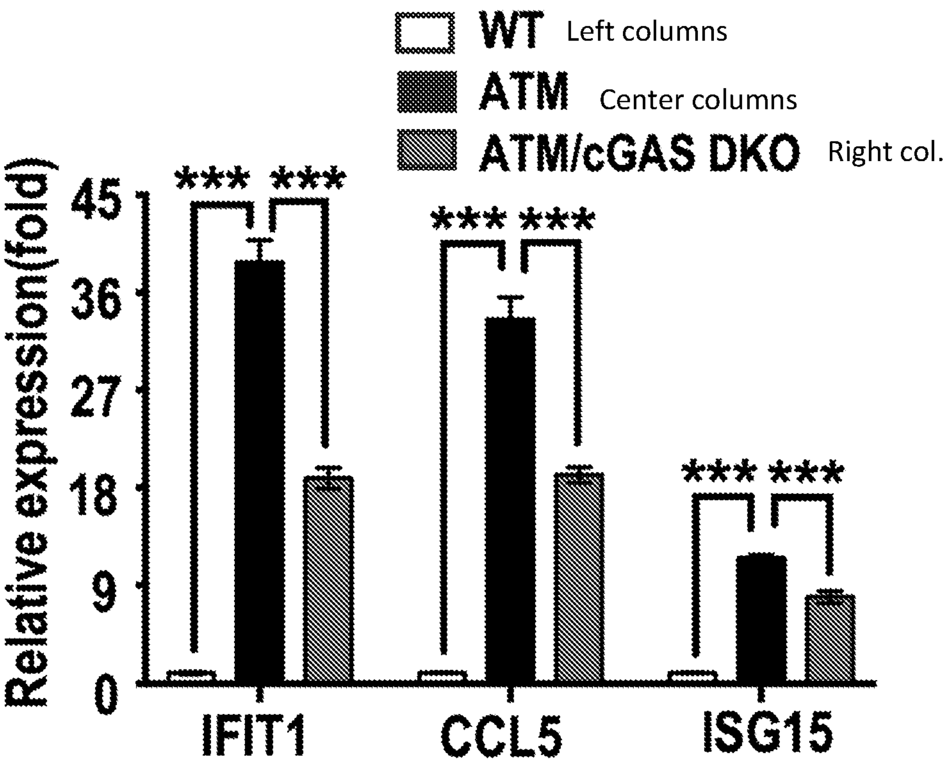
FIG. 48 presents transcriptional levels of interferon response genes IFIT1, CCL5 and ISG15 in vector control (VC), ATM KO or ATM/cGas DKO B16 cells as analyzed by real-time qPCR.
Figure 49:
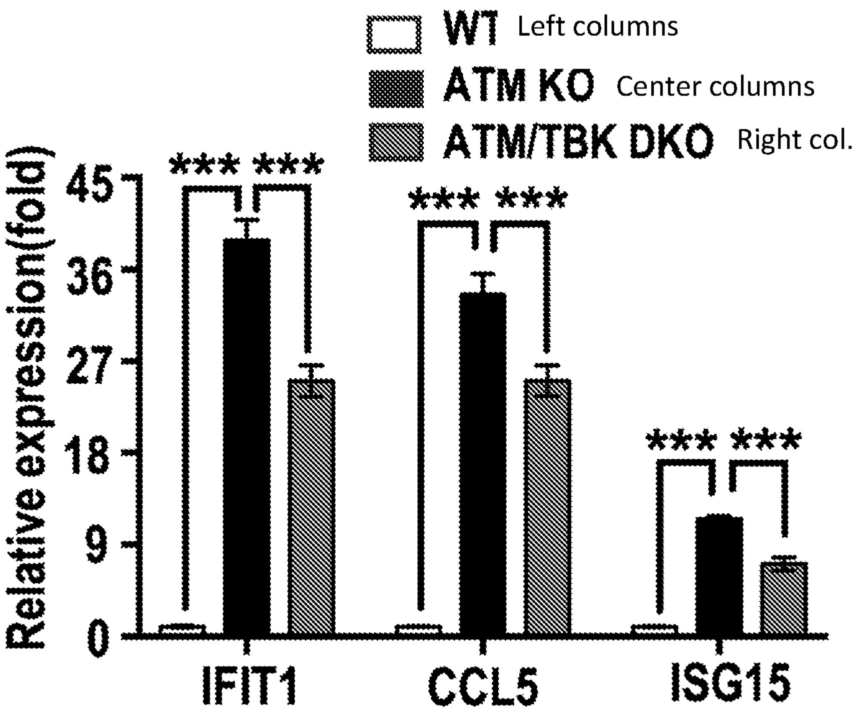
FIG. 49 presents transcriptional levels of interferon response genes in vector control (VC), ATM KO or ATM/TBK DKO B16 cells as analyzed by real-time qPCR.
Figure 50:
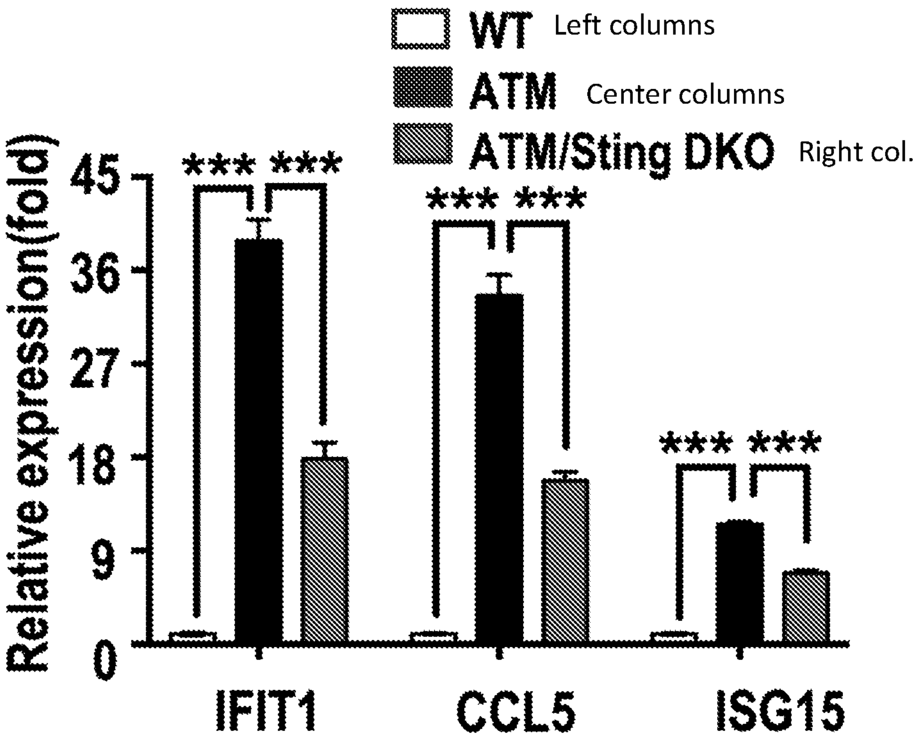
FIG. 50 presents transcriptional levels of interferon response genes in vector control (VC), ATM KO or ATM/STING DKO B16 cells as analyzed by real-time qPCR.
Figure 95:
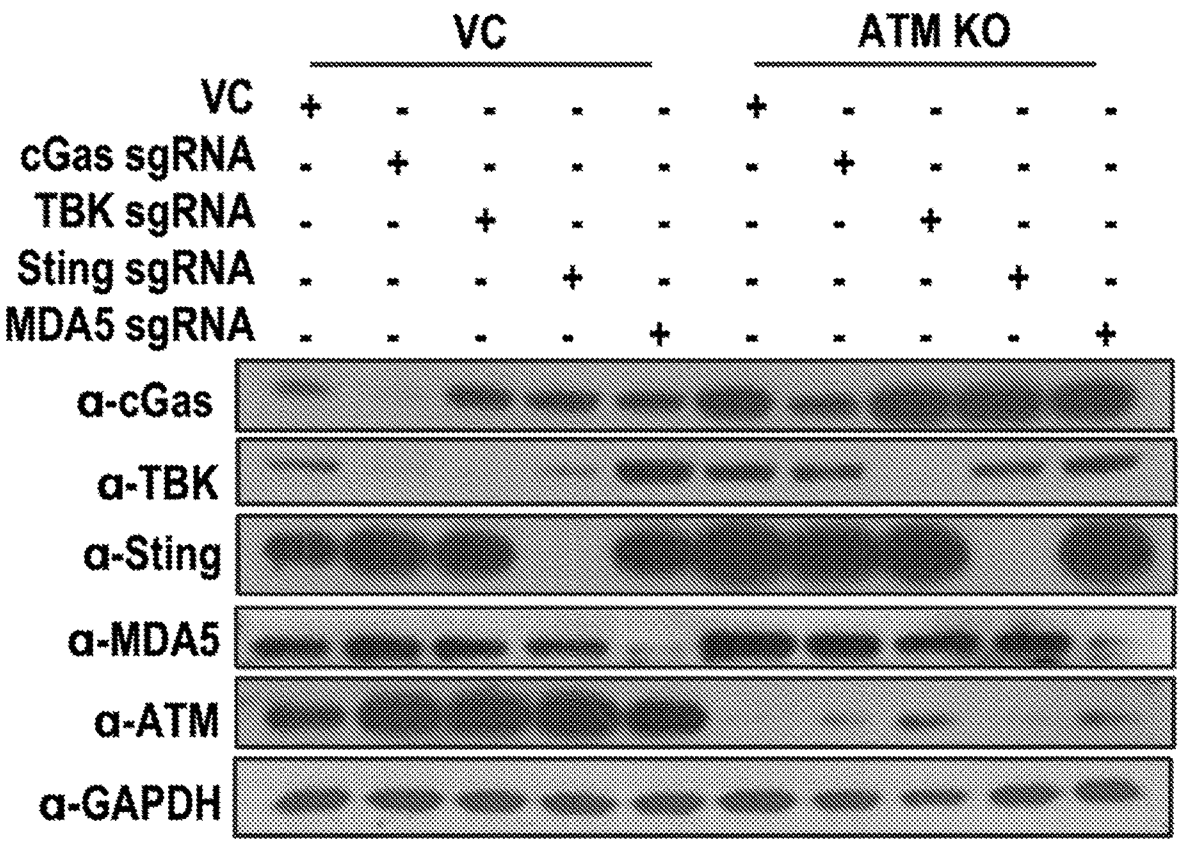
FIG. 95 presents western blot verification of gene knockout for cGas, TBK, STING, and MDA5 in vector control (VC), and ATMKO cells. GAPDH was used as the protein loading control.
Figure 96:
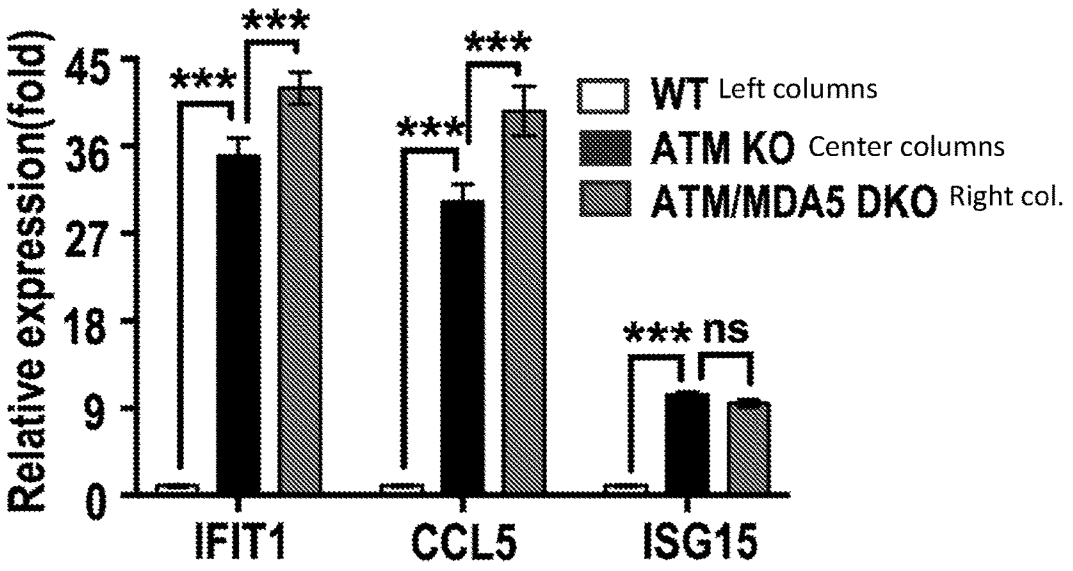
FIG. 96 presents transcriptional levels of interferon response genes in vector control (VC), ATM KO or ATM/MDA5 DKO B16 cells analyzed by real-time qPCR.

Essential roles of the cGAS-STING pathway in mediating ATM inhibition induced tumor growth delay and ICB sensitivity ISGs appear to be activated by both the DNA-sensing cGAS-STING pathway and the dsRNA-sensing MDA5/MAVS pathway (Kawai, T. et al. *Nat Immunol* (2005) doi:10.1038/ni1243). To discover which pathway was responsible for ATM deficiency induced ISGs, we generated cGAS, STING, TBK, MDA5 knockout cells in vector control and B16F10ATMKO cells (FIG. 95). We then carried out qRT-PCR analysis of mRNA levels of IFIT1, CCL5 and ISG15 in these cells. Our results indicated that the ISG transcriptional activation in ATM-deficient B16F10 cells were significantly attenuated in ATM/cGas DKO (FIG. 48), ATM/TBK DKO (FIG. 49) and ATM/STING DKO (FIG. 50) cells, but not in ATM/MDA5 DKO cells (FIG. 96). These results therefore indicate that the cGAS/STING pathway was primarily responsible for ATM deficiency induced ISG activation.

Figure 51:
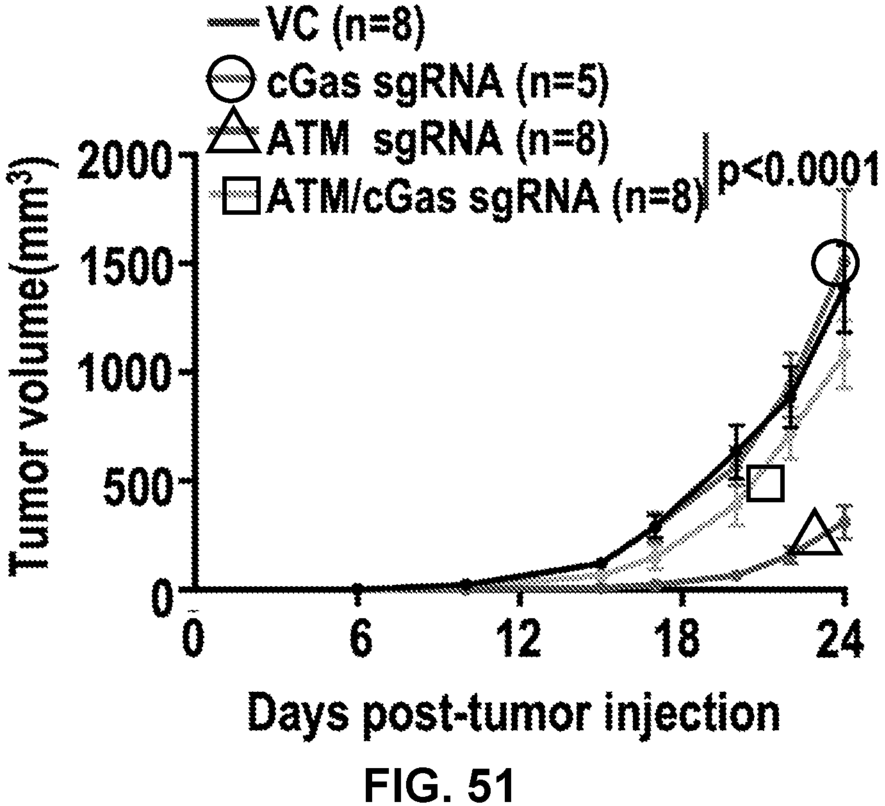
FIG. 51 presents tumor volume of C57BL/6 mice inoculated with $1\times10^5$ vector control (VC), cGas KO, ATM KO or ATM/cGas DKO B16F10 cells.
Figure 52:
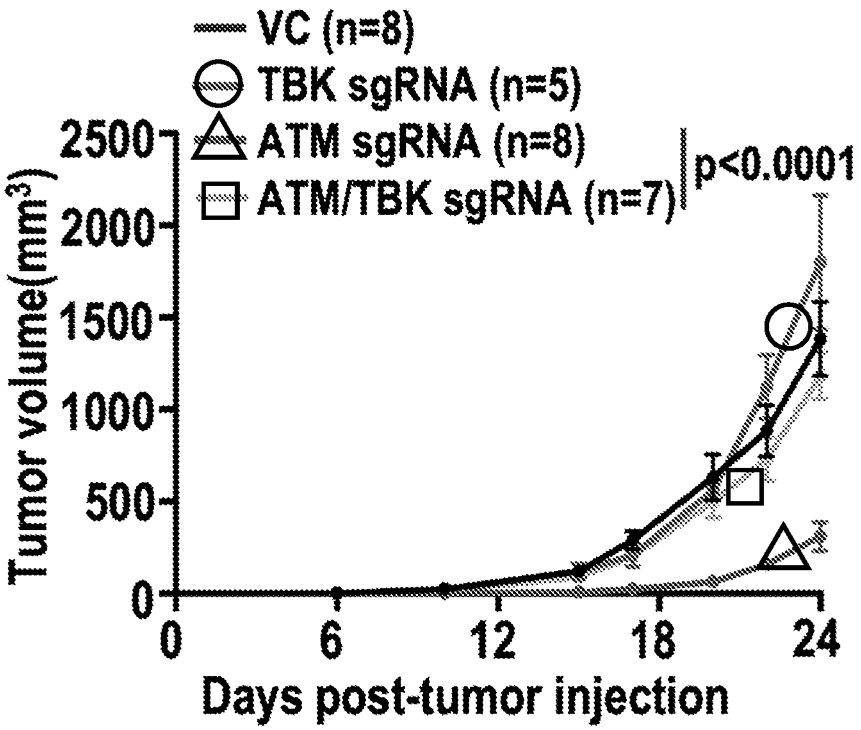
FIG. 52 presents tumor volume of C57BL/6 mice inoculated with $1\times10^5$ vector control (VC), TBK KO, ATM KO or ATM/TBK DKO B16F10 cells.
Figure 53:
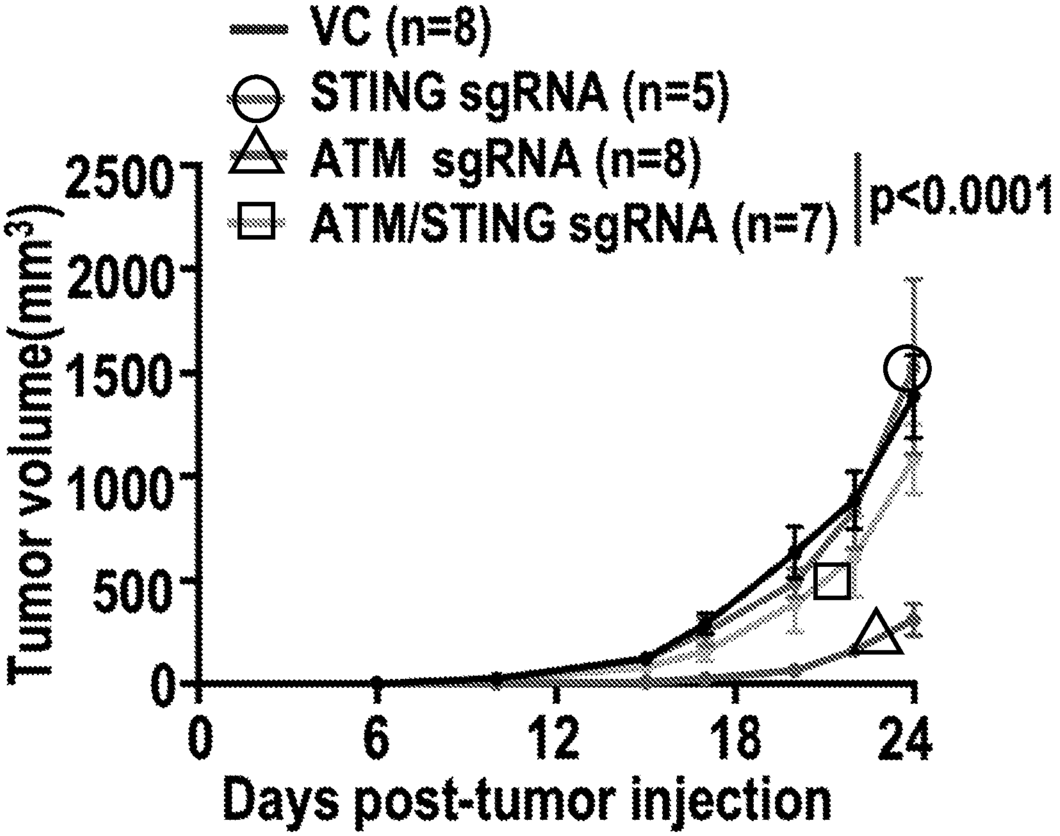
FIG. 53 presents tumor volume of C57BL/6 mice inoculated with $1\times10^5$ vector control (VC), STING KO, ATM KO or ATM/STING DKO B16 cells.
Figure 97:
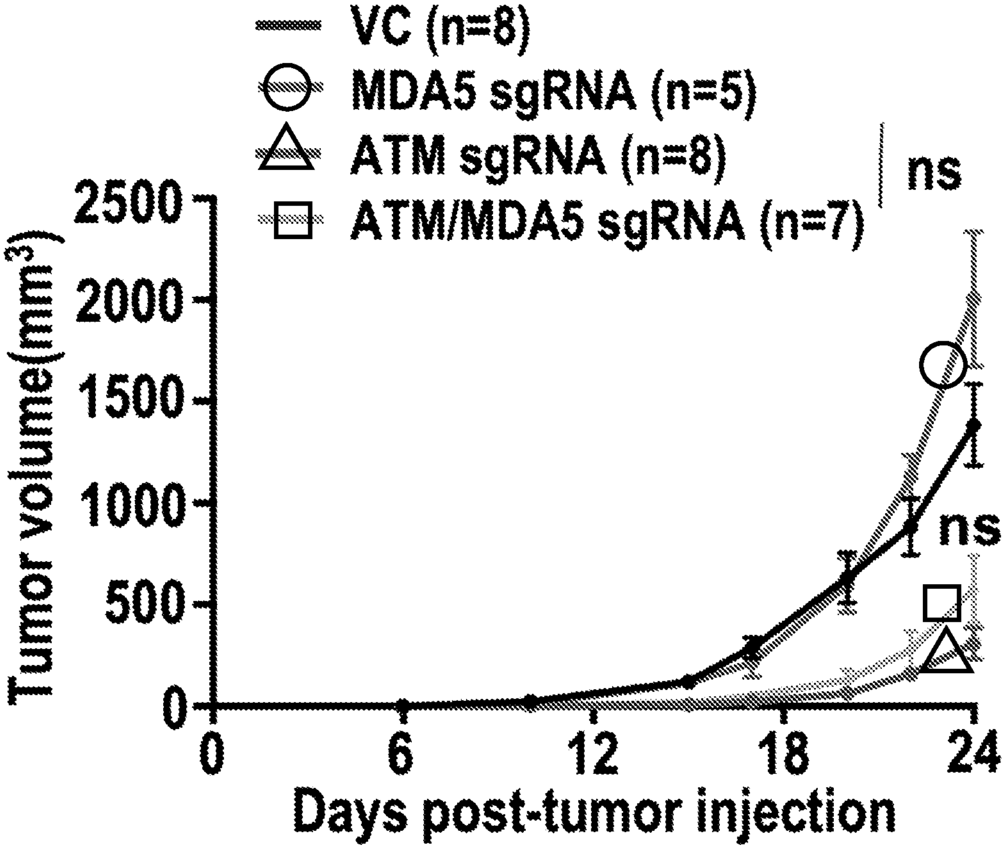
FIG. 97 presents tumor volume of C57BL/6 mice inoculated with $1\times10^5$ vector control (VC), MDA5 KO, ATM KO, or ATM/MDA5 DKO B16F10 cells. Error bars represent SEM. *$p<0.05$, $p<0.01$, *$p<0.001$; ns, not significant, as determined by 2-way ANOVA.
Figure 98:
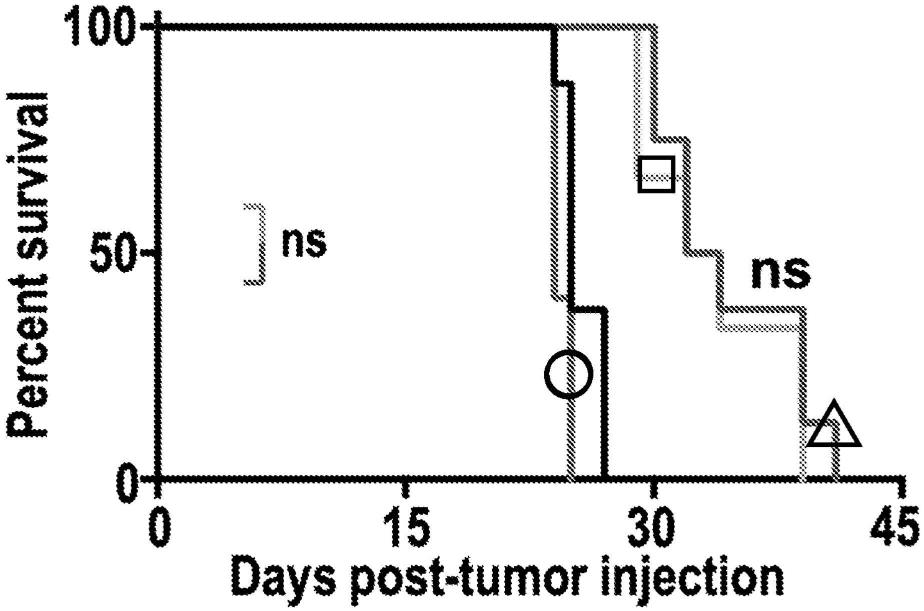
FIG. 98 presents a survival curve of C57BL/6 mice inoculated with $1\times10^5$ vector control (VC), MDA5 KO, ATM KO, or ATM/MDA5 DKO B16F10 cells. "ns", not significant, as determined by log-rank test. Collectively.

To determine whether ATM deficiency induced activation of the cGas-STING pathway was functionally responsible for the observed tumor growth suppression, we compared the tumor formation rates of ATMKO, ATM/cGAS-DKO, ATM/STING-DKO, ATM/TBK-DKO, ATM/MDA5-DKO B16F10 cells in syngeneic C57BL/6 mice. We found that deletion of cGAS (FIGS. 51, 54), TBK (FIGS. 52, 55) or STING (FIGS. 53, 56) were sufficient to abrogate ATM inhibition-elicited anti-tumor immunity. In contrast, ATM/MDA5DKO (FIGS. 97, 98) cells formed tumors at the same rate as ATMKO cells. Our results thus indicate that the cGAS/STING pathway was mainly responsible for ATM deficiency-mediated tumor suppression.

The finding that ATM deficiency leads to potent activation of the cGAS/STING pathway in the absence of DNA damaging agents such as radiotherapy has important clinical implications. Although STING agonists have shown promise in cancer therapy in preclinical models, all agents that are currently being evaluated in human patients are delivered intratumorally. A systemically delivered agent that can activate cGAS/STING has significant advantages in reaching metastatic diseases. Results from the work herein clearly demonstrated that ATM inhibitors may fit that role.

Figure 54:
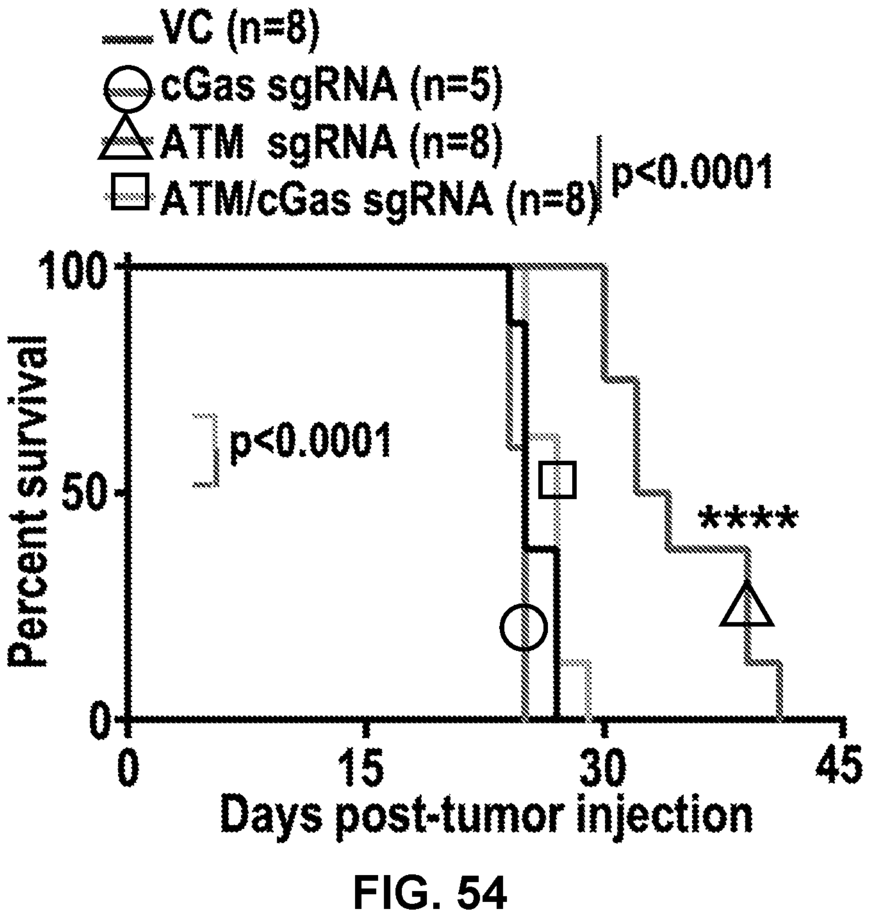
FIG. 54 presents Kaplan-Meier survival curve of C57BL/6 mice inoculated with $1\times10^5$ vector control (VC), cGas KO, ATM KO or ATM/cGas DKO B16F10 cells.
Figure 55:
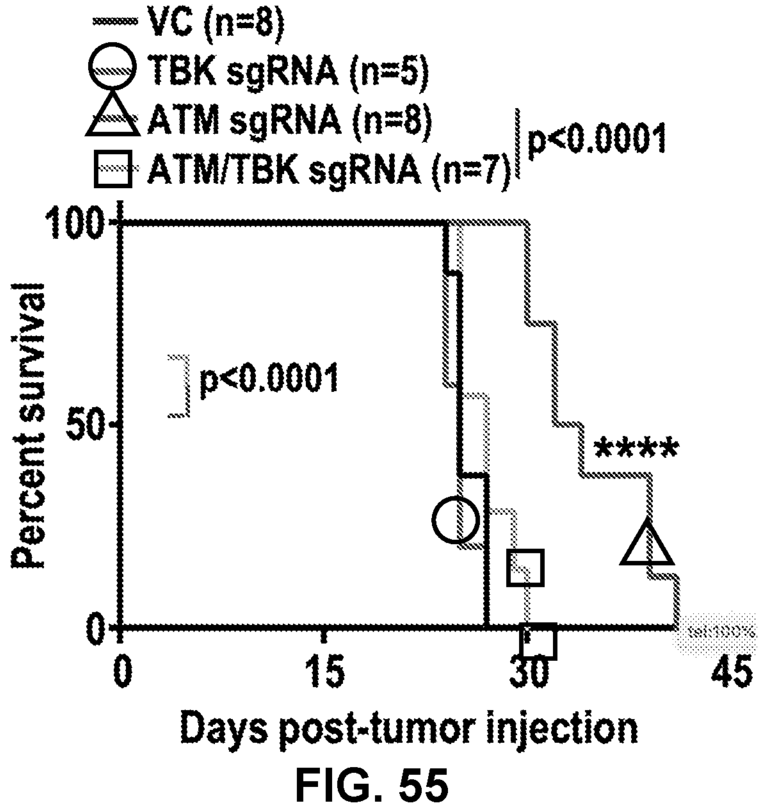
FIG. 55 presents Kaplan-Meier survival curve of C57BL/6 mice inoculated with $1\times10^5$ vector control (VC), TBK KO, ATM KO or ATM/TBK DKO B16F10 cells.
Figure 56:
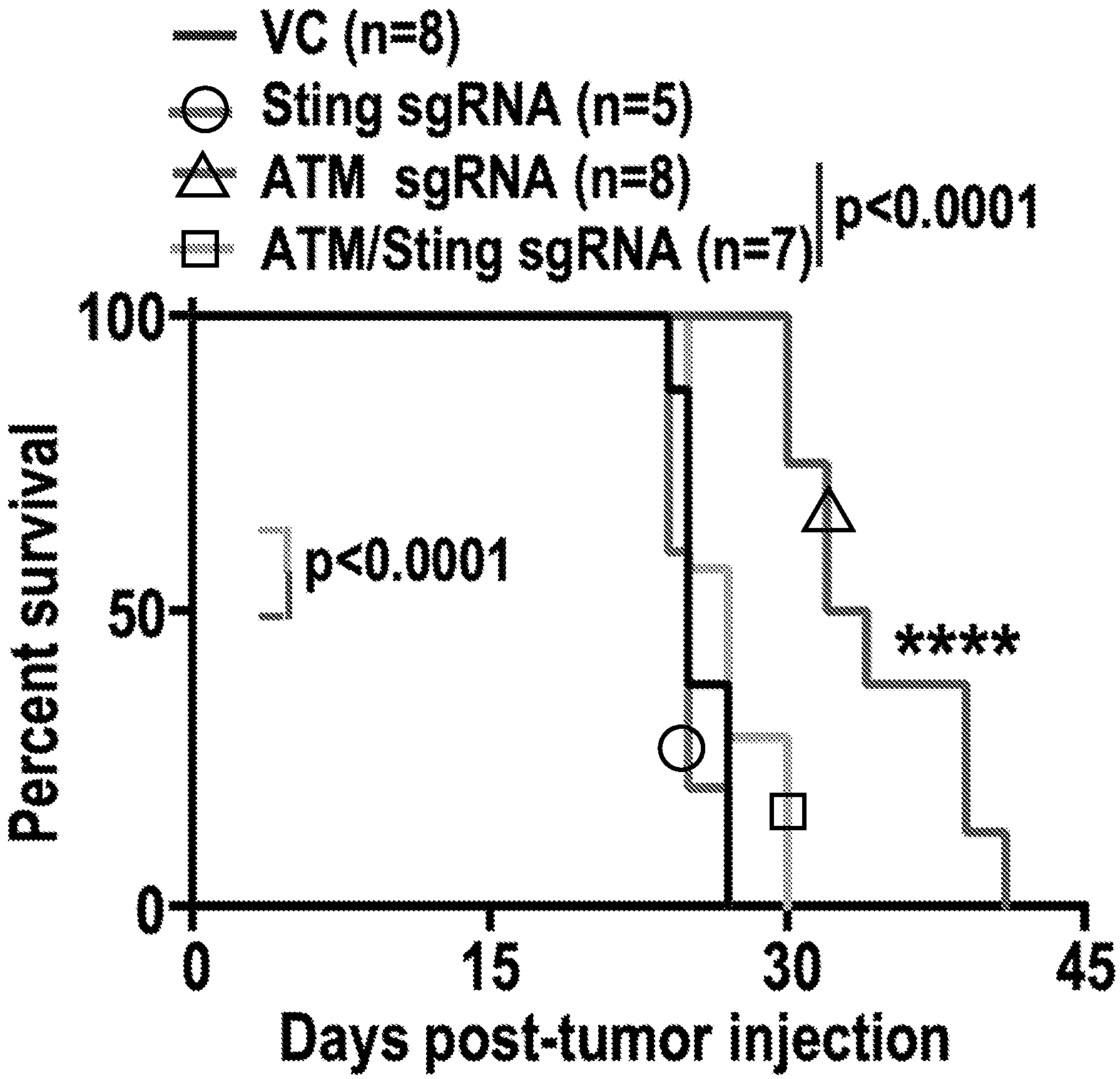
FIG. 56 presents Kaplan-Meier survival curve of C57BL/6 mice inoculated with $1\times10^5$ vector control (VC), STING KO, ATM KO or ATM/STING DKO B16 cells. Collectively, FIGS. 48-56 indicate that ATM inhibition mediates ISG activation and tumor growth delay through cGas-STING activation.

For the figures described in this section, error bars represent standard error of the mean (SEM). *p<0.05, p<0.01, *p<0.001, **p<0.0001; ns, not significant, as determined by 2-way ANOVA (FIGS. 48-53) or log-rank test (FIGS. 54-56**).

Example 17

Figure 57:
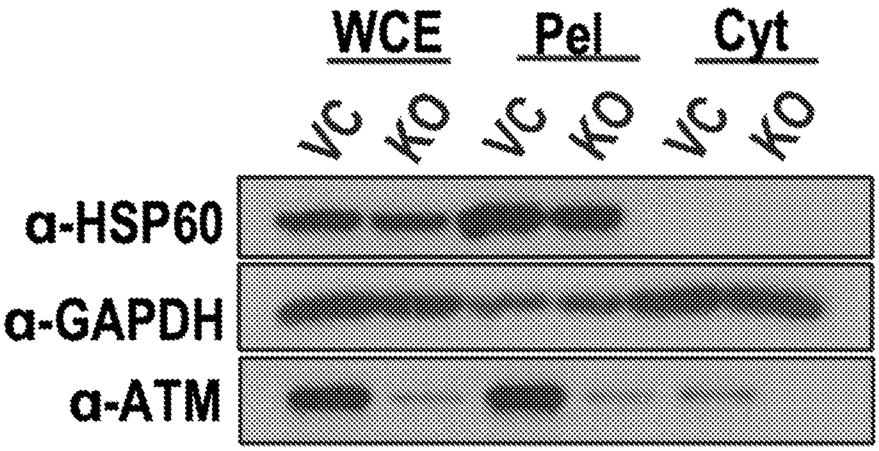
FIG. 57 presents western blot verification of our cytosol fractionation protocol. Vector control and ATM KO B16 cells were subjected to digitonin fractionation as described herein and whole-cell extracts (WCE), pellets (Pel) and cytosolic extracts (Cyt) were blotted using indicated antibodies.
Figure 58:
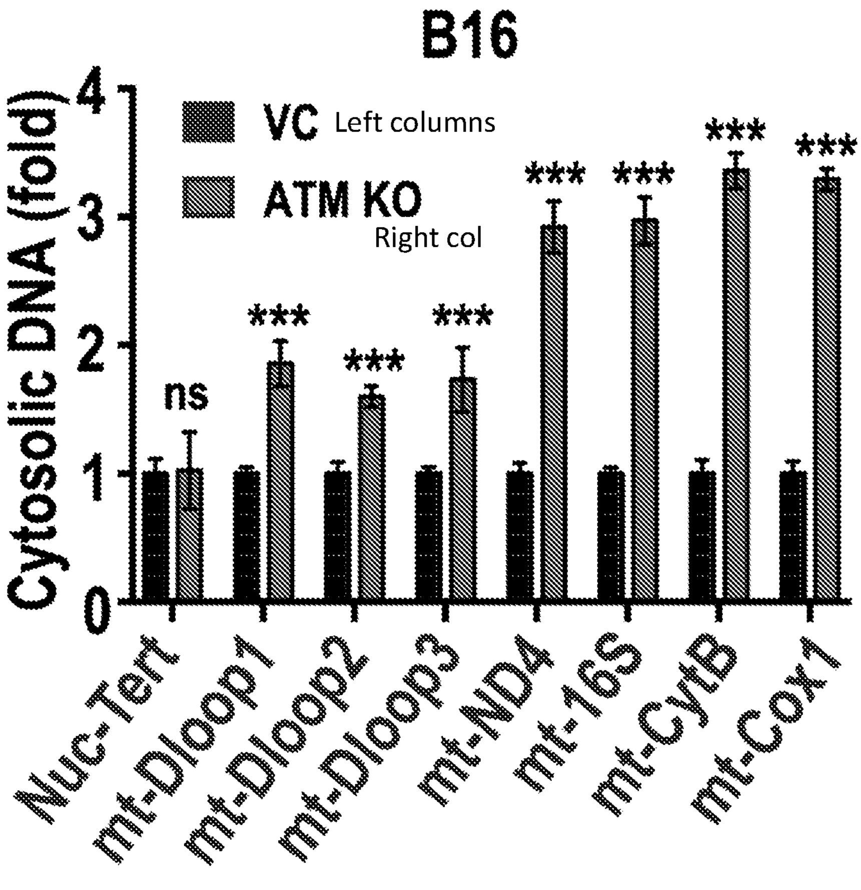
FIG. 58 presents Q-RT PCR quantification of cytosolic DNA extracted from digitonin-permeabilized cyotosolic extracts of control and ATM KO B16F10 cells. Normalization was carried out as described herein. Error bars represent ±SEM. *$p<0.05$, $p<0.01$, *$p<0.001$, ns, not significant, as determined by two-way ANOVA.
Figure 59:
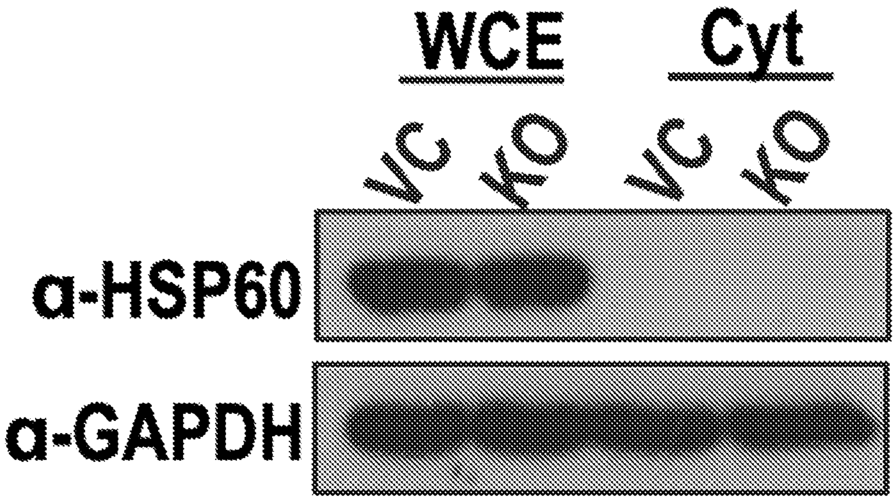
FIG. 59 presents western blot analysis of B16F10 cells treated with 1 μM AZD1390 for 48 hours and subjected to digitonin fractionation as described herein.
Figure 60:
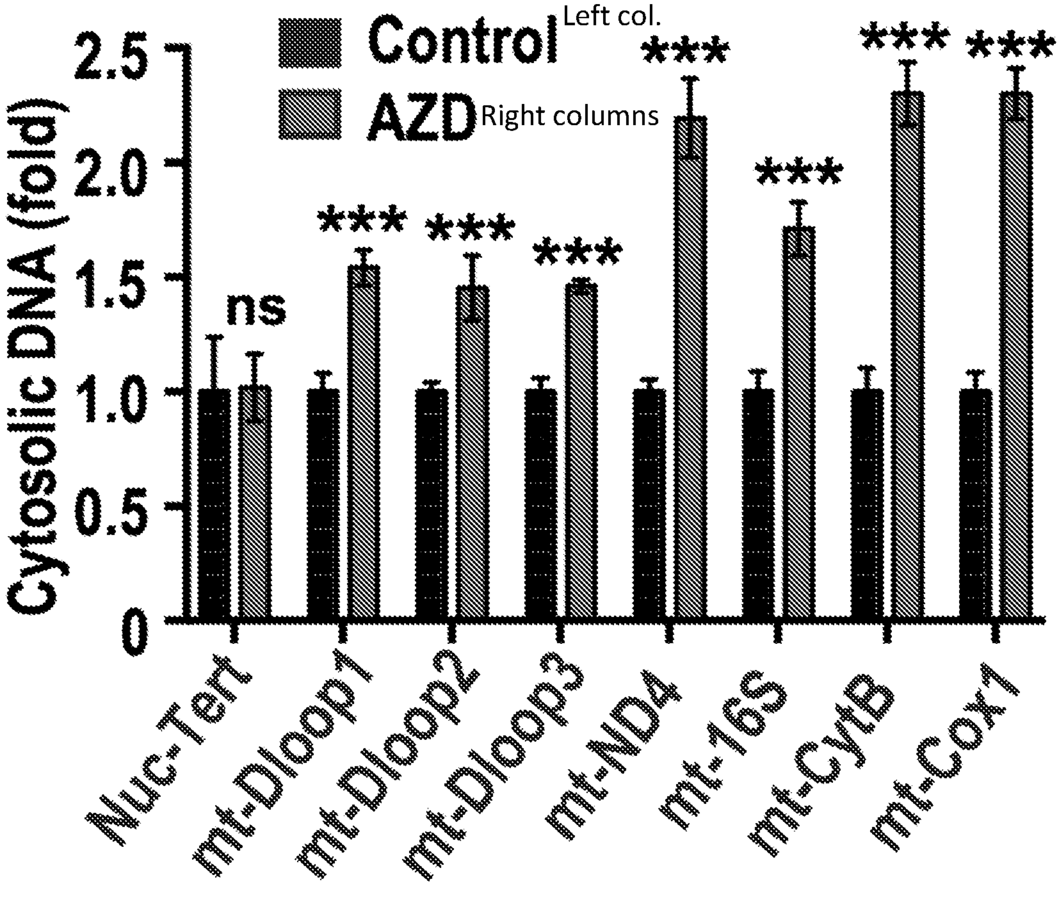
FIG. 60 presents Q PCR analysis of DNA extracted from digitonin-permeabilized extracts of control and AZD1390 treated B16 cells.
Figure 61:
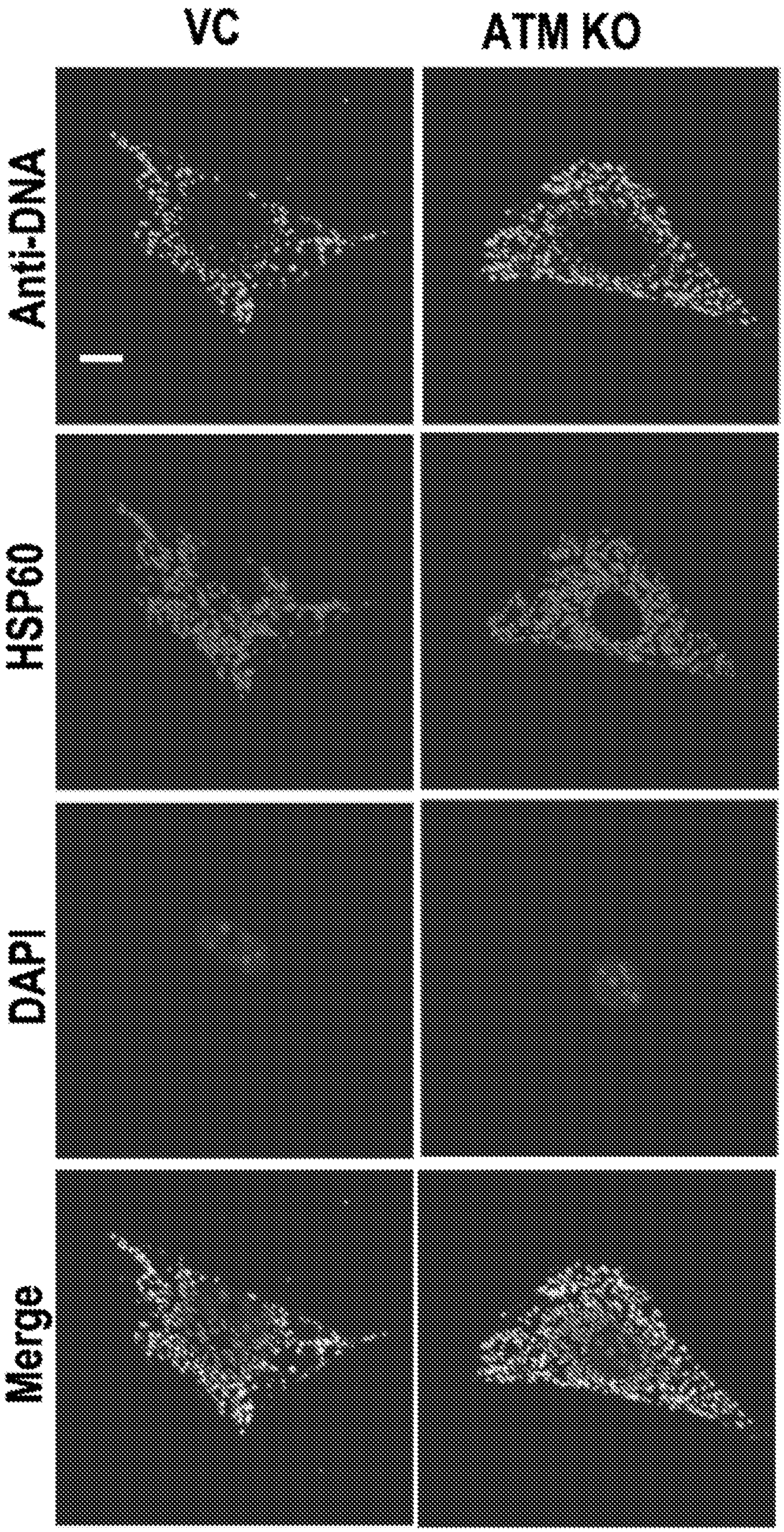
FIG. 61 presents control (VC) and ATM KO B16F10 cells that were co-stained with anti-DNA (adjacent "Anti-DNA" panels), anti-HSP60 (adjacent "HSP60" panels) and DAPI (adjacent "DAPI" panels). Scale bar indicated 10 μm. The bottom panels represent a merge of the top three groups.
Figure 99:
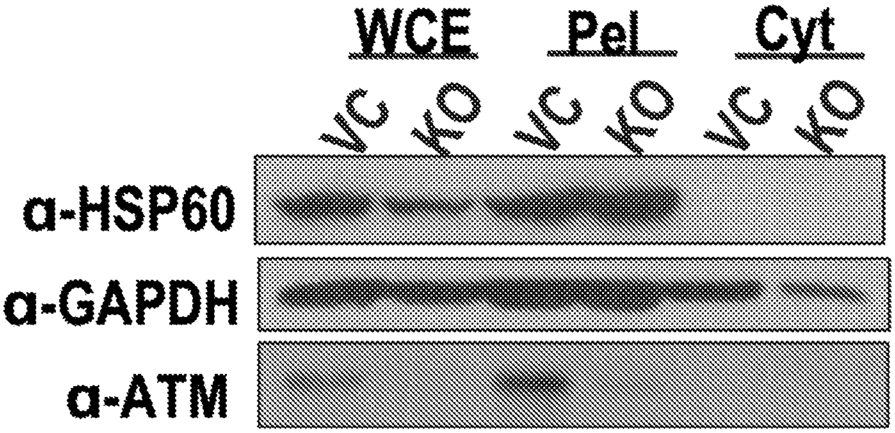
FIG. 99 presents vector control and ATM KO 4T1 cells were subjected to digitonin fractionation as described in the Methods and whole-cell extracts (WCE), pellets (Pel) and cytosolic extracts (Cyt) were blotted using indicated antibodies.
Figure 100:
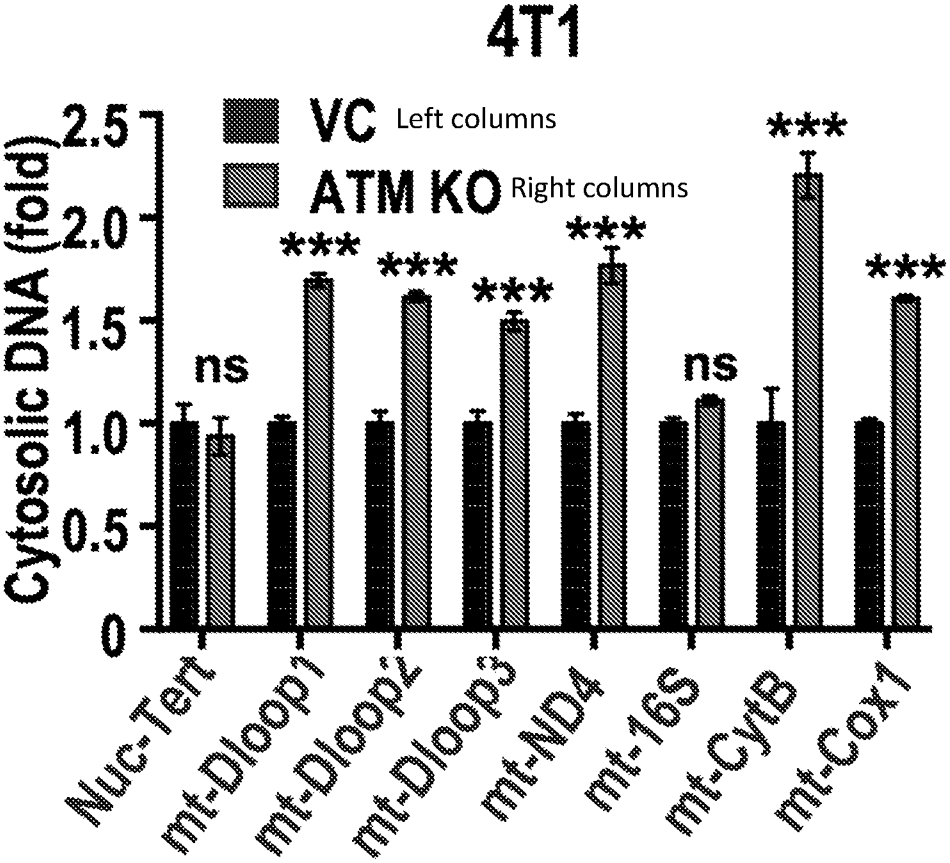
FIG. 100 presents data from an experiment in which DNA was extracted from digitonin extracts of vector control and ATM 4T1 cells. Cytosolic mtDNA was quantitated via qPCR using mitochondrial DNA primer sets and the nuclear gene TERT primer. Normalization was carried out as described herein. Error bars represent SEM. *$p<0.05$, $p<0.01$, *$p<0.001$, ns, not significant, as determined by 2-way ANOVA.
Figure 101:
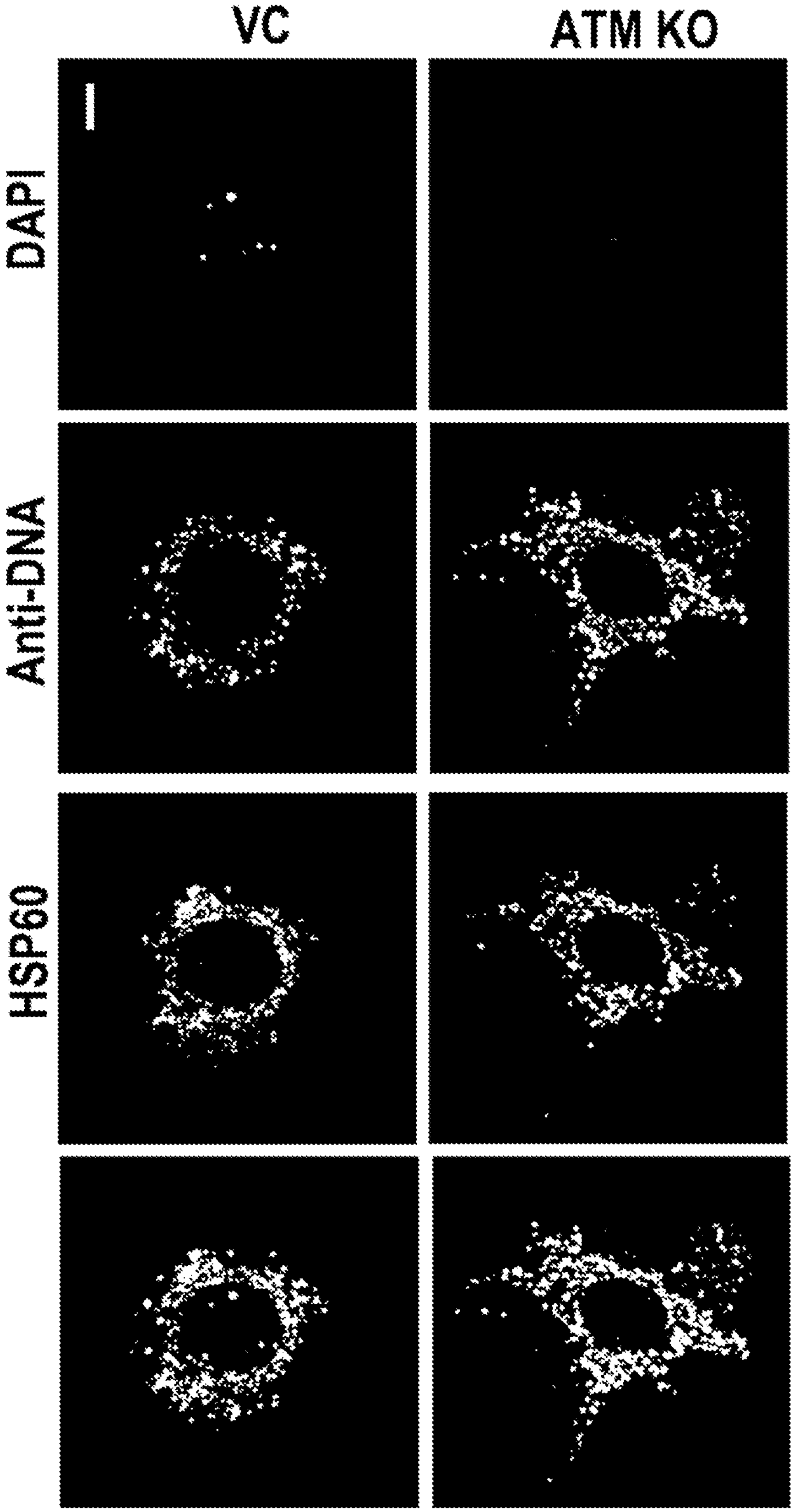
FIG. 101 presents immunofluorescence detection of dsDNA location in vector control (VC) and ATM KO 4T1 cells by use of anti-DNA ("Anti-DNA" panels), anti-HSP60 ("HSP60" panels, for mitochondria), and DAPI ("DAPI panels, for nuclear DNA). Scale bar represents 10 μm. The bottom panels represent a merge of the top three groups.

TFAM Downregulation and Mitochondrial DNA Release as the Mechanism for ATM Deficiency Induced Activation of the cGAS-STING Pathway We next sought to elucidate the unknown mechanism(s) involved in ATM deficiency-induced cGAS/STING activation. The cGas-STING pathway functions to detect the presence of cytosolic DNA and, in response, trigger expression of inflammatory genes. We hypothesized that ATM deficiency causes an increase in cytosolic DNA which triggers the activation of the cGAS/STING pathway. Cytosolic DNA can originate from two sources: the nucleus and the mitochondria. To determine the source of cytosolic DNA in ATM-deficient cell, we fractionated vector control and ATM-deficient B16F10 cells and purified DNA from cytosolic extracts. The efficiency of our fractionation was determined by western blot where HSP60 and GAPDH were used as markers for mitochondria and cytosolic fractions, respectively (FIG. 57). Q-PCR analysis of the cytosolic fraction indicated that cytosolic DNA in ATM-deficient B16F10 and 4T1 cells were mainly mitochondrial DNA (as represented by Dloop1, 2, 3, ND4, 16S, CytB, Cox1), instead of nuclear DNA (represented by TERT) (FIG. 58). Similar results were also observed in ATM-deficient 4T1 cells (FIGS. 99, 100). We further showed that the ATM inhibition by AZD1390 also induced mitochondrial DNA (mtDNA) release in B16F10 cells (FIGS. 59, 60). Further proof of ATM-deficiency induced mtDNA leakage came from antibody-based immunofluorescence staining of dsDNA. Our results indicated that ATM-deficient B16F10 cells had a significantly increased amount of cytosolic dsDNA outside the mitochondria (FIG. 61). Similar results were also observed in ATM-deficient 4T1 cells (FIG. 101). Thus, our results provided strong evidence for ATM deficiency-induced mtDNA release.

Figure 85:
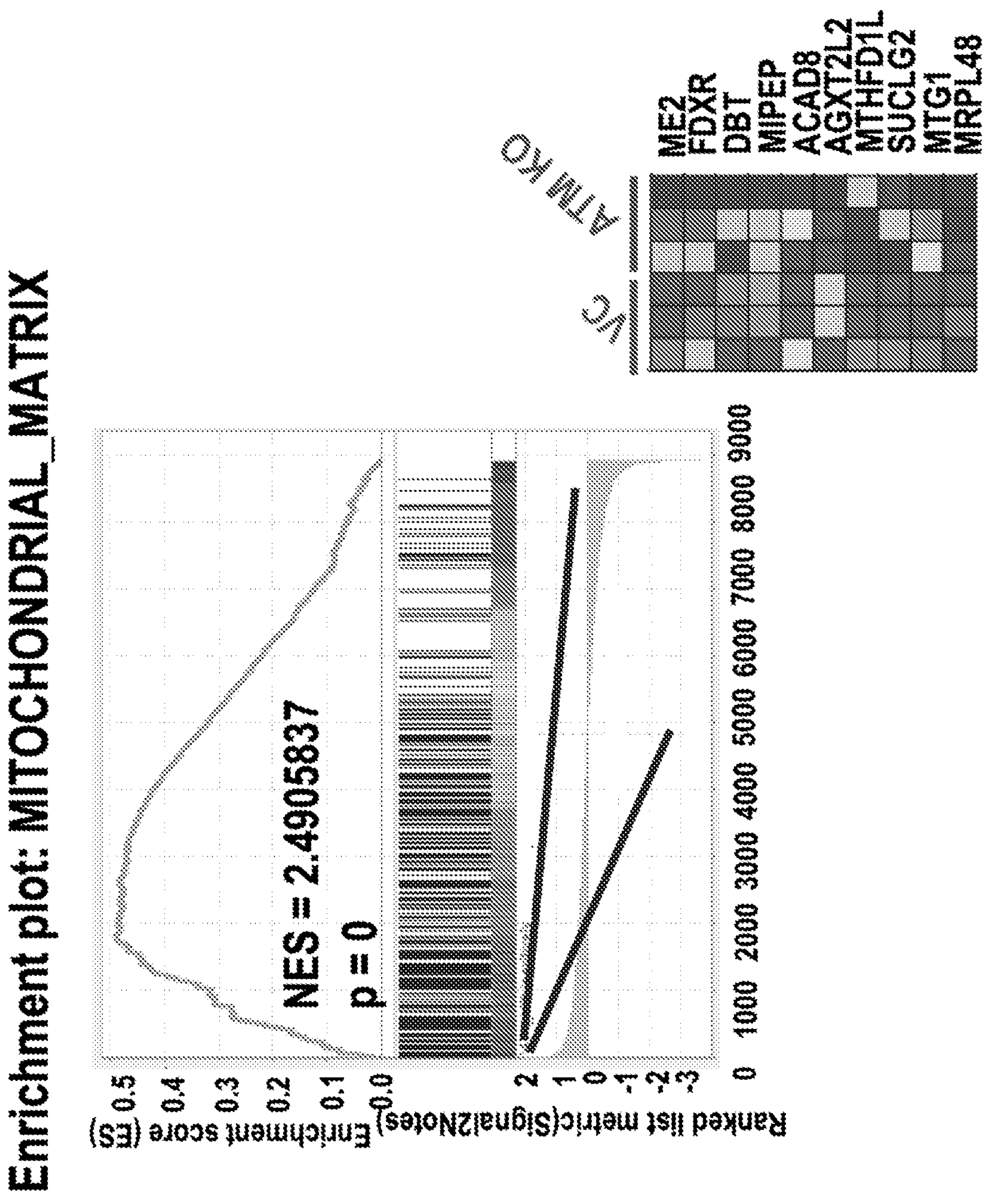
FIG. 85 presents gene set enrichment analysis (GSEA) of mitochondrial pathways in 4T1 ATM KO cells vs vector control (VC) tumors. FDR calculated using GSEA.
Figure 86:
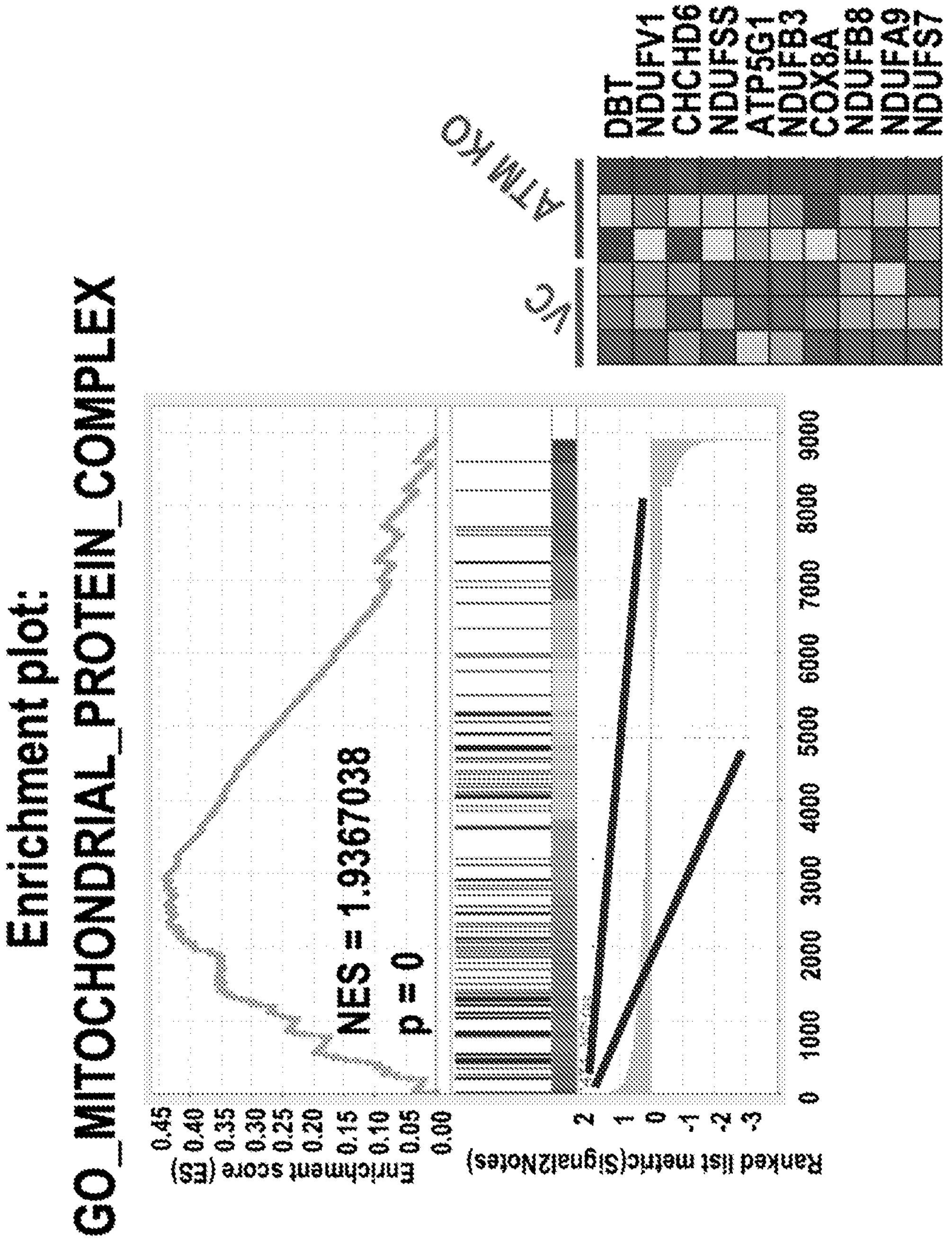
FIG. 86 presents gene set enrichment analysis (GSEA) of mitochondrial pathways in 4T1 ATM KO cells vs vector control (VC) tumors. FDR calculated using GSEA.
Figure 87:
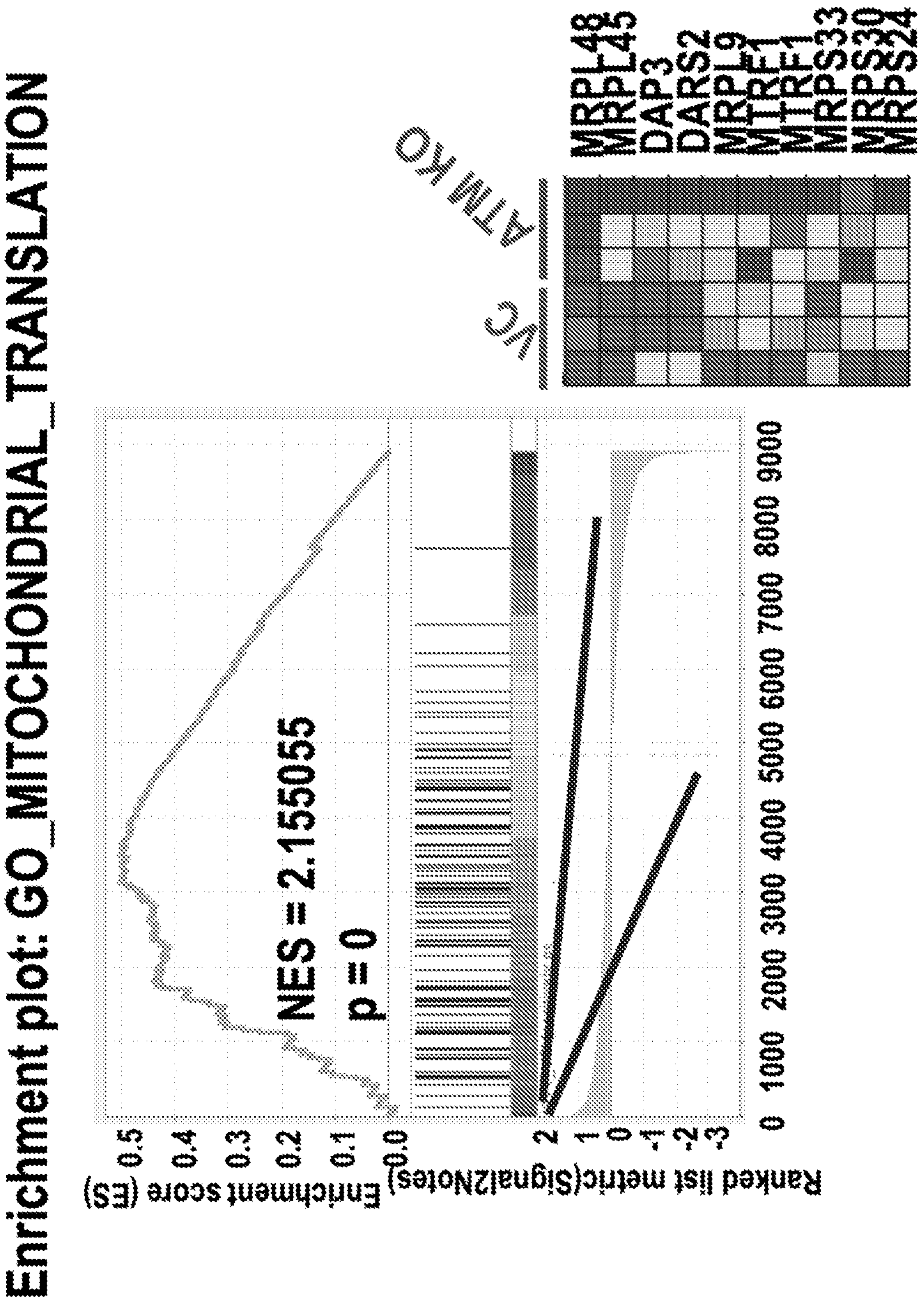
FIG. 87 presents gene set enrichment analysis (GSEA) of mitochondrial pathways in 4T1 ATM KO cells vs vector control (VC) tumors. FDR calculated using GSEA. Collectively.

Our identification of the mitochondria as the main source of cytosolic DNA was consistent with gene ontology (GO) analysis of RNAseq data of ATMKO 4T1 cells, which showed attenuation of mitochondria-related GO pathways in ATMKO vs vector control 4T1 cells (FIGS. 85, 86, 87).

Figure 62:
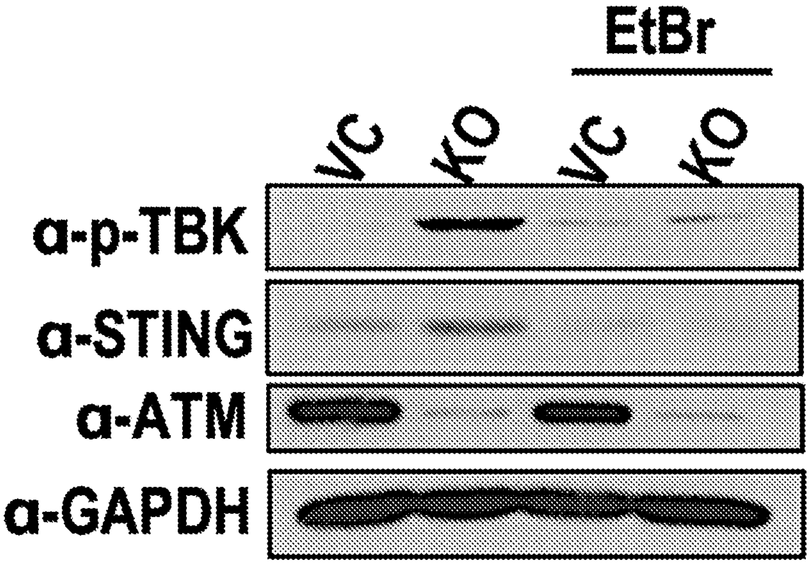
FIG. 62 presents western blot analysis of protein levels of pTBK and STING in control (VC) and ATM KO B16F10 Cells exposed to 100 ng/ml EtBr for 20 days.
Figure 102:
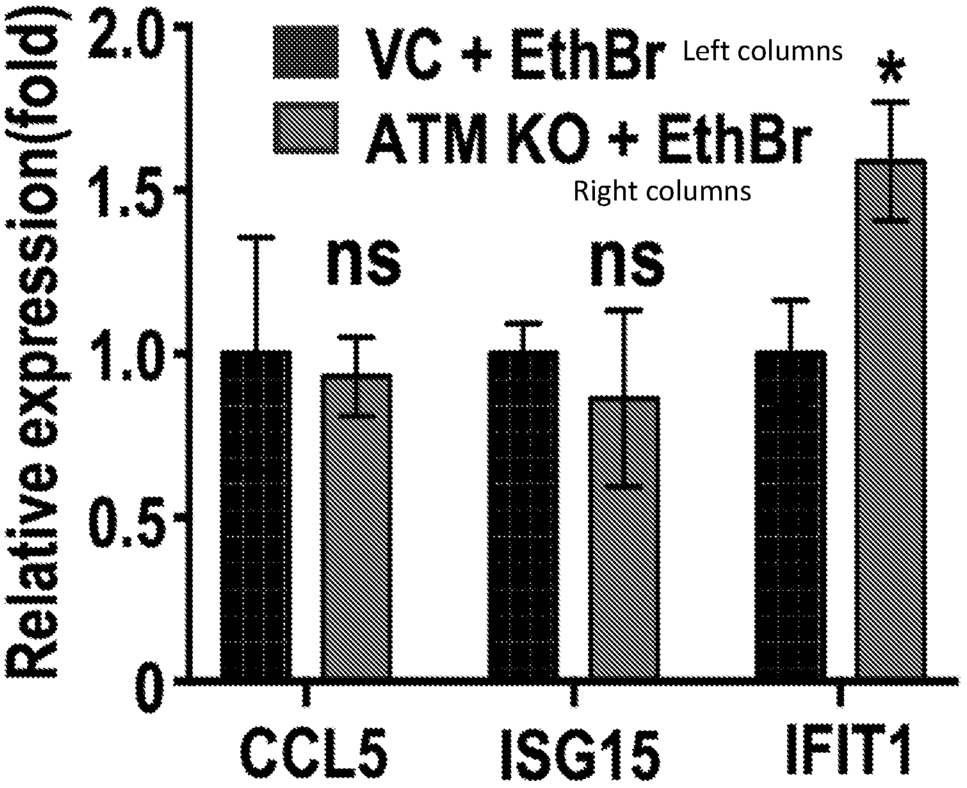
FIG. 102 presents Q-PCR analysis of interferon response gene expression in vector control and ATMKO B16F10 cells that had been treated with 100 ng/ml ethidium bromide for 20 days. Error bars represent SEM. *$p<0.05$, $p<0.01$, *$p<0.001$, ns, not significant, as determined by 2-way ANOVA.
Figure 103:
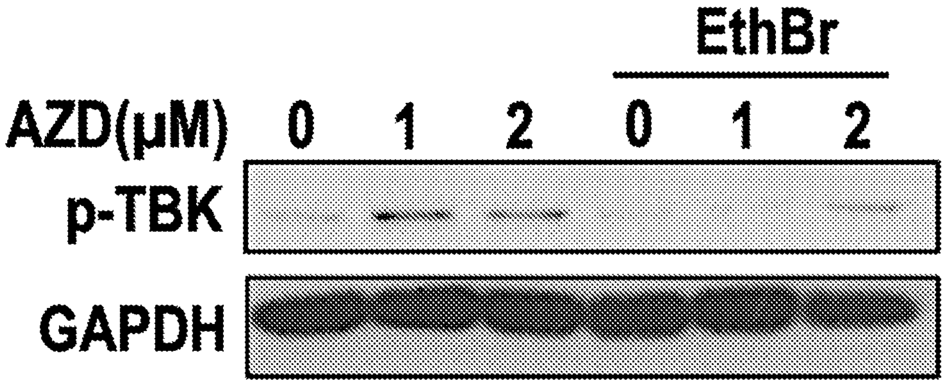
FIG. 103 presents western blot analysis of pTBK levels in B16F10 cells that had been treated with 100 ng/ml ethidium bromide for 20 days and then exposed to 1 μM of AZD1390 for 48 hr. GAPDH was used as protein loading control.
Figure 104:
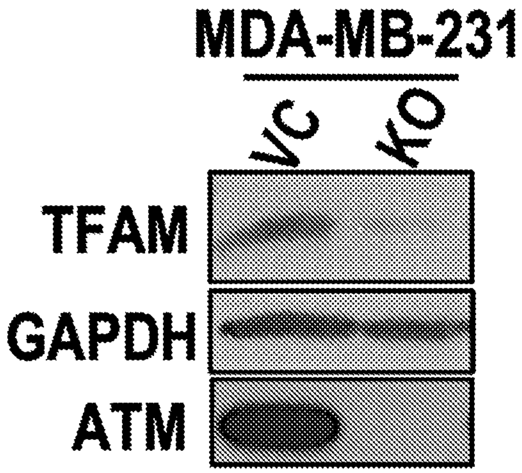
FIG. 104 presents western blot analysis of TFAM expression in human control and ATMKO MDA-MB-231 cells.
Figure 105:
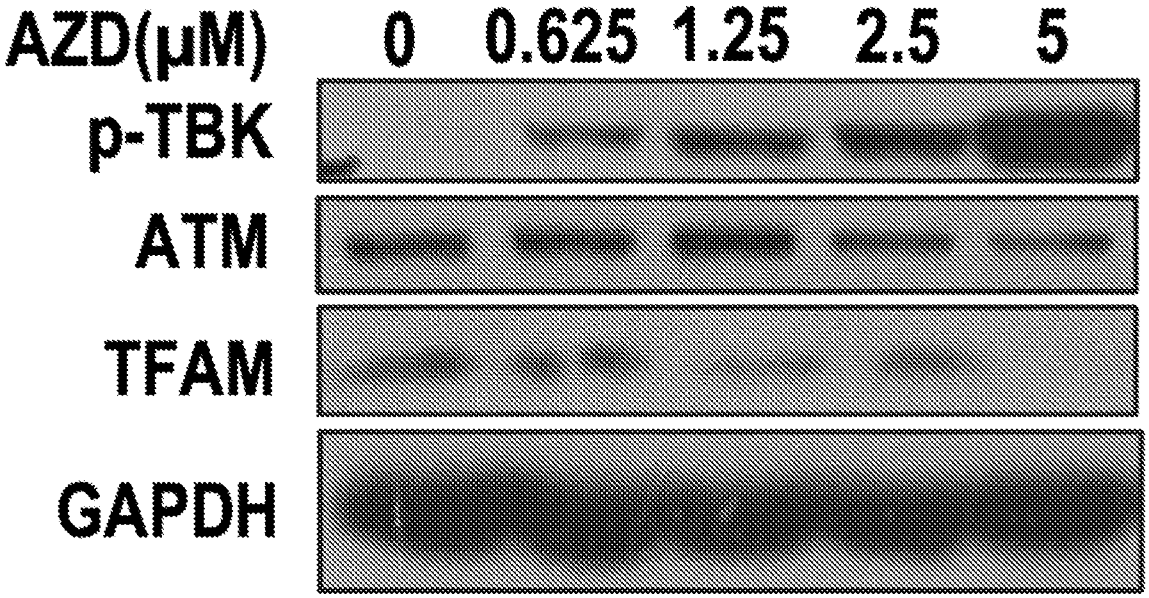
FIG. 105 presents western blot analysis of TFAM levels in B16F10 cells treated with AZD1390 for 48 hrs.
Figure 106:
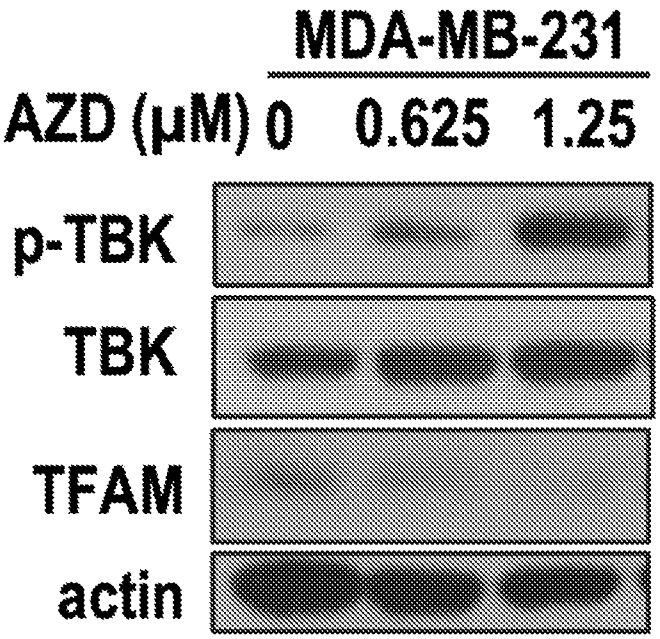
FIG. 106 presents western blot analysis of TFAM levels in MDA-MB-231 cells treated with AZD1390 for 48 hrs.

We next investigated whether mtDNA release into the cytosol was indeed responsible for activation of the cGAS-STING pathway in ATMKO cells. We used an established protocol for depleting cellular mtDNA by use of ethidium bromide (EtBr; White, M. J. et al. *Cell* (2014) doi:10.1016/j.cell.2014.11.036). Depletion of cellular mtDNA significantly diminished ATM deficiency-induced expression of STING and p-TBK protein levels (FIG. 62) and ISGs (FIG. 102). In addition, EtBr-induced depletion of mtDNA in wide-type B16F10 also abrogated cGAS-STING activation induced by the ATM inhibitor AZD1390 (FIG. 103). Thus, our data demonstrate the elimination of mtDNA through EtBr incubation abrogated ATM inhibition-mediated cGAS/STING activation and underscore the importance of ATM in restraining cellular innate immunity through mitochondria homeostasis.

Figure 63:
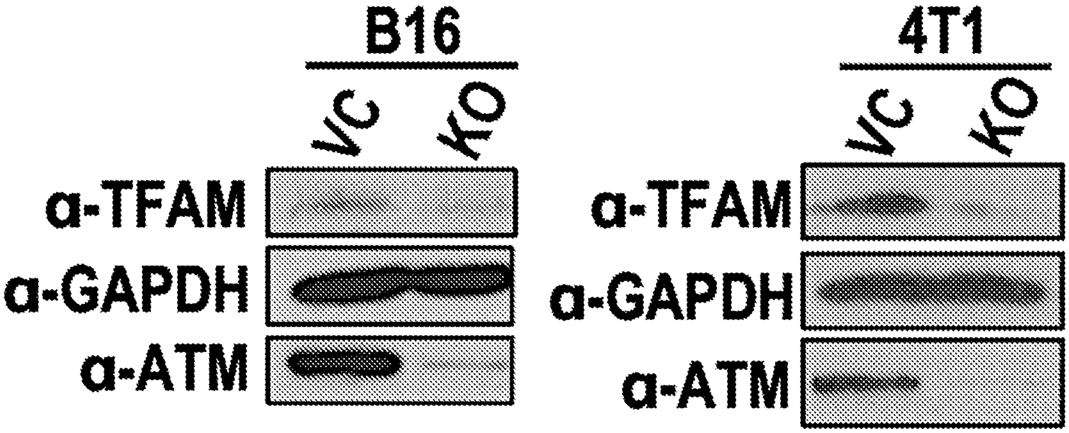
FIG. 63 presents western blot analysis of expression levels of TFAM in murine vector control and ATM KO B16F10 ("g" panel) and 4T1 ("h" panel) cells.
Figure 64:
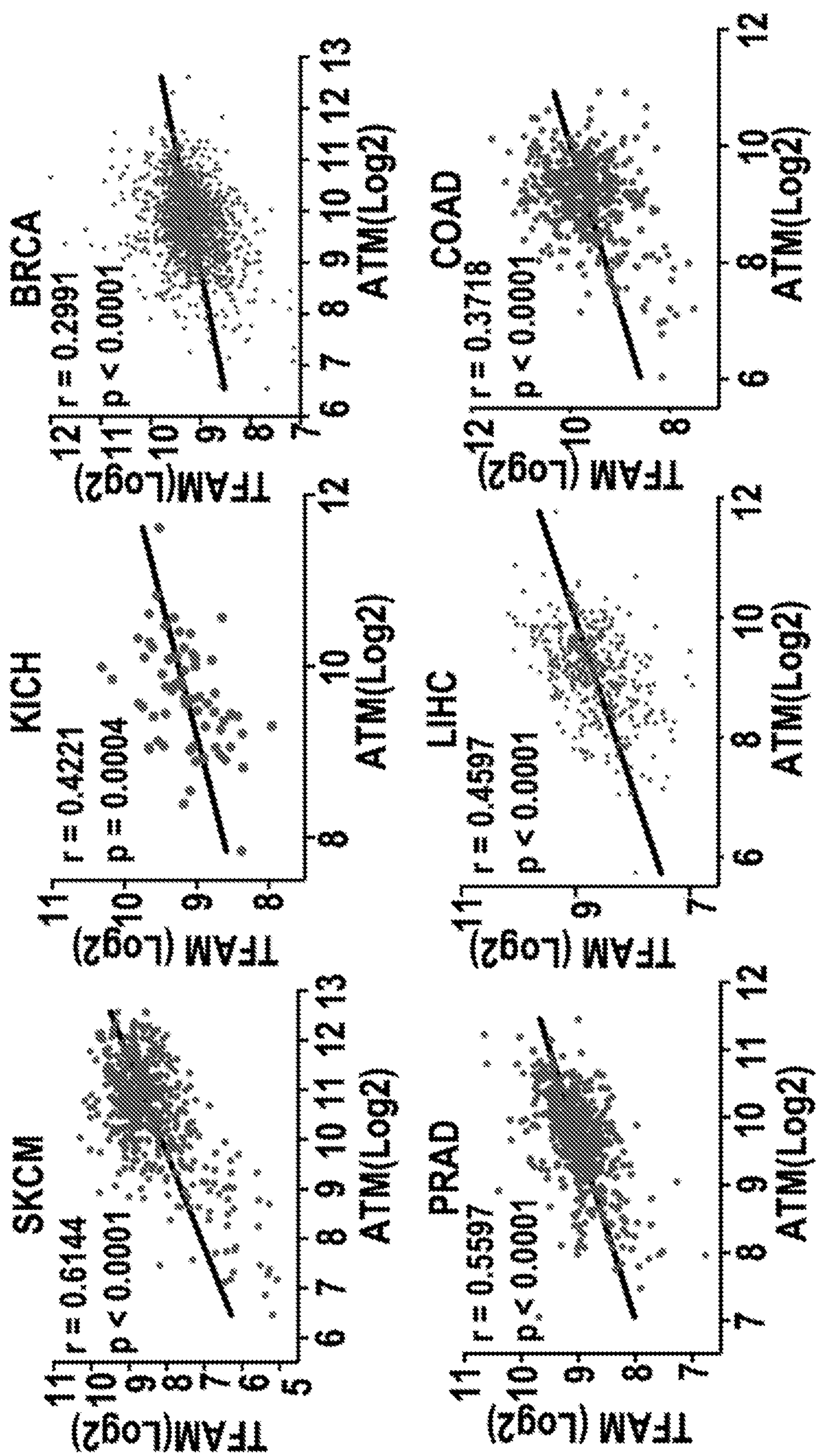
FIG. 64 presents correlation of mRNA expression of ATM and TFAM in human cancer patients using the TCGA dataset. R and p represent Pearson correlation coefficients and two-tailed p values, respectively. Collectively, FIGS. 57-64 demonstrate that ATM inhibition mediates cGas-STING activation by facilitating the release of mitochondria DNA.
Figure 107:
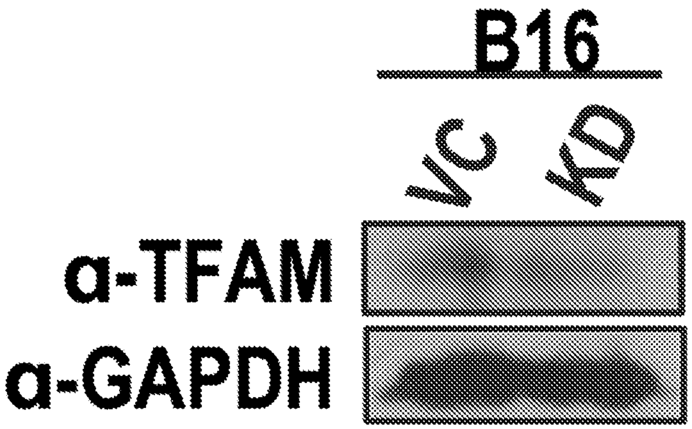
FIG. 107 presents western blot analysis of the expression of TFAM in vector control and TFAM knock down cells.
Figure 108:
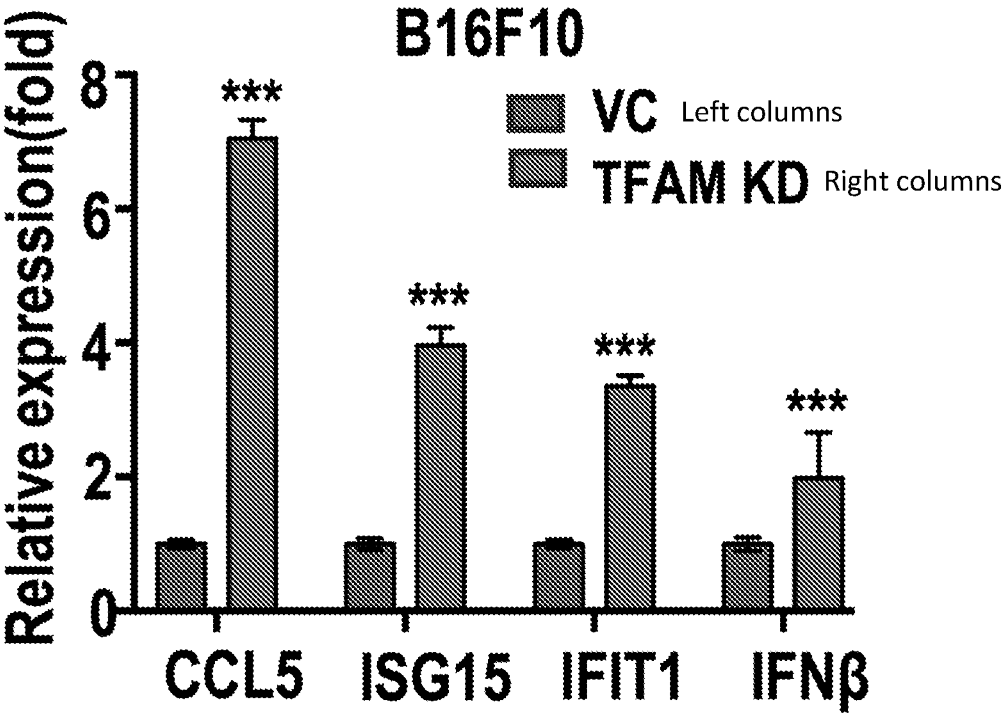
FIG. 108 presents the expression of IFNβ and related ISGs in vector control (VC) and TFAM knock down cells analyzed by real-time q-RT-PCR. Error bars represent SEM. *$p<0.05$, $p<0.01$, *$p<0.001$, ns, not significant, as determined by 2-way ANOVA. Collectively, FIGS. 99-108 provide additional data validating mitochondrial DNA release as key factor in ATM deficiency mediated cGAS-Sting activation.

We next investigated what triggered mitochondrial DNA leakage into the cytosol. GSEA analysis of our RNAseq data suggested that ATMKO significantly downregulated various mitochondria-related gene expression. We therefore focused on mitochondrial transcription factor A (TFAM) is a histone-like protein and a master regulator of mitochondrial biogenesis as well as a regulator of mitochondrial genome replication (Alam, T. I. et al. Nucleic Acids Res (2003) doi: 10.1093/nar/gkg251; Ekstrand, M. I. et al. *Hum Mol Genet* (2004) doi:10.1093/hmg/ddh109), with an important role in mitochondria DNA homeostasis, whose deficiency causes aberrant mtDNA packaging and its leakage into the cytosol and activation of innate interferon response. We thus determined TFAM levels in ATM-deficient B16F10 cells. Indeed, we discovered that protein levels of TFAM decreased significantly in ATM-deficient B16F10 and 4T1 cells when compared with vector control cells (FIGS. 63, 64). We further examined the functional relevance of TFAM as a downstream factor for cGAS/STING activation by knocking it down in B16F10 cells (FIG. 107). TFAM knock down significantly enhanced the expression levels of ISGs (FIG. 108). These results therefore indicate that ATM deficiency induces mtDNA release and cGAS/STING activation by attenuating TFAM expression. We further examined the relationship among ATM and TFAM at the transcriptional level in human cancer patients by analyzing the transcriptome profiles in the TCGA database. Our analysis indicated ATM expression had a strong positive correlation with TFAM expression in multiple human cancers (FIG. 64). Human cancer data were therefore consistent with our experimental observations. Our discovery of the relationship between ATM and TFAM therefore reveals a mechanism through which ATM can regulate interferon response in manner that is independent of its role in coordinating the repair of genomic DNA damage. Collectively, our data indicate ATM is a predictive biomarker and therapeutic target for cancer immunotherapy.

Our work indicates that deficiencies in DNA repair genes such as ATM can stimulate the innate immunity factors in the tumor microenvironment. It revealed the surprising mechanism through which ATM can fine tune cellular innate immunity by regulating TFAM levels. Importantly, our work our study was that small molecule inhibitors of ATM can be used as a systemic cGAS/STING activators and administered together with ICB therapy. Because ATM inhibitors such as AZD1390 and AZD0156 are already being evaluated in clinical trials as sensitizers of radiotherapy, our study shows ATM can be used as both as a predictive biomarker and a therapeutic target for ICB therapy.

Methods

Cell Culture

B16F10 mouse melanoma cells, 4T1 mouse breast carcinoma cells, MDA-MB-231 human breast cancer cells were purchased from the Cell Culture Facilities of Duke University School of Medicine. B16F10, 4T1, MDA-MB-231 cells were all grown in DMEM (Sigma) with 10% fetal bovine serum (FBS). All cell lines were subjected to mycoplasma test by use of the Universal Mycoplasma Detection Kit (ATCC).

Antibodies

FITC anti-mouse CD45 (30-F11), Pacific Blue anti-mouse-CD3 (145-2c11), Alexa Fluor647 anti-mouse CD4 (GK1.5), APC750 anti-mouse-CD8a (53-6.7), PE anti-mouse NK1.1 (PK136), PE anti-mouse-Foxp3 (MF-14), APC anti-γ/δ TCR (GL3), Alexa Fluor647 anti-mouse IFNγ (XMG1.2) and PE anti-mouse F4/80 (BM8) were purchased from Biolegend. Anti-HSP60 (Cat.15282-1-AP), anti-HSP60 (Cat.6604101-1g), anti-GAPDH (Cat.60004) were purchased from Proteintech. Anti-cGAS (Cat. 31659), anti-STING (2P2F) (Cat.13647), anti-TBK1/NAK (D1B4) (Cat.3504), anti-Phospho-TBK1/NAK (Ser172) (D52C2) (Cat.5483), anti-MDA-5 (D74E4) (Cat.5321) were purchased from Cell Signaling Technology. Anti-TFAM (Cat#ab131607), anti-ATM (Cat# Ab199726) were from Abcam.

CRISPR/Cas9-Mediated Gene Knockout of ATM

ATM knockout cells were generated by use of lentivirus mediated CRISPR/Cas9 technology. Single guide RNA (sgRNA) sequences targeting mouse and human ATM gene are listed in the Sequences section herein. Double stranded oligos encoding the sgRNA sequences were cloned into BsmB1 (Thermal Fisher Scientific) digested plasmid LentiCRISPRv2 (deposited by Dr. Feng Zhang of MIT to Addgene), which co-expresses Cas9 and sgRNA in the same vector. CRISPR lentivirus vectors were then produced according to established protocol by the Zhang lab. To generate the knockout cell lines, target cells were infected with lentivirus and cultured in DMEM (with 10% FBS) and selected in puromycin (1 μg/ml for B16, MDA-MB-231 cells and 5 ug/ml for 4T1 cells).

Tumor Growth Delay in Mice

All animal experiments conducted in this study were approved by Duke University Institutional Animal Use and Care Committee. C57BL/6J and Balb/C, mice were purchased from The Jackson Laboratory. NSG mice were purchased from Division of Laboratory Animal Resources (DLAR) of Duke University. Prior to tumor cell injection, age-matched 6-8 weeks old mice were shaved at one of the flanks. Tumor cells were then injected into shaved flanks subcutaneously with Lenti-CRISPRv2 modified control or target gene-specific knockout tumor cells. Tumor volumes were measured every 2-3 days and calculated by the formula: (Length)×(Width)/2. The mice were sacrificed when tumors reached 2000 $mm^3$.

For antibody treatments, mice were given 100 μg antibody via intraperitoneal (i.p.) injection at day 6, 9, 12 post tumor cells injection using following antibodies: anti-PD1 (clone 29F.1A12) or isotype (clone 2A3) from BioXCell.

Lymphocyte Depletion

To evaluate the role of specific subsets of immune effector cells in mice, $CD4^+$T cells, $CD8^+$T cells, and NK cells were depleted with 100 μg of i.p. injected anti-CD4 (BioXcell, GK1.5), 100 ug of anti-CD8b (BioXcell, 53-5.8), and anti-NK1.1 (BioXcell, PK136), respectively, on days 1, 4, 7. Equal amounts of IgG isotype antibodies (BioXcell) were injected as a control.

Analysis of Tumor-Infiltrating Lymphocytes by Flow Cytometry

About $1\times10^5$ ATM knockout or vector control cells were inoculated subcutaneously into C57BL/6J mice. Tumors were excised on day 13 after inoculation, weighted, and mechanically minced and incubated in DNase I (50 ug/ml, Sigma) and collagenase P (2 mg/ml, Sigma) for 20 min at 37° C. The dissociated cells were passed through 70 μm cell strainer (BD). The filtered cells were then blocked with an anti-CD16/32 antibody (BioLegend) and stained with indicated surface antibodies for 20 min on ice. Dead cells were excluded using Live/Dead Fixable Aqua dye (Thermo Fisher Scientific). Intracellular antibodies were added after fixation and permeabilization as manufacturer's instruction (Thermo Fisher Scientific). The anti-mouse fluorochrome-conjugated antibodies were listed in Antibodies section. The stained cells were analyzed by use of a BD Canto flow cytometry system.

Western Blotting

Cells lysates were boiled in sodium dodecyl sulfate (SDS) sample loading buffer, resolved by 10% SDS-polyacrylamide gel electrophoresis (SDS-PAGE) and transferred to nitrocellulose. The membranes were blocked in 5% milk in Tris-buffered saline and Tween 20 (TBST; 10 mM Tris-HCl [pH 8.0], 150 mM NaCl, 0.1% Tween 20) for 1 hr at room temperature. After washing twice with TBST, the membranes were incubated with appropriate primary antibodies in BSA/TBST for overnight and then washed three times with TBST, probed with horseradish peroxide-linked anti-immunoglobulin (1:5000 dilution) for 1 hr at room temperature. After three washes with TBST, immunoreacted products were visualized using enhanced chemiluminescence reagent and autoradiography.

Immunofluorescence

Cells mounted on 35 mm glass bottom poly-d-lysin coated dishes were permeabilized with PBS containing 0.1% Triton X-100 for 30 min, and blocked with 4% bovine serum in PBS for 1 hr at room temperature, followed with incubation with various primary antibodies at room temperature for 3 hrs, and detected by FITC-labeled anti-IgG(1:400) and Cy3-labeled antibody at room temperature for 1 hr. Cells were co-stained with 4',6-diamidino-2-phenylindole (DAPI) to visualize nuclei. IF images were then taken under a fluorescent microscope. Vector control, ATM KO B16 and 4T1 cells were fixed by 4% buffered formalin/PBS. Anti-DNA, Hsp60 were examined by immunostaining.

RNA-Seq

Total cellular RNA from vector control and ATM KO 4T1 cells was prepared using RNeasy Plus RNA extraction kits (QIAGEN). About $1\times10^5$ ATM knockout or vector control B16 cells were inoculated subcutaneously into C57BL/6J mice. Tumor tissues were collected on day 13. Total RNA from tumor was prepared using RNeasy plus Universal Mini kit.

RNA-seq data was processed using the TrimGalore tool kit (Valentin-Vega, Y. A. et al. Blood (2012) doi:10.1182/blood-2011-08-373639) which employs Cutadapt (Martin, M. EMBnet Journal 17, 10-12 (2011)) to trim low-quality bases and Illumina sequencing adapters from the 3' end of the reads. Only reads that were 20 nt or longer after trimming were kept for further analysis. Reads were mapped to the GRCm38.p6 of the mouse genome and transcriptome (Frankish, A et al. Nucleic Acids Res (2019) doi:10.1093/nar/gky955) using the STAR RNA-seq alignment tool (Dobin, A. et al. *Bioinformatics* (2013) doi:10.1093/bioinformatics/bts635). Reads were kept for subsequent analysis if they mapped to a single genomic location using the SAMtools (Li, H. et al. *Bioinformatics* (2009) doi:10.1093/bioinformatics/btp352). Gene counts were compiled using the HTSeq tool (Li, H. ibid;). Only genes that had at least 10 reads in any given library were used in subsequent analysis. Normalization and differential expression were carried out using the DESeq27 Bioconductor (Love, M. I., et al. *Genome Biol* (2014) doi:10.1186/s13059-014-0550-8) package with the R statistical programming environment. Differentially expressed genes (DEGs) were displayed in heatmaps and volcano plot using R program (version 3.6.0). Gene set enrichment analysis (GSEA) version 10 (Mootha, V. K. et al. *Nat Genet* (2003) doi:10.1038/ng1180) was used to identify differentially regulated pathways and gene ontology (GO) terms for the comparisons were used.

Mitochondrial DNA Depletion

A previously published protocol was used (White, M. J. et al. *Cell* (2014) doi:10.1016/j.cell1.2014.11.036). Vector control, ATM KO and wild-type B16 cells were cultured in Dulbecco's modified Eagle's medium (DMEM) with 10% FBS. About 100 ng/ml ethidium bromide was added to the medium for 20 days before the cells were harvested for experiments.

Quantitative RT-PCR

Total RNA was extracted from cells by use of RNeasy Mini Kit (Qiagen) according to manufacturer's instructions. RNA was subjected to cDNA synthesis with random hexamer primers using Superscript II reverse transcriptase (Invitrogen). Quantitative real-time PCR was performed using Quanti Test SYBR Green PCR Master Mix Kit (Qiagen). Primers used for different target genes are listed in the Sequences section herein.

Detection of mtDNA in Cytosolic Extracts

Vector control and ATM KO B16 cells (about $8\times10^6$) were divided into two equal aliquots. One aliquot was resuspended in roughly 500 μl of 50 μM NaOH and boiled for 30 min 5o solubilize DNA. About 50 uL of 1 M Tris-HCl (pH8.0) was added to neutralize the pH of the lysate, and the extracts served as normalization controls for total mtDNA. The second aliquot were resuspended in roughly 5004, buffer containing 150 mM NaCl, 50 mM HEPES pH7.4, and 20 μg/mL digitonin. The homogenates were incubated for 10 min to allow selective plasma permeabilization, then centrifuged at 980 g for 3 min three times to pellet intact cells. The first pellet was saved as the 'Pel' fraction for western blotting. The cytosolic supernatants were transferred to fresh tubes and spun at 17000 g in a microcentriguge for 10 min to pellet any remaining cellular debris, yielding cytosolic preparations free of nuclear, mitochondrial and endoplasmic reticulum contamination. DNA was then purified from these pure cytosolic fractions using DNA Clean & Concentrator-5 kit (ZYMO RESEARCH). Quantitative PCR was performed for both whole-cell extracts and cytosolic fractions using nuclear DNA primers (Tert) and mtDNA primers (Dloop1-3, Cytb, 16S and ND4), and the Ct values obtained for mtDNA abundance for whole-cell extracts served as normalization controls for the mtDNA values obtained from the cytosolic fractions. Primers used for different genes were listed in the Sequences section herein.

Statistical Analysis

Quantitative data are presented as means±SEM, and statistical significance are reported in the figures and/or figure legends. ANOVA with Tukey's post-test (One-way ANOVA for comparisons between groups, Two-way ANOVA for comparisons of magnitude of changes between different groups) was used to compare values among different experimental groups by use of the GraphPad PRISM program. For experiments with only two groups, Student's t test was used as specified in the figure legends. $p<0.05$ was considered statistically significant (*), $p<0.01$ as highly significant (), $p<0.001$ (*) and $p<0.0001$ as extremely significant (****) and ns as not significant. Kaplan-Meier estimator and logrank (Mantel-Cox) test was used for survival analysis tumor bearing mice.

TABLE 1

ATM alterations in the 1,661-patient MSK-TMB study

| Cancer Type | Total | Mutation | Fusion |
|---|---|---|---|
| Bladder Cancer | 215 | 23 | 0 |
| Colorectal Cancer | 110 | 11 | 0 |
| Melanoma | 320 | 26 | 0 |
| Cancer of Unknown Primary | 88 | 7 | 0 |
| Non-Small Cell Lung Cancer | 350 | 23 | 0 |
| Esophagogastric Carcinoma | 126 | 6 | 1 |

TABLE 1-continued

| ATM alterations in the 1,661-patient MSK-TMB study | | | |
|---|---|---|---|
| Cancer Type | Total | Mutation | Fusion |
| Breast Cancer | 44 | 2 | 0 |
| Glioma | 117 | 3 | 0 |
| Renal Cell Carcinoma | 151 | 2 | 0 |
| Head and Neck Cancer | 139 | 1 | 0 |

TABLE 2

ATM alternations in the 10,945-patient MSK-IMPACT study

| Cancer Type | Total | Mutati | Deep | Amplific | Multi- | Fusion |
|---|---|---|---|---|---|---|
| Small Bowl Cancer | 35 | 7 | 0 | 0 | 0 | 0 |
| Skin Cancer, Non- | 148 | 19 | 1 | 0 | 0 | 0 |
| Bladder Cancer | 423 | 45 | 2 | 0 | 0 | 0 |
| Endometrial Cancer | 218 | 24 | 0 | 0 | 0 | 0 |
| Hepatobiliary | 355 | 27 | 0 | 0 | 0 | 0 |
| Colorectal Cancer | 1007 | 75 | 0 | 0 | 0 | 1 |
| Mature B-Cell | 134 | 8 | 0 | 0 | 2 | 0 |
| Non-Small Cell | 1668 | 120 | 0 | 2 | 1 | 0 |
| Melanoma | 365 | 23 | 0 | 0 | 0 | 0 |
| Appendiceal Cancer | 79 | 4 | 0 | 0 | 0 | 0 |
| Small Cell Lung | 82 | 4 | 0 | 0 | 0 | 0 |
| Prostate Cancer | 717 | 25 | 7 | 1 | 0 | 0 |
| Histiocytosis | 22 | 1 | 0 | 0 | 0 | 0 |
| Salivary Gland | 114 | 5 | 0 | 0 | 0 | 0 |
| Thyroid Cancer | 231 | 10 | 0 | 0 | 0 | 0 |
| Cancer of Unknown | 186 | 8 | 0 | 0 | 0 | 0 |
| Breast Cancer | 1324 | 48 | 3 | 2 | 0 | 0 |
| Adrenocortical | 25 | 1 | 0 | 0 | 0 | 0 |
| Mature T and NK | 29 | 1 | 0 | 0 | 0 | 0 |
| Renal Cell | 361 | 12 | 0 | 0 | 0 | 0 |
| Head and Neck | 186 | 14 | 0 | 0 | 0 | 1 |
| Pancreatic Cancer | 502 | 69 | 7 | 2 | 0 | 0 |
| Glioma | 553 | 14 | 1 | 0 | 0 | 0 |
| Soft Tissue Sarcoma | 443 | 13 | 1 | 0 | 0 | 0 |
| Esophagogastric | 341 | 8 | 1 | 0 | 0 | 0 |
| Peripheral Nervous | 80 | 0 | 2 | 0 | 0 | 0 |
| Germ Cell Tumor | 288 | 2 | 0 | 1 | 0 | 1 |
| Ovarian Can | 244 | 2 | 1 | 0 | 0 | 0 |
| Uterine Sarcoma | 93 | 1 | 0 | 0 | 0 | 0 |
| Mesothelioma | 107 | 1 | 0 | 0 | 0 | 0 |
| Bone Cancer | 134 | 1 | 0 | 0 | 0 | 0 |
| Gastrointestinal | 137 | 0 | 0 | 0 | 0 | 1 |

Sequences

A. sgRNA used in CRISPR/Cas9

Human-ATM-sg1 (SEQ ID NO: 01): TTGTTTCAGGATCTCGAATC

Human-ATM-sg2 (SEQ ID NO: 02): GATGCAGGAAATCAGTAGTT

Mouse-ATM-sg1 (SEQ ID NO: 03): CTCTGTCATGCTCTAACTGC

Mouse-ATM-sg2 (SEQ ID NO: 04): CTGTTTCAGGATCCTGAATC

Mouse-TFAM-sg1 (SEQ ID NO: 05): ACGGGGGTCGAGATGTGCGC

Mouse-TFAM-sg2 (SEQ ID NO: 06): TACCAGCGTGGGAACTCCGG

Mouse-cGAS (SEQ ID NO: 07): CAGAATGCAGAAACGGGAGT

-continued

Sequences

Mouse-TBK (SEQ ID NO: 08): TGCCGTTTAGACCCTTCGAG

Mouse-STING (SEQ ID NO: 09): CTTCTCGCTACAACACATGA

Mouse-MDA5 (SEQ ID NO: 10): GGCAGGGATTCAGGCACCAT

B. Oligonucleotide primers for qPCR

Mouse-β-actin (F) (SEQ ID NO: 11): GAAATCGTGCGTGACATCAAA

Mouse-β-actin (R) (SEQ ID NO: 12): TGTAGTTTCATGGATGCCACA

Mouse-IFNβ1 (F) (SEQ ID NO: 13): CTGGCTTCCATCATGAACAA

Mouse-IFNβ1 (R) (SEQ ID NO: 14): AGAGGGCTGTGGTGGAGAA

Mouse-IFNα (F) (SEQ ID NO: 15): GGATGTGACCTTCCTCAGACTC

Mouse-IFNα (R) (SEQ ID NO: 16): ACCTTCTCCTGCGGGAATCCAA

Mouse-CCL5 (F) (SEQ ID NO: 17): CAAGTGCTCCAATCTTGCAGTC

Mouse-CCL5 (R) (SEQ ID NO: 18): TTCTCTGGGTTGGCACACAC

Mouse-IFIT1 (F) (SEQ ID NO: 19): CAAGGCAGGTTTCTGAGGAG

Mouse-IFIT1 (R) (SEQ ID NO: 20): GACCTGGTCACCATCAGCAT

Mouse-ISG15 (F) (SEQ ID NO: 21): CTAGAGCTAGAGCCTGCAG

Mouse-ISG15 (R) (SEQ ID NO: 22): AGTTAGTCACGGACACCAG

Mouse-mtDNA Dloop1 (F) (SEQ ID NO: 23): AATCTACCATCCTCCGTGAAACC

Mouse-mtDNA Dloop1 (R) (SEQ ID NO: 24): TCAGTTTAGCTACCCCCAAGTTTAA

Mouse-mtDNA Dloop2 (F) (SEQ ID NO: 25): CCCTTCCCCATTTGGTCT

Mouse-mtDNA Dloop2 (R) (SEQ ID NO: 26): TGGTTTCACGGAGGATGG

Mouse-mtDNA Dloop3 (F) (SEQ ID NO: 27): TCCTCCGTGAAACCAACAA

Mouse-mtDNA Dloop3 (R) (SEQ ID NO: 28): AGCGAGAAGAGGGGCATT

Mouse-mtDNA CytB (F) (SEQ ID NO: 29): GCTTTCCACTTCATCTTACCATTTA

Mouse-mtDNA CytB (R) (SEQ ID NO: 30): TGTTGGGTTGTTTGATCCTG

Mouse-mtDNA 16S (F) (SEQ ID NO: 31): CACTGCCTGCCCAGTGA

Mouse-mtDNA 16S (R) (SEQ ID NO: 32): ATACCGCGGCCGTTAAA

-continued

| Sequences |
| --- |
| Mouse-mtDNA ND4 (F) (SEQ ID NO: 33): AACGGATCCACAGCCGTA |
| Mouse-mtDNA ND4 (R) (SEQ ID NO: 34): AGTCCTCGGGCCATGATT |
| Mouse-mtDNA-Cox1 (F) (SEQ ID NO: 35): GCCCCAGATATAGCATTCCC |
| Mouse-mtDNA-Cox1 (R) (SEQ ID NO: 36): GTTCATCCTGTTCCTGCTCC |
| Mouse-nucDNA Tert (F) (SEQ ID NO: 37): CTAGCTCATGTGTCAAGACCCTCTT |
| Mouse-nucDNA Tert (R) (SEQ ID NO: 38): GCCAGCACGTTTCTCTCGTT |

NUMBERED EMBODIMENTS

1. A method of enhancing immune checkpoint inhibitor therapy in a subject suffering from a cancer, the method comprising administering to the subject a therapeutically effective amount of at least one ATM inhibitor and at least one immune checkpoint inhibitor such that the activity of the cancer immune checkpoint inhibitor is enhanced.

2. A method of treating cancer in a subject, the method comprising administering to the subject a therapeutically effective amount of at least one ATM inhibitor and at least one immune checkpoint inhibitor such that the cancer is treated in the subject.

3. The method as in any of the preceding claims, wherein the at least one ATM inhibitor activates the cGAS/STING pathway of innate cellular immunity.

4. The method as in any of the preceding claims, wherein the at least one ATM inhibitor increases lymphocyte infiltration into a tumor microenvironment in a subject.

5. The method as in any of the preceding claims, wherein the at least one ATM inhibitor stimulates CD8+ T cell infiltration into a tumor microenvironment in a subject.

6. The method as in any of the preceding claims, wherein the at least one ATM inhibitor stimulates CD4+ T cell infiltration into a tumor microenvironment in a subject.

7. The method as in any of the preceding claims, wherein the at least one ATM inhibitor inhibits cancer cell growth in the subject.

8. The method as in any of the preceding claims, wherein the at least one ATM inhibitor stimulates mitochondrial DNA release in a subject.

9. The method as in any of the preceding claims, wherein the at least one ATM inhibitor stimulates NK cell infiltration into a tumor microenvironment in a subject.

10. The method as in any of the preceding claims, wherein the at least one ATM inhibitor inhibits mitochondrial transcription factor A (TFAM) in a subject.

11. The method as in any of the preceding claims, wherein the at least one ATM inhibitor activates an innate interferon response in a subject.

12. The method as in any of the preceding claims, wherein the at least one ATM inhibitor comprises a small molecule.

13. The method according to claim 12, wherein the at least one ATM inhibitor is selected from the group consisting of KU-55933, KU-60019, KU-559403, NVP-BEZ235, AZD1390, AZD156, AZ31, AZ32, M3541 (also referred to as Merck KGA), Compound 12, Compound 21, N,N-Dimethyl-3-[[5-(3-Methyl-2-Oxo-1-Tetrahydropyran-4-YL-Imidazo[4,5-C]Quinolin-8-YL)-2-Pyridyl]Oxy]Propan-1-amine Oxide, CP-466722, CGK733, siRNAs against the human ATM gene, shRNAs against the human ATM gene, sgRNAs against the human ATM gene, and combinations thereof.

14. The method as in any of the preceding claims, wherein the at least one immune checkpoint inhibitor is a therapy selected from the group consisting of an anti-PD1 therapy, an anti-PD-L1 therapy, an anti-CTLA-4 therapy and combinations thereof.

15. The method according to claim 14, wherein the anti-CTLA4 therapy is selected from the group consisting of ipilimumab, tremelimumab, an anti-CTLA-4 antibody, and combinations thereof.

16. The method according to claim 14, wherein the anti-PD1 therapy is selected from the group consisting of nivolumab, pembrolizumab, pidilizumab, MEDI0680, Libtayo (cemiplimab), M7824 (MSB0011395C) (PDL1 and TGF-beta dual inhibiting antibody), Infinzi (durvaluma), Bavencio (avelumab), Toripalimab, Tyvyt, camrelizumab, Tislelizumab and anti-PD1 antibody, and combinations thereof.

17. The method according to claim 14, wherein the anti-PD-L1 therapy is selected from the group consisting of atezolizumab, BMS-936559, MEDI4736, MSB0010718C, an anti-PD-L1 antibody, and combinations thereof.

18. The method as in any of the preceding claims, wherein the at least one ATM inhibitor is administered prior to the administration of the at least one immune checkpoint inhibitor.

19. The method as in any of claims 1-17, wherein the at least one ATM inhibitor and the at least one immune checkpoint inhibitors are administered concurrently.

20. The method as in any of claims 1-17, wherein the at least one ATM inhibitor is administered after the at least one immune checkpoint inhibitor.

21. The method as in any of the preceding claims in which the cancer comprises a solid tumor.

22. The method as in any of claims 1-20, wherein the cancer comprises a non-solid tumor.

23. The method as in any of claim 21 or 22, wherein the cancer is selected from the group consisting of bladder cancer, colorectal cancer, melanoma, non-small cell lung cancer, esophageal/gastric cancer, breast cancer, glioma, renal cell carcinoma, head and neck cancer, small bowel cancer, non-melanoma skin cancer, endometrial cancer, hepatobiliary cancer, mature B-cell neoplasms, appendiceal cancer, small cell lung cancer, prostate cancer, histiocytosis, salivary gland cancer, thyroid cancer, adrenocortical carcinoma, mature T and NK neoplasms, pancreatic cancer, soft tissue carcinoma, peripheral nervous system cancer, germ cell tumor, ovarian cancer, uterine sarcoma, mesothelioma, bone cancer, gastrointestinal stromal tumor. brain tumors, neuroblastoma, cervical cancer, colon cancer, stomach cancer, intestine cancer, liver cancer, biliary cancer, AML, Hodgkin's lymphoma, Non-Hodgkin's lymphoma, sarcoma, and combinations thereof.

24. The method as in any of the preceding claims, wherein the at least one ATM inhibitor and the at least one immune checkpoint inhibitor are administered intravenously.

25. The method as in any of the preceding claims, wherein the at least one ATM inhibitor and the at least one immune checkpoint inhibitor treatment are administered orally.

26. The method as in any of the preceding claims, wherein either the at least one ATM inhibitor or the at least one immune checkpoint inhibitor treatment is administered intravenously and other is administered orally.

27. The method as in any of the preceding claims, wherein the method further comprises administering to the subject one or more additional agents.

28. The method according to claim 27, wherein the one or more additional agents comprises a chemotherapeutic agent.

29. The method according to claim 28, wherein the chemotherapeutic agent is selected from the group consisting of taxol, doxorubicin, irinotecan temozolomide, and combinations thereof.

30. The method according to claim 27, wherein the one or more additional agent comprises radiation/radiotherapy.

31. The method according to claim 27, wherein the one or more additional agents comprises both a chemotherapeutic agent and radiation/radiotherapy.

32. The method according to claim 31, wherein the chemotherapeutic agent is selected from the group consisting of taxol, doxorubicin, irinotecan temozolomide, and combinations thereof.

33. A method for identifying a subject with a cancer that is suitable for immune checkpoint inhibitor therapy, the method comprising obtaining a sample from the subject with cancer, assaying for a mutation in ATM, wherein when a mutation is detected, the subject is suitable for immune checkpoint inhibitor therapy.

34. The method of claim 29, wherein the ATM mutation is a nonsense mutation.

35. A pharmaceutical composition comprising a therapeutically effective amount of at least one ATM inhibitor, a therapeutically effective amount of at least one immune checkpoint inhibitor, and a pharmaceutically acceptable carrier/excipient.

36. The pharmaceutical composition according to claim 35, wherein the at least one ATM inhibitor is selected from the group consisting of KU-55933, KU-60019, KU-559403, NVP-BEZ235, AZD1390, AZD156, AZ31, AZ32, M3541 (also referred to as Merck KGA), Compound 12, Compound 21, N,N-Dimethyl-3-[[5-(3-Methyl-2-Oxo-1-Tetrahydropyran-4-YL-Imidazo[4,5-C]Quinolin-8-YL)-2-Pyridyl]Oxy] Propan-1-amine Oxide, CP-466722, CGK733 and combinations thereof.

37. The pharmaceutical composition as in any of claim 35 or 36, wherein the at least one immune checkpoint inhibitor is a therapy selected from the group consisting of an anti-PD1 therapy, an anti-PD-L1 therapy, an anti-CTLA-4 therapy and combinations thereof.

38. The pharmaceutical composition according to claim 37, wherein the anti-CTLA4 therapy is selected from the group consisting of ipilimumab, tremelimumab, an anti-CTLA-4 antibody, and combinations thereof.

39. The pharmaceutical composition according to claim 37, wherein the anti-PD1 therapy is selected from the group consisting of nivolumab, pembrolizumab, pidilizumab, MEDI0680, Libtayo (cemiplimab), M7824 (MSB0011395C) (PDL1 and TGF-beta dual inhibiting antibody), Infinzi (durvaluma), Bavencio (avelumab), Toripalimab, Tyvyt, camrelizumab, Tislelizumab and anti-PD1 antibody, and combinations thereof.

40. The pharmaceutical composition according to claim 37, wherein the anti-PD-L1 therapy is selected from the group consisting of atezolizumab, BMS-936559, MEDI4736, MSB0010718C, an anti-PD-L1 antibody, and combinations thereof.

41. All that is described and illustrated herein.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims. In addition, the section headings used herein are for organizational purposes only and are not to be construed as limiting the subject matter described.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise.

The present disclosure shall control in the event there are any disparities between any definitions and/or description found in the cited references.

What is claimed is:

1. A method of enhancing immune checkpoint inhibitor therapy in a subject suffering from a cancer, the method comprising administering to the subject a therapeutically effective amount of at least one ATM inhibitor and at least one immune checkpoint inhibitor such that the activity of the cancer immune checkpoint inhibitor is enhanced.

2. A method of treating cancer in a subject, the method comprising administering to the subject a therapeutically effective amount of at least one ATM inhibitor and at least one immune checkpoint inhibitor such that the cancer is treated in the subject.

3. The method of claim 1, wherein the at least one ATM inhibitor activates the cGAS/STING pathway of innate cellular immunity.

4. The method of claim 1, wherein the at least one ATM inhibitor comprises a small molecule.

5. The method according to claim 4, wherein the at least one ATM inhibitor is selected from the group consisting of KU-55933, KU-60019, KU-559403, NVP-BEZ235, AZD1390, AZD156, AZ31, AZ32, M3541 (also referred to as Merck KGA), Compound 12, Compound 21, N,N-Dimethyl-3-[[5-(3-Methyl-2-Oxo-1-Tetrahydropyran-4-YL-Imidazo[4,5-C]Quinolin-8-YL)-2-Pyridyl]Oxy]Propan-1-amine Oxide, CP-466722, CGK733, siRNAs against the human ATM gene, shRNAs against the human ATM gene, sgRNAs against the human ATM gene, and combinations thereof.

6. The method-of claim 1, wherein the at least one immune checkpoint inhibitor is a therapy selected from the group consisting of an anti-PD1 therapy, an anti-PD-L1 therapy, an anti-CTLA-4 therapy and combinations thereof.

7. The method according to claim 6, wherein the anti-CTLA4 therapy is selected from the group consisting of ipilimumab, tremelimumab, an anti-CTLA-4 antibody, and combinations thereof.

8. The method according to claim 6, wherein the anti-PD1 therapy is selected from the group consisting of nivolumab, pembrolizumab, pidilizumab, MEDI0680, Libtayo (cemiplimab), M7824 (MSB0011395C) (PDL1 and TGF-beta dual inhibiting antibody), Infinzi (durvaluma), Bavencio (avelumab), Toripalimab, Tyvyt, camrelizumab, Tislelizumab and anti-PD1 antibody, and combinations thereof.

9. The method according to claim 6, wherein the anti-PD-L1 therapy is selected from the group consisting of atezolizumab, BMS-936559, MEDI4736, MSB0010718C, an anti-PD-L1 antibody, and combinations thereof.

10. The method of claim 1, wherein the at least one ATM inhibitor is administered prior to the administration of the at least one immune checkpoint inhibitor, the at least one ATM inhibitor and the at least one immune checkpoint inhibitors are administered concurrently, or the at least one ATM inhibitor is administered after the at least one immune checkpoint inhibitor.

11. The method of claim 1, wherein the cancer comprises a solid tumor.

12. The method of claim 1, wherein the cancer comprises a non-solid tumor.

13. The method of claim 11, wherein the cancer is selected from the group consisting of bladder cancer, colorectal cancer, melanoma, non-small cell lung cancer, esophageal/gastric cancer, breast cancer, glioma, renal cell carcinoma, head and neck cancer, small bowel cancer, non-melanoma skin cancer, endometrial cancer, hepatobiliary cancer, mature B-cell neoplasms, appendiceal cancer, small cell lung cancer, prostate cancer, histiocytosis, salivary gland cancer, thyroid cancer, adrenocortical carcinoma, mature T and NK neoplasms, pancreatic cancer, soft tissue carcinoma, peripheral nervous system cancer, germ cell tumor, ovarian cancer, uterine sarcoma, mesothelioma, bone cancer, gastrointestinal stromal tumor, brain tumors, neuroblastoma, cervical cancer, colon cancer, stomach cancer, intestine cancer, liver cancer, biliary cancer, AML, Hodgkin's lymphoma, Non-Hodgkin's lymphoma, sarcoma, and combinations thereof.

14. The method of claim 1, wherein the at least one ATM inhibitor and the at least one immune checkpoint inhibitor are administered intravenously, the at least one ATM inhibitor and the at least one immune checkpoint inhibitor treatment are administered orally, or either the at least one ATM inhibitor or the at least one immune checkpoint inhibitor treatment is administered intravenously and other is administered orally.

15. The method of claim 1, wherein the method further comprises administering to the subject one or more additional agents.

16. The method according to claim 15, wherein the one or more additional agents comprises a chemotherapeutic agent.

17. The method according to claim 16, wherein the chemotherapeutic agent is selected from the group consisting of taxol, doxorubicin, irinotecan temozolomide, and combinations thereof.

18. The method according to claim 15, wherein the one or more additional agent comprises radiation/radiotherapy.

19. The method according to claim 15, wherein the one or more additional agents comprises both a chemotherapeutic agent and radiation/radiotherapy.

20. The method according to claim 19, wherein the chemotherapeutic agent is selected from the group consisting of taxol, doxorubicin, irinotecan temozolomide, and combinations thereof.

21. A pharmaceutical composition comprising a therapeutically effective amount of at least one ATM inhibitor, a therapeutically effective amount of at least one immune checkpoint inhibitor, and a pharmaceutically acceptable carrier/excipient.

22. The pharmaceutical composition according to claim 21, wherein the ATM inhibitor is selected from the group consisting of KU-55933, KU-60019, KU-559403, NVP-BEZ235, AZD1390, AZD156, AZ31, AZ32, M3541 (also referred to as Merck KGA), Compound 12, Compound 21, N,N-Dimethyl-3-[[5-(3-Methyl-2-Oxo-1-Tetrahydropyran-4-YL-Imidazo[4,5-C]Quinolin-8-YL)-2-Pyridyl]Oxy]Propan-1-amine Oxide, CP-466722, CGK733 and combinations thereof.

23. The pharmaceutical composition of claim 21, wherein the at least one immune checkpoint inhibitor is a therapy selected from the group consisting of an anti-PD1 therapy, an anti-PD-L1 therapy, an anti-CTLA-4 therapy and combinations thereof.

24. The pharmaceutical composition according to claim 23, wherein the anti-CTLA4 therapy is selected from the group consisting of ipilimumab, tremelimumab, an anti-CTLA-4 antibody, and combinations thereof.

25. The pharmaceutical composition according to claim 23, wherein the anti-PD1 therapy is selected from the group consisting of nivolumab, pembrolizumab, pidilizumab, MEDI0680, Libtayo (cemiplimab), M7824 (MSB0011395C) (PDL1 and TGF-beta dual inhibiting antibody), Infinzi (durvaluma), Bavencio (avelumab), Toripalimab, Tyvyt, camrelizumab, Tislelizumab and anti-PD1 antibody, and combinations thereof.

26. The pharmaceutical composition according to claim 23, wherein the anti-PD-L1 therapy is selected from the group consisting of atezolizumab, BMS-936559, MEDI4736, MSB0010718C, an anti-PD-L1 antibody, and combinations thereof.

* * * * *